US011414483B2

(12) United States Patent
Kamperman et al.

(10) Patent No.: US 11,414,483 B2
(45) Date of Patent: Aug. 16, 2022

(54) POROUS AFFINITY HYDROGEL PARTICLES FOR REDUCING THE BIOAVAILABILITY OF SELECTED BIOLOGICAL MOLECULES

(71) Applicant: HY2CARE B.V., Enschede (NL)

(72) Inventors: Tom Kamperman, Enschede (NL); Lisanne Paula Karbaat, Enschede (NL); Hermanus Bernadus Johannes Karperien, Enschede (NL); Jeroen Christianus Hermanus Leijten, Enschede (NL); Pieter Jelle Dijkstra, Enschede (NL); Bram Zoetebier, Enschede (NL)

(73) Assignee: HY2CARE B.V., Enschede (NL)

( * ) Notice: Subject to any disclaimer, the term of this patent is extended or adjusted under 35 U.S.C. 154(b) by 5 days.

(21) Appl. No.: 16/962,643

(22) PCT Filed: Jan. 18, 2019

(86) PCT No.: PCT/NL2019/050031
§ 371 (c)(1),
(2) Date: Jul. 16, 2020

(87) PCT Pub. No.: WO2019/143247
PCT Pub. Date: Jul. 25, 2019

(65) Prior Publication Data
US 2020/0347125 A1 Nov. 5, 2020

(30) Foreign Application Priority Data
Jan. 18, 2018 (EP) ..................................... 18152397

(51) Int. Cl.
*C07K 16/24* (2006.01)
*A61K 9/16* (2006.01)

(52) U.S. Cl.
CPC ............ *C07K 16/24* (2013.01); *A61K 9/1641* (2013.01); *C07K 2317/622* (2013.01)

(58) Field of Classification Search
CPC .......................... C08J 2300/12; C08J 2300/14; C08J 2305/08; C08J 2305/02; C08J 3/075;
(Continued)

(56) References Cited

U.S. PATENT DOCUMENTS

| 8,440,231 B2 | 5/2013 | Smyth et al. |
| 8,647,271 B2 | 2/2014 | Müller et al. |

(Continued)

FOREIGN PATENT DOCUMENTS

| WO | 9915211 A1 | 4/1994 |
| WO | 2011049449 A1 | 4/2011 |

(Continued)

OTHER PUBLICATIONS

Grainger, D.W., Controlled-Release and Local Delivery of Therapeutic Antibodies, Expert Opinion Biol. Ther., 2004, pp. 1029-1044, 4(7), Ashley Publications Ltd.
(Continued)

*Primary Examiner* — Jianfeng Song
(74) *Attorney, Agent, or Firm* — Hudak, Shunk & Farine Co. LPA

(57) ABSTRACT

A hydrogel particle that has an average cross-sectional diameter in the range from 1 micrometer (μm) to 1000 μm, wherein the particle includes a first polymer network with an average mesh size that allows diffusion of a molecule with an hydrodynamic radius of 1000 nanometer (nm) or less into the first polymer network and which particle includes one or more binding molecules that are immobilized by the polymer network. The hydrogel particle preferably has wherein the first polymer network has an average mesh size that prevents diffusion of a molecule with an average hydrody-
(Continued)

namic radius of more than 1000 nm to diffuse into the first polymer network, preferably the mesh size prevents diffusion of a molecule with an average hydrodynamic radius of more than 100 nm, and preferably more than 5 nm. Methods for reducing the bioavailability of one or more soluble biological molecules in a biological system by using the described hydrogel particle.

19 Claims, 22 Drawing Sheets

(58) Field of Classification Search
CPC .... C08J 2371/02; A61K 9/0019; A61K 47/36; A61K 9/1652; A61K 9/1641; C07K 16/24; C07K 2317/622
See application file for complete search history.

(56) References Cited

U.S. PATENT DOCUMENTS

| | | | |
|---|---|---|---|
| 2006/0257488 A1 | 11/2006 | Hubbard | |
| 2012/0276069 A1* | 11/2012 | Karperien | A61L 27/3817 424/93.7 |
| 2012/0276103 A1* | 11/2012 | Karperien | C07K 16/44 424/135.1 |

FOREIGN PATENT DOCUMENTS

| | | | |
|---|---|---|---|
| WO | 2011059325 A2 | 5/2011 | |
| WO | 2013073941 A1 | 5/2013 | |
| WO | 2016172143 A1 | 10/2016 | |
| WO | WO-2016172143 A1 * | 10/2016 | ............... C08J 3/075 |

OTHER PUBLICATIONS

Chevalier, X., et al., Intraarticular Injection of Anakinra in Osteoarthritis of the Knee: A Multicenter, Randomized, Double-Blind, Placebo-Controlled Study, Arthritis & Rheumatism (Arthtritis Care & Research), Mar. 15, 2009, pp. 344-352, vol. 61, No. 3, American College of Rheumatology.
Joosten, Leo A.B., et al., Anticytokine Treatment of Established Type II Collagen-Induced Arthritis in DBA/1 Mice, A Comparative Study Using Anti-TNF Alpha, Anti-IL-1 Alpha/Beta, and IL-1Ra, Arthritis & Rheumatism, May 1996, pp. 797-809, vol. 39, No. 5, American College of Rheumatology.
Giteau, A., et al., How to Achieve Sustained and Complete Protein Release from PLGA-Based Microparticles?, International Journal of Pharmaceutics, 2008, pp. 1-52, vol. 350 (1-2), Elsevier.
Samad, A., et al., Liposomal Drug Delivery Systems: An Update Review, Current Drug Delivery, 2007, pp. 297-305, vol. 4, Bentham Science Publishers Ltd.
Bezemer, J.M., et al., Microspheres for Protein Delivery Prepared from Amphiphilic Multiblock Copolymers, 2. Modulation of Release Rate, Journal of Controlled Release, 2000, pp. 249-260, vol. 67, Elsevier Science B.V.
Brown, K.E., et al., Gelatin/Chondroitin 6-Sulfate Microspheres for the Delivery of Therapeutic Proteins to the Joint, Arthritis & Rheumatism, Dec. 1998, pp. 2185-2195, vol. 41, No. 12, American College of Rheumatology.
Agarwal, R., et al., Synthesis of Self-Assembled IL-1 Ra-Presenting Nanoparticles for the Treatment of Osteoarthritis, J Biomed Mater Res A, 2016, pp. 595-599, vol. 104A, Wiley Periodicals, Inc.
Singh, A., et al., Nanoengineered Particles for Enhanced Intra-Articular Retention and Delivery of Proteins, Adv Healthcare Mater, 2014, pp. 1562-1567, vol. 3, Wiley-VCH Verlag GmbH & Co., KGaA, Weinheim.
Whitmire, R.E., et al., Self-Assembling Nanoparticles for Intra-Articular Delivery of Anti-Inflammatory Proteins, Biomaterials, 2012, pp. 7665-7675, vol. 33, Elsevier Ltd.

Kohane, D.S., Microparticles and Nanoparticles for Drug Delivery, Biotechnology and Bioengineering, 2007, pp. 203-209, vol. 96, No. 2, Wiley Periodicals, Inc.
Pradal, J., et al., Effect of Particle Size on the Biodistribution of Nano- and Microparticles Following Intra-Articular Injection in Mice, International Journal of Pharmaceutics, 2016, pp. 119-129, vol. 498, Elsevier B.V.
Sousa F., et al., Nanoparticles for the Delivery of Therapeutic Antibodies: Dogma or Promising Strategy?, Expert Opinion on Drug Delivery, 2016, pp. 1163-1176, vol. 14, No. 10, Taylor & Francis Group.
Helmick, C.G., et al., Estimates of the Prevalence of Arthritis and Other Rheumatic Conditions in the United States: Part I, Arthritis & Rheumatism, Jan. 2008, pp. 15-25, vol. 58, No. 1, American College of Rheumatology.
CDC, Cost Statistics, The Cost of Arthritis in US Adults, https://www.cdc.gov/arthritis/data_statistics/cost.htm.
Wang, R., Macromolecular Engineering of In-Situ Forming Hydrogels, Department of Developmental BioEngineering (DBE), Faculty of Science and Technology (TNW), University of Twente, Enschede, Jan. 2016, pp. 1-180, Gildeprint, Enschede, Netherlands.
Jin, R. et al., Enzyme-Mediated Fast in Situ Formation of Hydrogels from Dextran-Tyramine Conjugates, Biomaterials, Feb. 2007, pp. 2791-2800, vol. 28, Elsevier, Ltd.
Kamperman, T. et al. (2017) Centering Single Cells in Microgels via Delayed Crosslinking Supports Long-Term 3D Culture by Preventing Cell Escape, Small, 2017, pp. 1-10, vol. 13, 1603711, Wiley-VCH Verlag GmbH & Co., KGaA, Weinheim.
Chicheportiche, D. and Reach, G., In Vitro Kinetics of Insulin Release by Microencapsulated Rat Islets: Effect of the Size of the Microcapsules, Diabetologia, 1988, pp. 54-57, vol. 31, Springer-Verlag.
Headen, D.M. et al. (2014) Microfluidic-Based Generation of Size-Controlled, Biofunctionalized Synthetic Polymer Microgels for Cell Encapsulation, Advanced Materials, 2014, pp. 3003-3008, vol. 26, Wiley-VCH Verlag GmbH & Co., KGaA, Weinheim.
Cadee, J.A. et al., In Vivo Biocompatibility of Dextran-Based Hydrogels, Journal of Biomedical Materials Research, 2000, pp. 397-404, vol. 50, John Wiley & Sons, Inc.
Formiga, F.R. et al.. Biodegradation and Heart Retention of Polymeric Microparticles in a Rat Model of Myocardial Ischemia, European Journal of Pharmaceutics and Biopharmaceutics, 2013, pp. 665-672, vol. 85, Elsevier B.V.
Tran V.-T. et al., Why and How to Prepare Biodegradable, Monodispersed, Polymeric Microparticles in the Field of Pharmacy?, International Journal of Pharmaceutics, 2011, pp. 1-11, vol. 407, Elsevier B.V.
Lima, A.C. et al., Production Methodologies of Polymeric and Hydrogel Particles for Drug Delivery Applications, Expert Opinion on Drug Delivery, 2012, pp. 231-248, vol. 9, No. 2, Taylor & Francis Group.
Buwalda, S.J. et al., Hydrogels in a Historical Perspective: From Simple Networks to Smart Materials, Journal of Controlled Release, 2014, pp. 254-273, vol. 190, Elsevier B.V.
Strokappe, N. et al., Llama Antibody Fragments Recognizing Various Epitopes of the CD4bs Neutralize a Broad Range of HIV-1 Subtypes A, B and C, Open Access, Mar. 2012, pp. 1-11, vol. 7, No. 3, e33298, PLoS One.
Frenken L.G. et al., Isolation of Antigen Specific Llama VHH Antibody Fragments and Their High Level Secretion by *Saccharomyces cerevisiae*, Journal of Biotechnology, 2000, pp. 11-21, vol. 78, Elsevier Science B.V.
Roovers, R.C. et al., Efficient Inhibition of EGFR Signalling and of Tumour Growth by Antagonistic Anti-EFGR Nanobodies, Cancer Immunol Immunother, 2007, pp. 303-317, vol. 56, Springer-Verlag.
El Khattabi, M. et al., Llama Single-Chain Antibody that Blocks Lipopolysaccharide Binding and Signaling: Prospects for Therapeutic Applications, Clinical and Vaccine Immunology, 2006, pp. 1079-1086, vol. 13, No. 10, American Society for Microbiology.
Oliveira, S. et al., Targeting Tumors with Nanobodies for Cancer Imaging and Therapy, Journal of Controlled Release, 2013, pp. 607-617, vol. 172, Elsevier B.V.

(56) References Cited

OTHER PUBLICATIONS

Zhang, Y., I-TASSER Server for Protein 3D Structure Prediction, BMC Bioinformatics, 2008, pp. 1-8, vol. 9, No. 40, BioMed Central.

Roy, A. et al., I-TASSER: A Unified Platform for Automated Protein Structure and Function Prediction, National Institutes of Health, Apr. 2010, pp. 1-24, vol. 5, No. 4, Nat Protoc.

Roy, A. et al., COFACTOR: An Accurate Comparative Algorithm for Structure-Based Protein Function Annotation, Nucleic Acids Research, 2012, (Web Server issue), W471-477, vol. 40, Oxford University Press.

De Groot, C.J. et al., In Vitro Biocompatibility of Biodegradable Dextran-Based Hydrogels Tested with Human Fibroblasts, Biomaterials, 2001, pp. 1197-1203, vol. 22, Elsevier Science Ltd.

Segura, T. et al., Crosslinked Hyaluronic Acid Hydrogels: A Strategy to Functionalize and Pattern, Biomaterials, 2005, pp. 359-371, vol. 26, Elsevier Ltd.

Both, S.K. et al., A Rapid and Efficient Method for Expansion of Human Mesenchymal Stem Cells, Tissue Engineering, 2007, pp. 3-9, vol. 13, No. 1, Mary Ann Liebert, Inc.

Moreira Teixeira, L.S. et al., High Throughput Generated Micro-Aggregates of Chondrocytes Stimulate Cartilage Formation in Vitro and in Vivo, European Cells and Materials, 2012, pp. 387-399, vol. 23.

Seidlits, S.K. et al., High-Resolution Patterning of Hydrogels in Three Dimensions using Direct-Write Photofabrication for Cell Guidance, Advanced Functional Materials, 2009, pp. 3543-3551, vol. 19, Wiley-VCH Verlag GmbH & Co. KGaA, Weinhem.

Chaudhuri, O. et al., Hydrogels with Tunable Stress Relaxation Regulate Stem Cell Fate and Activity, Nat Mater, 2016, pp. 1-21, vol. 15, No. 3.

Burdick, J.A. and Anseth, K.S., Photoencapsulation of Osteoblasts in Injectable RGD-Modified PEG Hydrogels for Bone Tissue Engineering, Biomaterials, 2002, pp. 4315-4323, vol. 23, Elsevier Science Ltd.

Henke, S. et al., Enzymatic Crosslinking of Polymer Conjugates is Superior over Ionic or UV Crosslinking for the On-Chip Production of Cell-Laden Microgels, Macromolecular Bioscience, 2016, pp. 1524-1532, vol. 16, Wiley-VCH Verlag GmbH & Co. KGaA, Weinhem.

Hoffman, Allan S., Hydrogels for Biomedical Applications, Advanced Drug Delivery Reviews, 2012, pp. 18-23, vol. 64, Elsevier B.V.

Laftah, W.A., et al., Polymer Hydrogels: A Review, Polymer-Plastics Technology and Engineering, Taylor & Francis, 2017, pp. 1475-1486, vol. 50, No. 14, Taylor & Francis Group.

Russell, Shawn M., et al., Mesh Size of Charged Polyacrylamide Hydrogels from Partitioning Measurements, Ind. Eng. Chem. Res., 2005, pp. 8213-8217, vol. 44, American Chemical Society.

Grassi, Mario, et al., Structural Characterization of Calcium Alginate Matrices by Means of Mechanical and Release Tests, Molecules, 2009, pp. 3003-3017, vol. 14.

Erickson, Harold P., et al., Size and Shape of Protein Molecules at the Nanometer Level Determined by Sedimentation, Gel Filtration, and Electron Microscopy, Biological Procedures Online, 2009, pp. 32-51, vol. 11, No. 1, Springer.

Stetefeld, J., et al., Dynamic Light Scattering: A Practical Guide and Applications in Biomedical Sciences, Biophys. Rev., 2016, pp. 409-427, vol. 8, Springer.

Reverdatto, Sergey, et al., Peptide Aptamers: Development and Applications, Curr Top Med Chem., 2015, pp. 1-38, vol. 15, No. 12, Bentham Science Publishers.

Tamburro, Davide, et al., Multifunctional Core—Shell Nanoparticles: Discovery of Previously Invisible Biomarkers, American Chemical Society, 2011, pp. 19178-19188, vol. 133, American Chemical Society.

Witchterle, O. et al., Hydrophilic Gels for Biological Use, Nature, 1960, No. 4706, pp. 117-118, Nature Publishing Group.

\* cited by examiner

'Cytokine sink' concept

ß-strabd interaction

ß-strand structure

Complementary determining region (CDR)

Loop structures

A

| FR1 | CDR1 | FR2 |
| --- | --- | --- |
| EVQLVESGGGLVQAGGSLRLSCAAS | GFTFDDYI | IGWFRQAPGKEREGISCI |

| CDR2 | FR3 |
| --- | --- |
| SSSDGST | YYADSVTGRFGISSDNAKNTVYLQMNSLKPEDTAVYYCAA |

| CDR3 | FR4 |
| --- | --- |
| HAKWPYGTYSFRRCRRASFDY | WGKGTLVTVSS |

B

C

POROUS AFFINITY HYDROGEL PARTICLES FOR REDUCING THE BIOAVAILABILITY OF SELECTED BIOLOGICAL MOLECULES

FIELD OF THE INVENTION

The invention relates to means to and methods for removing biological molecules from the direct surroundings. More specifically to hydrogel particles with an internal immobilized binding molecule that can bind and sequester a biological molecule. The particles can be used to reduce or inhibit the bioactivity of a biological molecule. The hydrogel particles are preferably injectable.

BACKGROUND OF THE INVENTION

Many (chronic/progressive) inflammatory, infectious, and genetic diseases/conditions (e.g. osteoarthritis, inflammatory arthritis, rheumatoid arthritis, Crohn's disease, asthma, bacterial infections, sepsis and whole organ failure, cancer, and transplant rejections) are regulated and maintained through cell signaling molecules (i.e. pro- and anti-inflammatory cytokines and growth factors, growth factor antagonists; herein further referred to as soluble factors). Neutralizing these soluble factors using antibodies is a potent way to stabilize or even cure such diseases. Various soluble factor-neutralizing strategies have been developed to this end, and some are even implemented in advanced clinical therapies. These soluble factor neutralizing therapies typically rely on the bolus injection of antibodies or antibody-releasing agents/particles and have, for example, been extensively used for the treatment of systemic diseases such as rheumatoid arthritis. They also been tested for local modulation of inflammation such as the case in (knee) osteoarthritis.[1-3] In these conditions the neutralizing antibodies are injected intra-articularly with the intend to keep the antibodies in the local joint environment. However, these therapies have shown limited efficacy due to the rapid clearance of intra-articular bolus injections. Similar high level of clearance occur in numerous other sites, where the bolus injected molecules are rapidly cleared via the fluid circulation to and in vascular and lymphatic systems. In addition, bolus injected antibodies can be rapidly cleared by (immune) cell mediated phagocytosis. Also bolus injections at the site of inflammation appear largely ineffective due to the rapid dissolution of the antibodies in bodily fluids. To prolong the therapeutic effect of injected antibodies for localized treatment of inflammation, various antibody releasing particles with longer intra-articular retention times have been investigated.[4-7] Alternatively, antibodies have been covalently tethered onto the surface of particles.[8-10] In summary, there currently exist two approaches for the controlled presentation of cytokine neutralizing antibodies: i) controlled in situ release of cytokine-neutralizing moieties, and ii) capturing cytokines using surface-modified nanoparticles, as schematically depicted in FIG. 1.

The state-of-the-art injectable drug delivery systems do prolong the in vivo/in situ retention time of cytokine neutralizing agent (e.g. antibodies). However, they are still far from optimal. For instance the antibodies are directly released into/exposed to the harsh (e.g. inflamed) in vivo environment. Consequently, the biological function of the therapeutic agents is compromised due to, for example, protein denaturation. Importantly, damaged antibodies can be even counter effective by having an increased immunogenicity. Also, nanoparticles can induce oxidative stress and pro-inflammatory responses leading to toxic effects, are relatively quickly cleared (e.g. via 'leaky vasculature' in inflamed tissue), and are more prone to scavenging by phagocytosis as compared to microparticles. Having an antibody on a surface even facilitates phagocytosis, this is mediated via immune complexes formed on the surface. Furthermore, antibodies presented on the surface of nano- or microparticles are not protected against non-specific interactions with body fluids, resulting in a suboptimal affinity against cytokines of interest.

The present invention provides 'injectable biological molecule sinks', which are affinity hydrogel particles for local sequestration or depletion of the selected biological molecule.

SUMMARY OF THE INVENTION

Provided is a hydrogel particle that has an average cross-sectional diameter in the range from 1 micrometer (μm) to 1000 μm, wherein the particle comprises a first polymer network with an average mesh size that allows diffusion of a molecule with an hydrodynamic radius of 1000 nanometer (nm) or less into the first polymer network and which particle comprises a binding molecule that is immobilized by the polymer network. The first polymer network preferably has a mesh size that is not penetrable for a molecule with an average hydrodynamic radius of more than 1000 nm, preferably more than 100 nm. The binding molecule preferably binds a biological molecule. The binding molecule preferably binds specifically to the biological molecule. Such a binding molecule is also referred to as a specific binding molecule. The first polymer network preferably comprises the binding molecule that is immobilized in the first polymer network.

The invention further provides a hydrogel particle that has an average cross-sectional diameter in the range from 1 micrometer (μm) to 1000 μm, wherein the particle comprises a first polymer network with an average mesh size that allows diffusion of a molecule with an hydrodynamic radius of 1000 nanometer (nm) or less into the first polymer network and which particle comprises a binding molecule that is immobilized by the polymer network, and which binding molecule specifically binds said molecule. Said molecule is a molecule with hydrodynamic radius of 1000 nanometer (nm) or less.

The hydrogel particle preferably comprises two or more binding molecules wherein at least two of said binding molecules bind a different target biological molecule. In a preferred embodiment the particle comprises three or more binding molecules wherein at least three of said binding molecules bind different target biological molecules. Methods and uses of hydrogel particles as described herein is often in situations where it is helpful if the immediate surroundings of the particles is depleted for several soluble factors at the same time. In such cases it can be helpful to incorporate more than one biological molecule in a particle.

For many purposes a plurality of particles is administered, particularly for the purpose of capturing significant amounts of biological molecule over a longer period of time. The particles can be more or less the same. The invention thus also provides a composition of hydrogel particles comprising a plurality of hydrogel particles as described herein.

The invention also provides a composition comprising a pool of at least two collections of hydrogel particles as described herein, wherein the hydrogel particles of at least two of said pools comprise binding molecules that bind different biological molecules.

Also provided is a hydrogel particle as described herein or a pharmaceutical solution or composition comprising said hydrogel particles or composition comprising a pool as described herein, for use in the treatment of a patient with an over-active immune system, a cancer, or over-active hormone and/or cytokine producing cells, preferably in the treatment of inflammation, preferably in the treatment of joint-inflammation. The patient with an over-active immune system can be an auto-immune disease patient, a patient with an inflammation or the like.

Also provided is an aqueous solution suitable for injection comprising the hydrogel particle as described herein.

Also provided is a method for reducing the bioavailability of a soluble biological molecule in a biological system, the method comprising providing said system with hydrogel particles as described herein, wherein the biological molecule comprises a hydrodynamic radius that can access said polymer network and said binding molecule can bind said biological molecule.

Further provided is a use of a hydrogel particle as described herein or a pharmaceutical solution or composition comprising said hydrogel particle for reducing the bioavailability of a biological molecule in a biological system.

Also provided is an aqueous solution, preferably a pharmaceutical solution comprising the hydrogel particles.

Also provided is the use of an aqueous solution, preferably an ink comprising the hydrogel particles for printing or as an additive for manufacturing applications.

Also provided is the use of a hydrogel particle or an aqueous solution as described herein as an in vitro cell culture supplement.

DETAILED DESCRIPTION OF THE INVENTION

Figure 23:
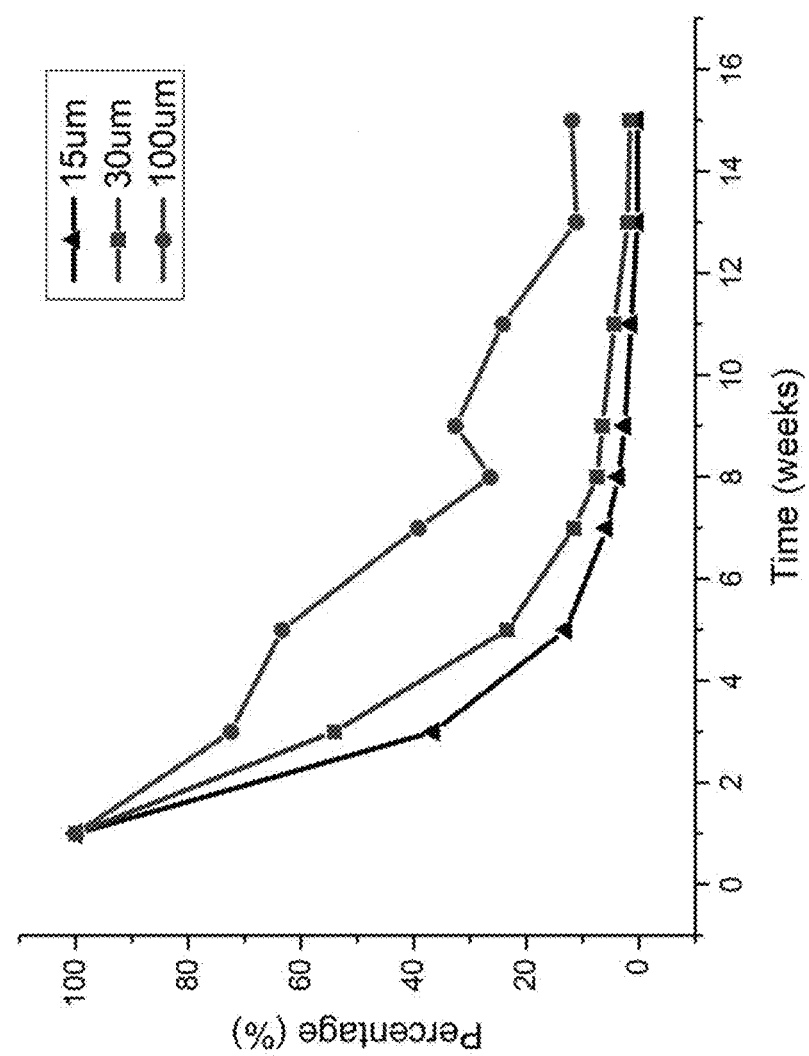
FIG. 23: Cells (15 um), 30 & 100 um microgels containing near-infrared labelled cells were intra-articularly injected in rats with healthy and osteoarthritic knees, Shown in the graph here is the retention of the NIR signal in healthy knees. Showing that the labelled cells in the gels are present up to at least 11 weeks.
Figure 24:
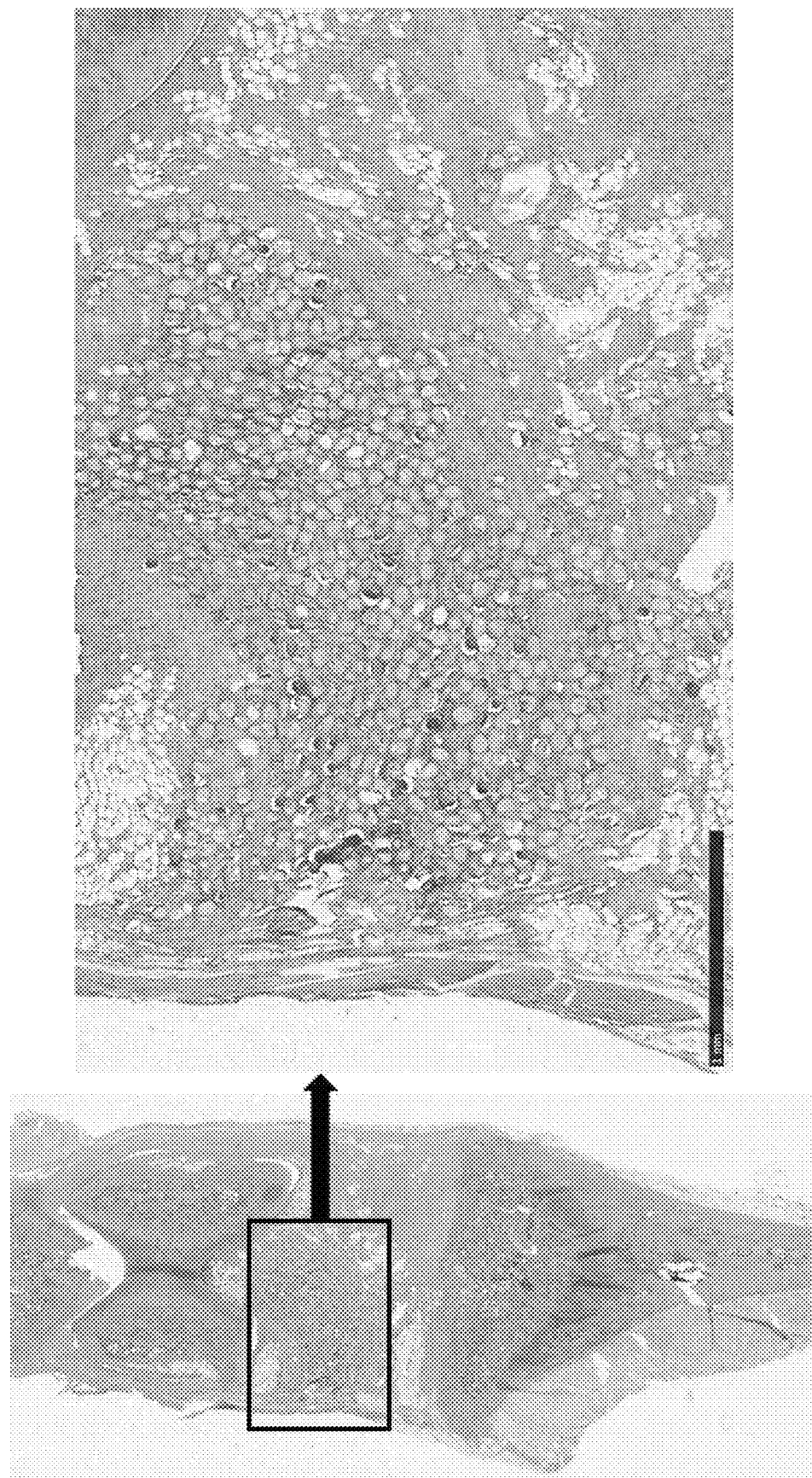
FIG. 24: Histological analysis of osteoarthritic knees shows that the gels are still present in large numbers after 12 weeks.

Polymeric hydrogels have proven to be very useful in a wide variety of applications such as slow release of encapsulated drugs and/or the shielding of encapsulated material to protect the material from the hostile environment in the host. Hydrogels of the invention can be shaped into discrete particles. The hydrogel particles are typically spherical, but other shapes are also possible, A hydrogel particle is preferably a spherical particle. A hydrogel particle described herein may have an average cross-sectional diameter of about 1 micrometer (μm) to 1000 μm. A hydrogel particle described herein preferably has an average cross-sectional diameter of about 2-1000 μm. The average cross-sectional diameter is preferably 3-1000 μm, preferably 5-1000 μm, preferably 10-1000 μm. In a particularly preferred embodiment the cross-sectional diameter is 1-250 μm, preferably 2-250 μm, preferably 3-250 μm, preferably 5-250 μm, more preferably 10-250 μm. In a particularly preferred embodiment the cross-sectional diameter is 1-100 μm, preferably 2-100 μm, preferably 3-100 μm, preferably 5-100 μm, more preferably 10-100 μm. In some embodiment the average diameter cross-sectional diameter is 5-500 μm. In a particularly preferred embodiment the cross-sectional diameter is 5-250 μm, preferably 10-200 μm. Hydrogel particles of the indicated size are easily injectable without significant shearing. Such hydrogel particles facilitate local accumulation at the injection site, particularly suitable for discrete injection sites such as a tumor, a site of inflammation, a synovial or other cavity, and within engineered tissues. The latter is often associated with inflammations and incorporation of particles of the invention in engineered tissues makes the implantation site a less hostile environment by the selective sequestering of one or more undesired biological molecules. The hydrogels are particularly suited for intra-articular injection. Hydrogel particles of the invention that have a diameter of more than 2 μm and preferably more than 3 μm are more efficiently retained in the joint after injection (Prada) et al, 2016: International journal of Pharmaceutics 498: 119-129. http://dx/doi.org/10.1016/j.ijpharm.2015.12.015). In a preferred embodiment the diameter is at least 5 µm, preferably at least 10 µm, more preferably at least 15, 30 or 100 µm (see FIG. 23 and FIG. 24).

The hydrogel particle can be hollow (i.e., a shell with a hollow core). The binding molecule may be present in the hollow cavity and is sufficiently immobilized by setting a mesh size of the first polymer network that prevents diffusion of the binding molecule to the outside of the particle and allows diffusion of the target molecule that is bound by the binding molecule. The polymer shell then prevents diffusion of antibodies and/or binding molecules, while allowing for diffusion of the molecules that are to be sequestered. This also effectively acts as a cytokine sink and relies on the spatial entrapment.

A hydrogel diameter is dependent on the hydration state (dry/swollen) and the solvent in which the hydrogel is measured. Diameters of hydrogel particles described herein are measured after incubation in a physiological aqueous saline solution (e.g. phosphate-buffered saline, pH7.4) until the hydrogel diameter has reached equilibrium, which is typically after ~1 to 24 hours. The cross-sectional diameter of hydrogel particles can be measured/determined using, for example, but not limited to, dynamic light scattering, laser diffraction, (digital) image analysis, sieve analysis, sedimentation methods, electrical impedance, or microscopy. For the present invention the cross-sectional diameters are preferably measured by microscopy in combination with digital image analysis, or as described in the examples. The average cross-sectional diameter of a collection of particles is preferably determined from the cross-sectional diameter of a representative random selection of particles in a collection. A representative selection typically comprises at least 100 particles but this can be extended when needed. The cross-sectional diameters of the particles in a collection are typically, but not necessarily, distributed as a bell-shaped curve (i.e., normal distribution), where the standard deviation from the mean determines the width of the bell-shaped curve. The distribution of the representative selection of hydrogel particles' cross-sectional diameters, herein referred to as the 'normalized size distribution', is defined as the standard deviation of the representative selection's cross-sectional diameter divided by the representative selection's average cross-sectional diameter. Normalized size distributions are smaller than 90%, preferably smaller than 75%, preferably smaller than 50%, preferably smaller than 25%, preferably smaller than 10%, preferably smaller than 5%. Collections of hydrogel particles having two different average cross-sectional diameters and/or two different normalized standard distributions can be combined. Such compositions are easily identified by plotting out the number of particles having certain cross-sectional diameters. Such plots can be made using any means for determining particles size but are preferably determined using microscopy in combination with digital image analysis.

Due to their minimal size, hydrogel particles as described herein offer improved diffusion rates of solutes, and direct compatibility with many standard microscopy techniques as compared to conventional macromaterials. Reducing the particle size has, for example, been demonstrated to improve the release kinetics from cell laden gels[19, 20]. On a different note, the in vivo biodistribution of injected hydrogel particles is associated with their size. Hydrogel particles larger than 5 µm are typically characterized by prolonged retention times, as they are not prone to rapid clearance from the site of injection via e.g., phagocytosis, lymphatic entrance, and intra- and extravasation[21, 22]

Hydrogel particle fabrication processes involves two steps: (1) dispersion of the hydrogel precursor (i.e., polymer) solution into discrete droplets and (2) gelation of the droplets through in situ crosslinking. Hydrogel precursor droplets can be formed via patterning or molding on/in solid substrates, emulsification in an (immiscible) liquid, or atomization in a gaseous phase. [23, 24] Hydrogel crosslinking can be categorized based on the molecular interaction between the polymers, which is of chemical or physical nature. Chemical interactions can be non-reversible, covalent bonds that are, e.g., being formed through complementary groups (e.g., Michael-type addition, radical polymerization, enzymatic cross linking or irradiation). [25]

Hydrogel particles described herein can be used in a method to interrupt, reduce or diminish (chronic) inflammatory, infectious, and other conditions such as genetic conditions by locally depleting the biological molecule(s) that drive/maintain these processes. The hydrogel particle comprises a porous stably crosslinked hydrogel network. Binding molecules that can bind one or more of the biological molecules, are immobilized in the polymer network (also referred to as the first polymer network). The internal location of the binding molecule(s) effectively shields the bound biological molecule from the local environment of the particle and thereby prevents its activity. Binding molecules can be linked to the polymer network in various ways. Host-guest chemistry is often used for binding molecules. Host-guest chemistry describes complexes that are composed of two or more molecules or ions that are held together in unique structural relationships by forces other than those of full covalent bonds. Host-guest chemistry encompasses the idea of molecular recognition and interactions through noncovalent bonding. Noncovalent bonding is critical in maintaining the 3D structure of large molecules, such as proteins and is involved in many biological processes in which large molecules bind specifically but transiently to one another. There are eight commonly mentioned types of non-covalent interactions: metal coordination bonds, hydrogen bonds, ionic bonds, van der Waals forces, ion-dipole, dipole dipole, π-π stacking and hydrophobic interactions. Non-limiting examples of host-guest chemistry is the biotin/avidin binding. The biotin can bind with high affinity to a member of the avidin family. This feature is advantageously used in many commercial and non-commercial settings. Examples are the classical biotin/streptavidin combination and the newer desthiobiotin and tetravalent neutravidin combination. Other examples of host-guest chemistry are readily available to the skilled person. In some embodiments the binding molecule is bound to the polymer network via host-guest chemistry. In other embodiments the binding molecule is covalently (chemically) bound to the polymer network. In yet further embodiments the binding molecule is not linked to a polymer but rather trapped in the polymer network. This may advantageously be used, for instance, for large binding molecules.

The binding molecule can be a binding peptide. Such peptides are typically small and able to bind the target with exceptional specificity. The peptide can be linked to a support or scaffold. Such a support or scaffold can but does not have to aid the binding of the peptide to the target. In such cases the support or scaffold can constrain the folding of the peptide and facilitates its binding function. Peptides can be linear or cyclic. Binding molecules such as aptamers and peptide aptamers are described in Reverdatto et al (2015; Curr Top Med Chem. 15(12): 1082-1101 and articles cited therein). A binding molecule can be an antibody or an antigen binding fragment thereof. It can be a single chain Fv fragment (scFv), a FAB-fragment, an anticalin, a so-called Nanobody™, a bicyclic peptide and the like. The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. An antibody fragment comprises at least the variable domain of an antibody. The binding molecule can also be a member of a ligand/receptor pair. As receptors are typically associated with cells and can bind soluble ligand it is preferred that the binding molecule is a receptor. Receptors that are normally membrane bound can often be modified by associating the extracellular part with an Fc tail or the like. Such modified proteins are typically easily attached to the polymer network.

The mesh size of a polymer network of a hydrogel can be determined in different ways. In the present invention mesh size is given to indicate the size of the molecules that can diffuse into the hydrogel particle. In some embodiments it is important that certain other molecules, or cells are prevented from diffusing into the hydrogel particle. In the present invention the mesh size is preferably characterized by the diffusion potential of molecules of a certain hydrodynamic radius. The hydrodynamic radius of a molecule can be determined using dynamic light scattering (DLS, Stetefeld et al, Biophys Rev. 2016 December; 8(4): 409-427. DOI: 10.1007/s12551-016-0218-6). Diffusion of a molecule with a given hydrodynamic radius into a polymer network can be monitored in different ways. One way in which this can be done is by creating two liquid compartments that are separated by the polymer network and adding a labelled molecule with a known hydrodynamic radius to one compartment of the network and letting the system reach (near) equilibrium with respect to the distribution of the labelled molecule. Examples of suitable systems with two compartments are capsules with a wall composed of the network (see for instance FIG. 13 and legend thereto) or two liquid containers separated by the polymer network. The presence of the label in the other compartment is a measure for the whether the molecule is able to diffuse through the polymer network. A molecule is said not to be able to diffuse through a network if less than 20% and preferably less than 10% of the maximal amount of molecule obtained with a 100 times larger mesh size, is detected on the other side of the network after equilibrium has reached. If equilibrium has not been reached after 24 hours, the percentage observed at 24 hours is taken as if equilibrium had been reached. In such cases the network has a mesh size that prevents diffusion of the molecule with the indicated hydrodynamic radius through the network. The network has a mesh size that does not allow the penetration of such molecules. The network has a size that prevents diffusion of a molecule with a given hydrodynamic radius into the polymer network.

A molecule is said to be able to diffuse through a network if more than 80% and preferably more than 90% of the maximal amount of molecule obtained with a 100 times larger mesh size, is detected on the other side of the network after equilibrium has reached. If equilibrium has not been reached after 24 hours, the percentage observed at 24 hours is taken as if equilibrium had been reached. In such cases the network has a mesh size that allows diffusion of the molecule into the network.

The comparative tests are, of course, performed under similar circumstances and with networks that are the same but for the molecular changes required to obtain the different mesh sizes.

The first polymer network can have an average mesh size that allows a molecule with a hydrodynamic radius of 1000 nanometer or less, preferably 500 nanometer or less, preferably 250 nanometer or less, more preferably 100 nanometer or less to diffuse into the first polymer network. The first polymer network preferably has an average mesh size that allows a molecule with a hydrodynamic radius of 50 nanometer or less, preferably 20 nanometer or less, preferably 10 nanometer or less, more preferably 5 nanometer or less, more preferably 4 nanometer or less to diffuse into the first polymer network. When antibody capture or sequestration is desired, the average mesh size is preferably more than the average size of IgG, preferably more than 15 nanometer, preferably 20 nanometer. If antibodies are to be kept out of the particle it is preferred that the average mesh size is smaller than the typically antibody. Preferably 15 nanometer or smaller, preferably 12, 11 or 10 nanometer or smaller. Preferably 10 nanometer.

The first polymer network can have an average mesh size that prevents diffusion of a molecule with an average hydrodynamic radius of more than 1000 nm to diffuse into the first polymer network, preferably the mesh size prevents diffusion of a molecule with an average hydrodynamic radius of more than 500 preferably more than 250, preferably more than 100, preferably more than 50, preferably more than 20, preferably more than 10, preferably more than 5, preferably prevents diffusion of a molecule with an average hydrodynamic radius of more than 4 nanometer into the first polymer network. Networks that restrict access of larger molecules are typically active for a longer period of time. Networks that restrict access of larger molecules are typically more resistant to wear are tear in the body.

The mesh size of the first polymer network can be determined by measuring the diffusion of molecules with a known average hydrodynamic radius. In the context of the present invention the polymer network of the hydrogel has an average mesh size of at least 1000 nanometer if it allows a molecule with a hydrodynamic radius of 1000 nanometer or less to diffuse into the polymer network. The polymer network of the hydrogel has an average mesh size of at least 500 nanometer if it allows a molecule with a hydrodynamic radius of 500 nanometer or less to diffuse into the polymer network, etc.

In the context of the present invention the polymer network of the hydrogel has an average mesh size of 1000 nm or less if it prevents diffusion of a molecule with an average hydrodynamic radius of more than 1000 nm to diffuse into the first polymer network. The polymer network of the hydrogel has an average mesh size of 100 nm or less if it prevents diffusion of a molecule with an average hydrodynamic radius of more than 100 nm to diffuse into the polymer network etc.

An average hydrogel mesh size can also be determined mechanically or on the basis of the molecule release (see for instance Grassi et al., 2009 Molecules Vol 14 pp 3003-3017: doi:10.3390/molecules14083003). Yet another way of determining pore size is theoretically using the so-called "single-pore-radius" model described by Russell (2005: Ind. Eng. Chem. Res. Vol 44: pp 8213-8217). In this context the hydrogel as described herein has a mesh size that is solely determined by the new method, i.e. not by measuring whether a particle with a given hydrodynamic radius can diffuse into the network. In such cases is provided a hydrogel particle that has an average cross-sectional diameter in the range of 1 micrometer (μm) to 1000 μm, wherein the particle comprises a first polymer network with an average mesh size of 1000 nanometer or less, preferably 500 nanometer or less, preferably 250 nanometer or less, more preferably 100 nanometer or less, preferably 50 nanometer or less, preferably 20 nanometer or less, preferably 10 nanometer or less, more preferably 5 nanometer or less, more preferably 4 or less preferably as determined mechanically according to Grassi et al (supra) or according to the "single-pore-radius" model according to Russel et al (supra) and in which the particle comprises a binding molecule that is immobilized by the polymer network. The first polymer network preferably has an average mesh size of 1000 nanometer, preferably 500 nanometer, preferably 250 nanometer, more preferably 100 nanometer, preferably 50 nanometer, preferably 20 nanometer, preferably 10 nanometer, more preferably 5 nanometer, more preferably 4. Yet another way to define a hydrogel mesh size is by whether molecules with a given molecular weight in kilodalton (kDa) are able to diffuse into the polymer network. A correlation for the radius of particles and the molecular weight of the particles is given with the formula $Rmin=0.066\times M^{1/3}$ (Erickson 2009, Biol. Proced Online 11: 32-51. Do: 10.1007/s12575-009-9008-x). In the formula the variable Rmin stands for the minimal radius and M stands for the molecular weight in daltons. The present invention thus also provides a hydrogel particle that has an average cross-sectional diameter in the range of 1 micrometer (μm) to 1000 μm, wherein the particle comprises a first polymer network with an average mesh size that allows the diffusion of a molecule of not more than 430 gDa (gigadalton), preferably not more than 54 gDa, preferably not more than 6.8 gDa, preferably not more than 435 MDa (megadalton), preferably not more than 54 MDa, preferably not more than 3.5 MDa, preferably not more than 435 kDa (kilodalton), preferably not more than 54 kDa, preferably not more than 28 kDa.

In a preferred embodiment is provided a hydrogel particle that has an average cross-sectional diameter in the range of 1 micrometer (μm) to 1000 μm, wherein the particle comprises a first polymer network with an average mesh size that allows the diffusion of a molecule of not more than 900 kDa, not more than 320 kDa, not more than 200 kDa, not more than 180 kDa, preferably not more than 150 kDa. These are the molecular weight of respectively the immunoglobulines (Ig) M, IgA, IgE, IgD and IgG. An advantage of such particles is that the binding molecule and captured biological molecule is effectively shielded from the mentioned antibody species. The effect of an inadvertent host antibody versus particle (content) response, if any, is less for the respective antibodies/mesh size.

The first polymer network in a hydrogel particle as described herein preferably has a mesh size that allows diffusion of biological molecules with a molecular weight of 100 kDa, preferably 70 kDa more preferably around 15 kDa. Most cytokines have a molecular weight of less than 70 kDa.

A hydrogel particle preferably comprises cross-linked hydrogel polymers. Crosslinking is the process of joining two or more polymer chains. Both chemical and physical crosslinking exists. In addition, both natural polymers such as proteins or synthetic polymers with a high affinity for water may be used as starting materials when selecting a hydrogel. Different crosslinking methods can be implemented for the design of a hydrogel. By definition, a crosslinked polymer gel is a macromolecule that solvent will not dissolve Due to the polymeric domains created by crosslinking in the gel microstructure the gel acquires more chemical stability. Various crosslinking methods are known in the art such as but not limited to chemical cross-linking, photo-crosslinking (typically UV), protein interaction, hydrogen bonds etc.

The cross-linking moiety is preferably a phenolic compound. Methods are available for the enzyme-mediated covalent coupling of a phenolic compound to another phenolic compound using a catalyzer (i.e., a peroxidase enzyme such as, but not limited to, horseradish peroxidase) and an oxidizer (e.g., hydrogen peroxide), where the phenolic compounds are characterized by the presence of at least one hydroxyl-substituted aromatic ring system, including, but not limited to phenol conjugated macromolecules, phenol conjugated small molecules, phenol, tyramine, tyrosine, polyphenol, p-coumaric acid, ubiquinol, vitamin E, catechol, ferulic acid, capsaicin, eugenol, resorcinol, genistein, epicatechin, pyrogallol, gallic acid, propylgallate, penta G-D-glucose, bisphenol A, butylated hydroxytoluene, cresol, estradiol, guaiacol, 4-nonylphenol, orthophenyl phenol, trinitrophenol, phenolphthalein, propofol, serotonin, adrenalin, thymol, xylenol, diethylstilbestrol, L-DOPA, methyl salicylate, salicylic acid, 2-benzyl-4-chlorophenol, 4-chloro-3,5-dimethylphenol, butylated hydroxyl anisole, resorcinol, 4-hexylresorcinol, hydroquinone, 1-naphtol, calixarenes, but also peptides, synthetic or natural polymers, fluorescent dyes, drugs, DNA, proteins, lipoproteins, antibodies, single-domain antibodies, aptamers, nanobodies, and all other molecules that naturally contain and/or are modified with a phenolic group (i.e., a hydroxyl-substituted aromatic ring system), or combinations thereof. Preferably crosslinking is done with a tyramine group.

A great number of polymers can be used to prepare hydrogels. In the present invention the polymer is a biocompatible polymer. The polymer is preferably one or more of dextran; hyaluronic acid; and poly-ethylene glycol (PEG).

A biocompatible hydrogel polymer is a hydrogel polymer that has the ability to be in contact with a living system without producing a significant adverse effect. Biocompatible in this context means that a material does not elicit a significant pathological response of the body against said biomaterial or that said material is not harmful to the patient. Polymer hydrogels have been used for quite some time and are amongst others reviewed in Laftah et al (2011: Polymer Hydrogels: A Review, Polymer-Plastics Technology and Engineering, 50:14, 1475-1486), Preferred examples hydrogel polymers are described in U.S. Pat. No. 8,647,271; US20060257488; WO1999015211; WO 2011/049449; WO2011/059325 WO2013/073941 and U.S. Pat. No. 8,440, 231. The hydrogel polymer can be a co-polymer of hyaluronic acid (HA) grafted with a dextran-tyramine (Dex-TA) conjugate. The Dex-TA conjugate preferably has a degree of substitution (DS), defined as the number of conjugated tyramine moieties per 100 anhydroglucose rings, of 5-25. The dextran chain in said Dex-TA conjugate preferably has an average molecular weight of 5-80 kDa. The hydrogel polymer can be a composition comprising a Dex-TA conjugate and a conjugate selected from the group consisting of collagen-tyramine; chitosan-tyramine; chitosan-phloretic acid- and gelatin-tyramine and hyaluronic acid-tyramine. The hydrogel polymer is preferably a conjugated hyaluronic acid, chitosan, dextran, hyaluronic acid, heparin or heparan starch; poly lactic acid (PLA), a polyethylene glycol (PEG), a polyalkyleneoxide-polyalkyle-terephtalate block copolymer, (preferably polyethylene oxide-polybutylene terephtalate block copolymers), poly-L-lactic acid (PLLA), polyglycolic lactic acid (PGLA), polyglycolic acid (PGA), poly(amido amine)s, poly(caprolactone), polyethylene; alginate, a Poly-N-isopropylacrylamid or copolymers of polyethylene glycol terephthalte and polybutylene terephthalate (PEGT-PBT, or Polyactive®). The conjugation is preferably with a cross-linking group, preferably at least one tyramine preferably more.

A hydrogel particle as described herein preferably comprises a dextran-tyramine hydrogel; a hyaluronic acid-tyramine hydrogel; a PEG-tyramine hydrogel or a combination thereof.

The hydrogel can be a chemically stable hydrogel (Hoffman, 2012: Advanced Drug Delivery Reviews 64: 18-23). Hydrogels are called permanent or chemical gels when they are covalently-crosslinked networks.

The invention also relates to aqueous solutions comprising the hydrogel particles. The solution is preferably an injectable solution, i.e. a solution that can be passed through a hollow needle that is used to administer fluids to the body of a human in the medical profession. The needle can be hypodermic needle which is a thin, hollow tube with a sharp tip that contains a small opening at the pointed end. Needle free systems also exist and these also use injectable aqueous solutions as described herein.

The affinity of the binding molecule for the biological molecule does not have to be extremely high. Bound molecule is effectively prevented from diffusing out of the particle when it is inadvertently released from the binding molecule as it is quickly rebound to the binding molecule or bound to another available binding molecule.

Binding can be expressed in terms of specificity and affinity. The specificity determines which antigen or epitope thereof is specifically bound by the binding domain. The affinity is a measure for the strength of binding to a particular target comprising the antigen or epitope. Specific binding typically requires a certain affinity for the epitope containing antigen. In the context of a binding molecule as used herein the binding is specific in the sense that the epitope containing antigen is bound with an affinity (Kd) of at least $1\times10e-6$ M, more preferably $1\times10e-7$ M, $1\times10e-8$ M, more preferably higher than $1\times10e-9$ M. A binding molecule preferably binds the epitope containing antigen with an affinity (Kd) of $1\times10e-9$ M-$100\times10e-9$ M. A binding molecule does typically not bind significantly to antigens that do not have the epitope. Binding to such molecules is typically less than the Kd for the epitope containing antigen. Typically such non-specific binding is with a strength of less than $1\times10e-6$ M if any. A binding molecule can specifically bind other antigens as long as such antigens contain the epitope.

The binding molecule preferably binds to a biological molecule. The molecule that is bound by the binding molecule is preferably a peptide or a protein. The biological molecule, peptide or protein is preferably soluble in a bodily fluid. Such molecules can diffuse into the polymer network of the particles. The peptide or protein can be a released part of a matrix such as a pro-inflammatory matrix degradation products in the joint. In a preferred embodiment the protein is a cytokine, a soluble antigen or an auto-antibody. In a preferred embodiment the protein is a matrix degradation product. Such products can be pro-inflammatory.

In a preferred embodiment the binding molecule is specific for a cytokine. A cytokine is a member of a family of small proteins (~5-70 kDa) that are important in cell signaling. Their release has an effect on the behavior of cells around them. A cytokine can be involved in autocrine signaling, paracrine signaling and endocrine signaling. Preferred cytokines include chemokines, interferons, interleukins, lymphokines, and tumor necrosis factors but generally not hormones or growth factors. Cytokines can be produced by a broad range of cells, including immune cells like macrophages, B lymphocytes, T lymphocytes and mast cells, as well as endothelial cells, fibroblasts, and various stromal cells; a given cytokine may be produced by more than one type of cell. A cytokine typically acts through a receptor, and is especially important in the immune system. A cytokine can, for instance modulate the balance between humoral and cell-based immune responses. A preferred cytokine is a cytokine that is involved with joint-inflammation. The cytokine is preferably TNFalpha, IL1beta, oncostatinM, IL-6, IL-4, IL-10, IL-17, IL-8, an alarmins like S108 or S109.

The binding molecule can be specific for a growth factor or a growth factor antagonist for instance a Wnt molecule a Wnt-antagonist, such as preferably DKK1, FRZB or sclerostin, a BMP, a BMP antagonist such as preferably Noggin, Gremlin or Chordin, a TGFbeta, a FGF or NGF.

The binding molecule ensures that the biological molecule is bound in the particle, preferably in the internal network of the hydrogel. Bound biological molecules are effectively prevented from binding to binding partners that cannot penetrate the particle either due to its size or due to limited mobility of binding partners such as cellular receptors. The binding of the binding molecule to the biological molecule does therefore not have to be to a neutralizing epitope on the biological molecule. The binding can be to a neutralizing epitope such that when the binding molecule is bound the biological molecule cannot functionally bind to a binding partner such as a receptor also when the binding molecule is not or no longer in the internal network of the hydrogel. It is preferred that the binding molecule binds a neutralizing epitope on the biological molecule. This feature ensures that when the particle is inadvertently partly or completely degraded prior to inactivation of the biological molecule, the activity of the biological molecule is still inhibited by the bound binding molecule.

The binding molecule is preferably physically or chemically linked to the polymer network. Physical linkage is possible in many ways. For instance by providing the binding molecule with a functional group which can directly or indirectly bind to a polymer in the network. The binding can be affinity binding such as the exemplary biotin/avidin binding or antibody binding. The binding can also be a chemical bond such as covalent coupling. Peptide/protein linkage chemistry is presently highly evolved and many different methods are available, non-limiting examples are amine-reactive crosslinking chemistry and carbodiimide crosslinker chemistry or maleimide chemistry targeting SH-groups. Particularly common methods utilize the molecule N-hydroxysuccinimide (NHS) or similar molecules such as sulfo-NHS. Such methods are often used in 1-Ethyl-3-(3-dimethylaminopropyl)carbodiimide (EDS) coupling methods. Other reactive groups that can be targeted for cross-linking are the sulfhydryls (—SH) and carbonyl (CHO). The latter can be created by oxidizing carbohydrate groups in glycopeptides or glycoproteins.

Hydrogel crosslinking can be based on the molecular interactions between the polymers, which can be of a chemical or physical nature. Chemical interactions are formed by chemically reacting moieties yielding a permanent covalent bond. Traditionally, chemical hydrogels are formed via the radical polymerization of monomers with reactive end groups using a crosslinking agent [Wichterle, O. and LIM, D. (1960) Hydrophilic Gels for Biological Use. Nature 185 (4706), 117-118]. Radical-based crosslinking can be but does not have to be associated with cytotoxicity. Radicals can be efficiently consumed through enzymatic crosslinking, which is, e.g., used in peroxidase-mediated crosslinking of phenolic moieties [Henke, S. et al. (2016) Enzymatic Crosslinking of Polymer Conjugates is Superior over Ionic or UV Crosslinking for the On-Chip Production of Cell-Laden Microgels. Macromol Biosci 16 (10), 1524-1532]. Expediently, radical-based single-cell encapsulation has also been achieved in a cytocompatible manner by adding radical-forming photo-initiator to the immiscible oil phase rather than the cell-laden hydrogel precursor phase. This strategy enabled microgel crosslinking in an outside-in manner, thereby minimizing the exposure of the encapsulated cell to cytotoxic radicals [11]. Physical bonds are reversible (i.e., non-covalent) and are, amongst others, based on entanglements, electrostatic (i.e., ionic or hydrogen bonds), van der Waals, hydrophobic interactions, or a combination thereof, such as in host-guest interactions.

Figure 3:
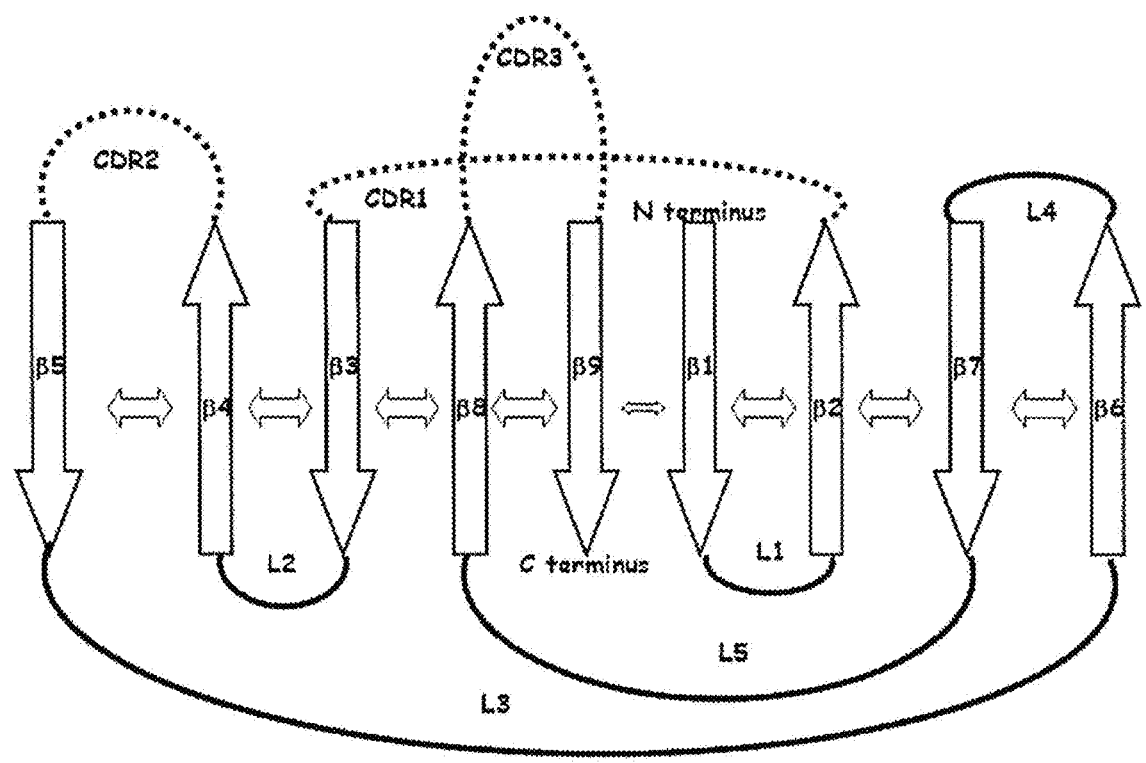
FIG. 3: A schematic representation of a llama VHH. VHH is organized in 9 anti-parallel β-stands connected with loops. Three of these loops form the complementary determining regions (CDR1, CDR2 and CDR3). Loops L1, L2, L3 and L5 are located away from the CDRs and are suited for the introduction of glycosylation sites and incorporation of glycosyl groups without interference with binding of the VHH to its antigen. Loop L4 is located close to the CDRs and its manipulation may affect the binding of the VHH to its antigen.
Figure 3:
Figure 3:
Figure 3:
Figure 3:

The binding molecule is preferably a binding protein, preferably a single-domain antibody. The single domain antibody is preferably a variable domain of a single chain heavy chain only antibody of a camelid or cartilaginous fish. (also referred to as VHH and VNAR respectively). The binding molecule is preferably a VHH or a VNAR. These terms refer to the single heavy chain variable domain antibodies devoid of light chains. Preferably a VHH or VNAR is of an antibody of the type that can be found in Camelidae or cartilaginous fish which are naturally devoid of light chains. The VHH and VNAR are presently generated artificially and selected from large libraries having different VHH or VNAR like molecules. A VHH or VNAR can presently also be produced synthetically. The term VHH is presently sometimes also used to refer to heavy chain variable domain of another species that is modified to function in the absence of a functional light chain. A VHH or VNAR is preferably chemically or physically linked to the polymer of the hydrogel, preferably via a chemical crosslink via a functional group that is present on or provided to the VHH or VNAR. For VHH said functional group is preferably a glycosyl group present at one of the VHH's short loops 1, 2, 3, 5 (see FIG. 3 and description thereof). The functional group can also be at another part of the VHH for instance in the C-terminal end of the VHH, preferably a substitution of one or more of the last 10 amino acids of the C-terminus. The functional group can also be added as a peptide to the C-terminal end of said VHH. The functional residue can be a Cys or Met residue, which will bind to the biomaterial directly via S—S bridges or amine groups. The functional group can be a Tyramine-azide or Tyramine-alkyn, capable of chemical cross linking to respective residues in a polymer through NHS chemistry.

Hydrogel particles can have a tunable porosity which allows the diffusion of a large variety of molecules in a size range of a few Daltons (Da) up to 150 kDa. Cytokines typically have a molecular weight size range of 5 kDa-70 kDa and which can easily enter the hydrogel via diffusion. Once entered in the hydrogel, they are captured by a specific affinity antibody fragment. Biological molecules that are not a target for the binding molecule is free to diffuse out of the particle. A high density of binding molecules such as antibody fragments and the associated avidity effectively prevents targets from leaving the particle once has entered and was bound to the hydrogel polymer network. Other cytokines for which no high affinity antibody fragments are present can freely diffuse in and out the hydrogel network. Compared to hemoadsorption using e.g. CytoSorb at least some methods as described herein clearly distinguish themselves by their high selectivity and specificity in capturing specific biological molecules such as cytokines and the ability to neutralize only molecules for which binding molecules are present. CytoSorb or comparable technologies cannot make this distinction and depletes serum from all cytokines because these technologies rely on non-specific interactions instead of the specific binding molecules used in the invention.

Figure 1:
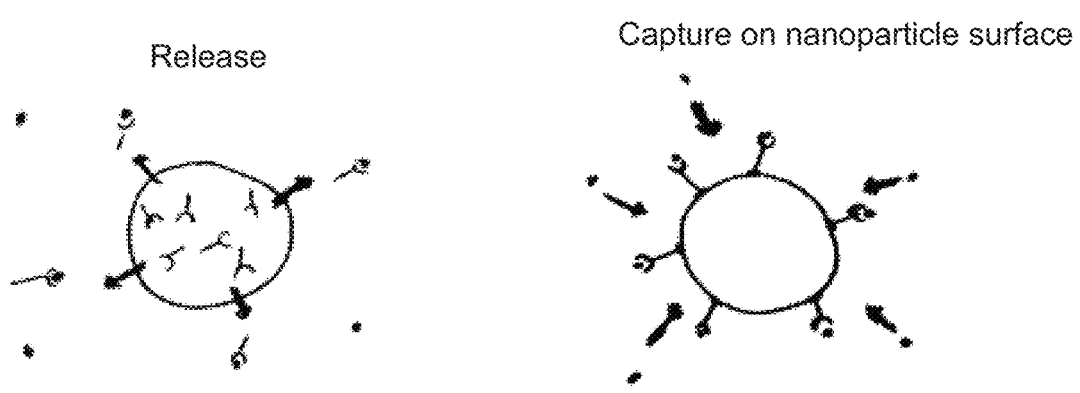
FIG. 1: Schematic drawing of hydrogel particles in the prior art. The left hand panel depicts the organization of binding molecules in a hydrogel particle intended for controlled release of the binding molecule. The right hand panel depicts binding molecules exposed on the surface of nanoparticles intended to bind and present antigen to the outside.
Figure 2:
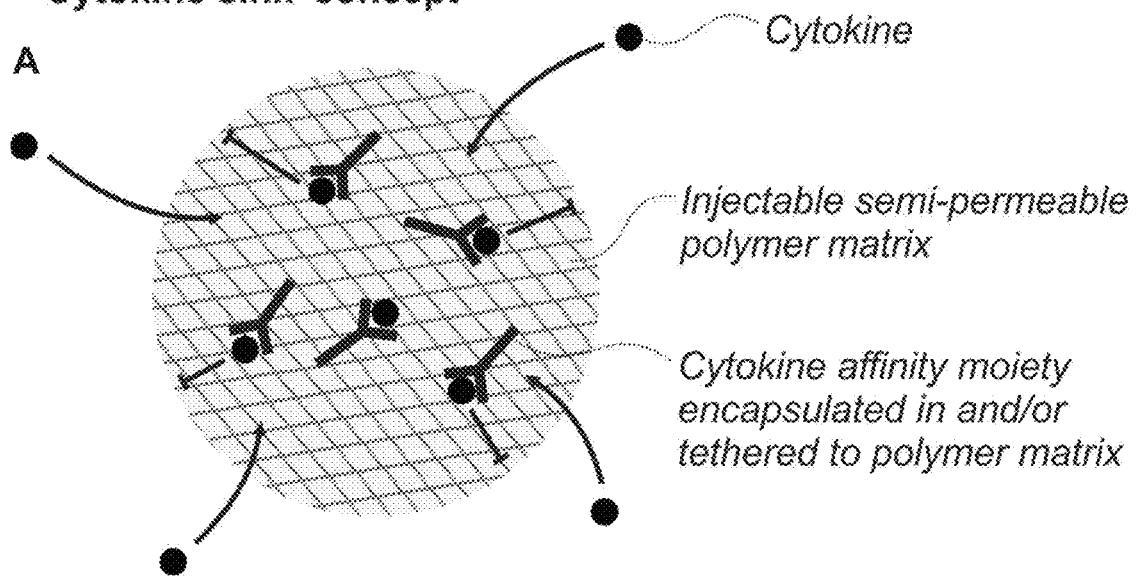
FIG. 2: A) schematic drawing of an embodiment of a hydrogel particle of the invention where a binding molecule is immobilized in the interior of the hydrogel. B) schematic drawing of an embodiment of a hydrogel particle of the invention where a binding molecule is immobilized in the interior of the hydrogel and wherein the hydrogel is surrounded by a second hydrogel that does not contain the binding molecule and has a mesh size that functions as a sieve allowing target molecules to enter the particle and that prevents larger molecules from entering the particle.
Figure 2:
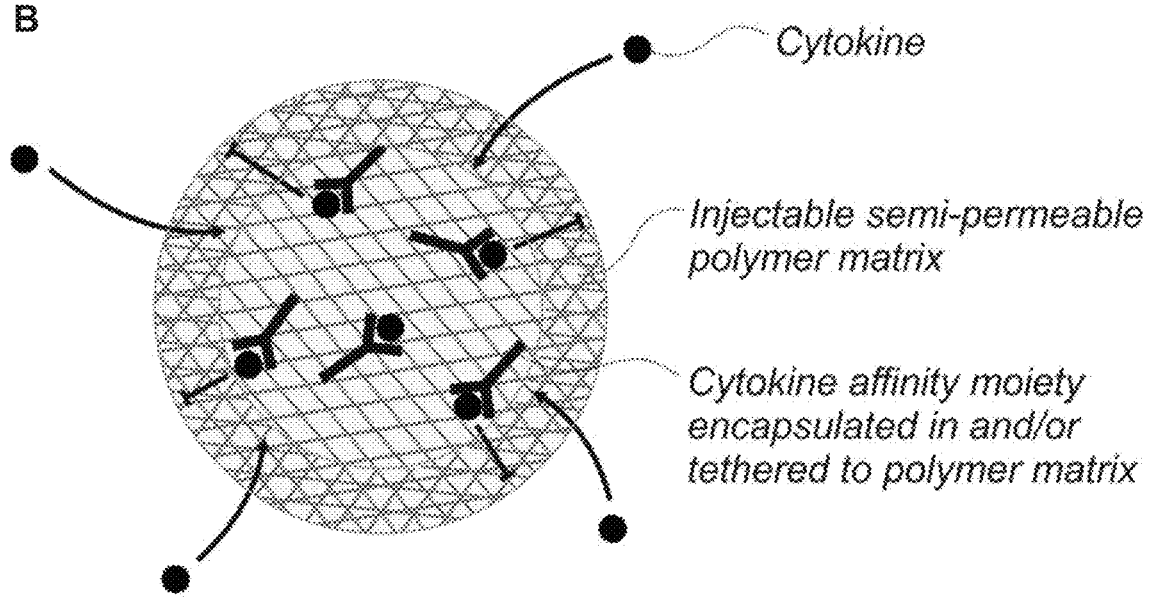

Hydrogel particles as described herein can function as so-called cytokine sinks. The hydrogels are porous injectable microparticles that enable the sequestration and/or depletion of (harmful) biological molecule of interest, while protecting the binding molecule against the harmful in vivo conditions (e.g. of an inflamed tissue), as depicted in the FIG. 2. The semi-permeable hydrogel also increases the avidity against cytokines of interest, as it provides a highly concentrated microenvironment of antibodies that cannot be reached by extracellular matrix associated proteins, cells and depending on the mesh size, non-specifically interacting proteins (e.g. endogenous antibodies/cytokine-binding proteins) that are larger than the hydrogels mesh size. An advantage of the particles of the present invention is that the particles are micrometer-sized and larger. This facilitates the prolonged presence of the particles when compared to other particles. Nanoparticles, for instance are typically more rapidly cleared and/or phagocytosed.

A biocompatible hydrogel polymer is a hydrogel polymer that has the ability to be in contact with a living system without producing a significant adverse effect. Biocompatible in this context means that a material does not elicit a significant pathological response of the body against said biomaterial or that said material is not harmful to the patient. Polymer hydrogels have been used for quite some time and are amongst others reviewed in Laftah et al (2011: Polymer Hydrogels: A Review, Polymer-Plastics Technology and Engineering, 50:14, 1475-1486). Preferred examples hydrogel polymers are described in U.S. Pat. No. 8,647,271; US20060257488; WO1999015211; WO 2011/049449; WO2011/059325 WO2013/073941 and U.S. Pat. No. 8,440,231. The hydrogel polymer can be a co-polymer of hyaluronic acid (HA) grafted with a dextran-tyramine (Dex-TA) conjugate. The Dex-TA conjugate preferably has a degree of substitution (DS), defined as the number of conjugated tyramine moieties per 100 anhydroglucose rings of 5-25. The dextran chain in said Dex-TA conjugate preferably has an average molecular weight of 5-80 kDa. The hydrogel polymer can be a composition comprising a Dex-TA conjugate and a conjugate selected from the group consisting of collagen-tyramine; chitosan-tyramine; chitosan-phloretic acid and gelatin-tyramine. The hydrogel polymer is preferably a conjugated hyaluronic acid, chitosan, dextran, hyaluronic acid, heparin or heparan starch; poly lactic acid (PLA), a polyalkyleneoxide-polyalkyle-terephtalate block copolymer, (preferably polyethylene oxide-polybutylene terephtalate block copolymers), polyethylene Glycol (PEG), poly-L-lactic acid (PLLA), polyglycolic lactic acid (PGLA), polyglycolic acid (PGA), poly(amido amine)s, poly(caprolactone), polyethylene; alginate, a Poly-N-isopropylacrylamid or copolymers of polyethylene glycol terephthalte and polybutylene terephthalate (PEGT-PBT, or Poly-active®). The conjugation is preferably with a cross-linking group, preferably a tyramine.

Hydrogel particles as described herein can comprise a second polymer network that surrounds said first polymer network, which second polymer network is devoid of said binding molecule. The second polymer network, sometimes also referred to as shell, surrounds the first polymer network and can shield it from molecules, particles and cells that cannot diffuse through the second polymer network. In case where the second polymer network has a selective mesh size the first polymer network can have a larger mesh size to reduce diffusion times, if such is desired. The second polymer network can thus have a mesh size that is the same or smaller than the mesh size of the first polymer network.

For hydrogel particles comprising a first and a second polymer network as described herein it is preferred that the second polymer network has an average mesh size that is the same or smaller than the mesh size of the first polymer network. In such cases the first polymer network preferably has a mesh size that allows a molecule with a hydrodynamic radius of 1000 nanometer or less to diffuse into the first polymer network and the second polymer network has a mesh size that prevents diffusion of a molecule with an average hydrodynamic radius more than 1000 nanometer to diffuse into the second polymer network. Preferably the mesh size of the second polymer network prevents diffusion of a molecule with an average hydrodynamic radius of more than 500, preferably more than 250, preferably more than 100, preferably more than 50, preferably more than 20, preferably more than 10, preferably more than 5 into the second polymer network. In a preferred embodiment the second polymer network has a mesh size that prevents diffusion of a molecule with an average hydrodynamic radius of more than 4 nanometer into the second polymer network. The first polymer network can of course also have a mesh size that is smaller than a mesh size that allows a molecule with a hydrodynamic radius of 1000 nanometer or less to diffuse into the first polymer network. Examples are mesh sizes that allow a molecule with a hydrodynamic radius of 500 or less, 250 or less, 100 or less, 50 or less, 20 or less, 10 or less, 5 or less, and preferably 4 nanometer or less to diffuse into the first polymer network. Hydrogel particles that have an average cross-sectional diameter in the range of 1 micrometer (µm) to 1000 µm, wherein the particle comprises a first polymer network with an average mesh size of 1000 nanometer or less, preferably 500 nanometer or less, preferably 250 nanometer or less, more preferably 100 nanometer or less, preferably 50 nanometer or less, preferably 20 nanometer or less, preferably 10 nanometer or less, more preferably 5 nanometer or less, more preferably 4 or less preferably as determined mechanically according to Grassi et al (supra) or according to the "single-pore-radius" model according to Russel et al (supra) and in which the particle comprises a binding molecule that is immobilized by the polymer network can also have a second polymer network that surrounds said first polymer network, which second polymer network is devoid of said binding molecule. The second polymer network preferably has an average mesh size that is smaller than the mesh size of the first polymer network. The second polymer network preferably has a mesh size of 1000 nanometer or less, preferably 500 nanometer or less, preferably 250 or less, preferably 100 or less, preferably 50 or less, preferably 20 or less, preferably 10 or less, preferably 5 nanometer or less.

Hydrogel particles that have an average cross-sectional diameter in the range of 1 micrometer (µm) to 1000 µm, wherein the particle comprises a first polymer network with an average mesh size that allows the diffusion of a molecule of not more than 430 gDa (gigadalton), preferably not more than 54 gDa, preferably not more than 6.8 gDa, preferably not more than 435 MDa (megadalton), preferably not more than 54 MDa, preferably not more than 3.5 MDa, preferably not more than 435 kDa (kilodalton), preferably not more than 54 kDa, preferably not more than 28 kDa can also have a second polymer network that surrounds said first polymer network, which second polymer network is devoid of said binding molecule. The second polymer network preferably has an average mesh size that is smaller than the mesh size of the first polymer network. The second polymer network preferably has a mesh size that allows the diffusion of a molecule of not more than 430 gDa (gigadalton), preferably not more than 54 gDa, preferably not more than 6.8 gDa, preferably not more than 435 MDa (megadalton), preferably not more than 54 MDa, preferably not more than 3.5 MDa, preferably not more than 435 kDa (kilodalton), preferably not more than 54 kDa, preferably not more than 28 kDa.

The second polymer network preferably has a thickness of 1 nm-450 micrometer; 1 nm-50 micrometer; 1 nm-5 micrometer; 1 nm-500 nm or 1 nm-50 nm. The second polymer network preferably has a thickness of 5 nm-450 micrometer; 25 nm-50 micrometer; 100 nm-5 micrometer en 100 nm-500 nm. The thickness is preferably 0.5-100 micrometer, preferably 0.5-50 micrometer, more preferably 0.5-20 micrometer.

The second polymer network can comprise a targeting moiety or a biological compartment retention molecule. The second polymer network has an inward directed surface at the first polymer network and an outward directed surface on the opposite side. The targeting moiety or biological compartment retention molecule, are preferably immobilized at the outward directed surface. In a preferred embodiment the targeting moiety or biological compartment retention molecule is chemically or physically linked to the second polymer network. Means and methods for linking a molecule to a polymer network are described elsewhere herein. A targeting moiety is preferably a binding molecule with a specificity for a proteinaceous molecule that is present at and chemically or physically linked to or near a site of interest. The targeting moiety is preferably a binding molecule with a specificity for a cellular receptor or a chemically or physically linked matrix protein. The targeting moiety is preferably specific for a proteinaceous molecule that is present in and chemically or physically linked to a synovial cavity. Examples of such targeting moieties are, but not limited to, an antibody or an antigen binding fragment thereof. It can be a single chain Fv fragment (scFv), a FAB-fragment, an anticalin, a so-called nanobody, a bicyclic peptide and the like. The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. An antibody fragment comprises at least the variable domain of an antibody. The binding molecule can also be a member of a ligand/receptor pair.

The aqueous solution comprising hydrogel particles as described herein is preferably a polymerizable solution. This is for instance useful in bioinks (see for instance Kamperman et al (Adv. Health. Mater. 6; 2017; 1600913). Other uses include but are not limited to improving the retention of the hydrogel particles at a certain location in the body. Furthermore polymerizable aqueous solution can be used in engineered tissue and can make a hostile inflammatory environment more friendly for the implant (engineered tissue) by putting one or more sinks into the engineered tissue.

The aqueous solution as described herein is preferably a pharmaceutical solution, preferably a pharmaceutical composition comprising hydrogel particles as described herein and a pharmaceutically acceptable carrier, or excipient. The aqueous solution, the pharmaceutical solution or pharmaceutical composition is preferable an injectable solution or composition. An injectable solution is a solution that can be passed through a hollow needle that is used to administer fluids to the body of a human in the medical profession. The needle can be hypodermic needle which is a thin, hollow tube with a sharp tip that contains a small opening at the pointed end. It is commonly used with a syringe, a hand-operated device with a plunger, to inject substances into the body. An aqueous solution is a solution in which the solvent is water. The aqueous solution is preferably a physiological solution (i.e. comprising an osmolarity that is compatible with life. Often physiological salt solution is used (9 g of salt per liter (0.9%) solution). When buffered with a phosphate buffer it is known as phosphate buffered saline or PBS.

The aqueous solution acts as the cytokine sink as to remove deplete molecules/cytokines from the surrounding environment of implants (making a hostile environment less hostile by incorporating the cytokine sink microgels into an (distinct/secondary) ink/biomaterial)!

The invention also provides a hydrogel particle, a pharmaceutical solution, or a pharmaceutical composition as described herein for use in the treatment of a patient with an over-active immune system, a cancer, or over-active hormone and/or cytokine producing cells, preferably in the treatment of inflammation, preferably in the treatment of joint-inflammation. The patient with an over-active immune system can be an auto-immune disease patient, a patient with an inflammation, a microorganism induced immune response (e.g. bacteria or yeast), trauma induced immune response (acute stress causes inflammation), tissue degeneration induced immune response (breakdown products can induce inflammation) and the like.

An overactive immune system is a condition when the immune system starts killing cells and tissues inside the body or a condition wherein the immune response is in "cytokine storm" mode which primary symptoms are high fever, swelling, redness, extreme fatigue, and nausea. In some cases the immune reaction will be fatal. While an effective immune system is necessary to ensure good health, an overactive immune system is a threat in itself. The immune system keeps our body protected against any harmful viruses and bacteria. However, there are times when our immune system can go awry and start attacking our own body tissues and cells. This can result in various auto-immune diseases, various shock symptoms and allergies. The American autoimmune related disease association maintains a list of auto-immune disease. Typical for most of these is the (local) presence of pro-inflammatory cytokines or soluble allergens or antigens. One or more of these factors can be depleted from the locality by injecting a hydrogel particle, a pharmaceutical solution, or a pharmaceutical composition as described herein and having one or more binding molecules specific for one or more of these factors at the affected locality in the body. The local depletion at least reduces the progression of the disease at least at the locality. The local depletion reduces one or more symptoms of the disease at least at the locality.

Cancer does not have one specific cause. However, central to the growth and maintenance of many cancers is their dependence on one or more extracellular stimuli. Antibodies targeted to the cancer cells are presently being evaluated in clinical trials. Such antibodies are typically directed towards molecules present on the cancer cells or the associated matrix. The binding molecules in the first polymer network of the hydrogel particles of the present invention are typically not directed towards such associated markers as these are linked to large structures that cannot diffuse into the polymer network of the particle. Instead the binding molecule is preferably directed towards a soluble peptide or protein with tumor maintenance or tumor growth effect or an immune response inhibiting effect. Non-limiting examples of such factors are the various soluble EGF or EGF-like factors, the various rspondins, Bmps, TGFbs. WNTs, FGFs, VEGF, CXCLs, ARGs, CCLs, ILs, TNFs, MMPs, ADAMTs, ANGs, PDGFs, IGFs, HGFs, PIGFs, and/or OPN. One or more of these factors can be depleted from the locality by injecting a hydrogel particle, a pharmaceutical solution, or a pharmaceutical composition as described herein and having one or more binding molecules specific for one or more of these factors at the affected locality in the body. The local depletion at least reduces the progression of the cancer at least at the locality. The local depletion reduces one or more symptoms of the cancer at least at the locality.

Another way of treating vascularized cancer is by locally sequestering and/or depleting vasculature stimulating soluble factors such as VEGF and/or FGF. Other vasculature stimulating soluble factors that can be sequestered are Bmps, TGFbs. WNTs, FGFs, VEGF, CXCLs, ARGs, CCLs, ILs, TNFs, MMPs, ADAMTs, ANGs, PDGFs, IGFs, HGFs, PIGFs, and/or OPN. This at least reduces new vascularization near the injection site(s).

Inflammation is part of the biological response of body tissues to harmful stimuli, such as pathogens, damaged cells, or irritants. It is a protective response involving immune cells, blood vessels, and molecular mediators. Inflammation is typically helpful in counteracting the harmful situation. However, when exceedingly strong, or chronic, inflammation can be harmful by itself. Inflammation is a process that involves various interactions of cells, matrices and structures. It also involves so-called pro-inflammatory cytokines. One or more of these cytokines can be depleted from the locality by injecting a hydrogel particle, a pharmaceutical solution, or a pharmaceutical composition as described herein and having one or more binding molecules specific for one or more of these cytokines at the affected locality in the body. The local depletion at least reduces the progression of the inflammation at least at the locality. The local depletion reduces one or more symptoms of the inflammation at least at the locality.

Non-limiting and preferred examples of cytokines to which a binding molecule present in the first polymer network may be directed are: interleukin-1 (IL-1); IL-2; IL-4, IL-6, IL-10, IL-12, IL-13, IL-17 and IL-18, tumor necrosis factor (TNF), interferon gamma (IFN-gamma), IFN-alpha, and granulocyte-macrophage colony stimulating factor.

The auto-immune disease is preferably arthritis, preferably rheumatoid arthritis. The hydrogel particles comprising a binding molecule specific for a pro-inflammatory cytokine is particularly suited to treat joint symptoms in arthritis, preferably rheumatoid arthritis.

The disease is preferably rheumatoid arthritis, Crohn's disease, asthma, bacterial infection, sepsis, whole organ failure, cancer, or transplant rejection. The disease is preferably a disease that can be treated via the implantation of an engineered tissue or organ.

The hydrogel particles comprising a binding molecule specific for a pro-inflammatory cytokine is particularly suited to treat joint-inflammation.

Also provided is a method of treatment of a subject with an over-active immune system, a cancer, or over-active hormone and/or cytokine producing cells comprising administering the subject in need thereof a hydrogel particle as described herein or a pharmaceutical solution or composition comprising said hydrogel particles. The administration is preferably by means of injection at a locality. Preferably a tumor, a particular site of inflammation, such as an arthritic joint. The inflammation is preferably a joint-inflammation.

When implanted in highly vascularized areas like the liver, the microparticles can be used for systemic treatments, or in vivo dialysis'. For example, by injection in the portal vein, microparticles get stuck in capillary bed of the liver, where they can then deplete the blood of harmful/'unwanted' cytokines. In this setting they can also be used for the treatment of allergies, by capturing allergens, histamines or allergy-inducing cytokines from the blood. Intravascular injection also leads to efficient retention in the capillary beds of lungs, which can also be used to ease the diseases burden e.g. by alleviating the inflammation.

In cell biology research the microparticles can be used to deplete a cell, a tissue culture, or engineered tissue from specific growth factors or cytokines. This allows a tight control over the crosstalk of cells or cell types in, for example, cellular co-cultures.

Cytokine sinks may also be used during/after surgery as a preventive treatment against (chronic) inflammation. Besides injection, affinity microparticles can also be optimized as therapeutic agents of the digestive tract (e.g. regulation of the intestinal flora/advanced probiotics). For veterinary purposes: systemic depletion of growth factors/ antibiotics before slaughter to minimize meat/food contamination. Hydrogel particles as described herein can be used in eye drops, topical use (cream/lotion). Combinatorial approaches using multifunctional cytokine sinks or a mixture of distinct cytokine sinks can be used. As an alternative for the resin in hemoadsorption devices such as the CytoSorb allowing depletion of blood from cytokines in a specific manner.

Injection can be in the tumor, inflammation area, intravenous, intramuscular, intraperitoneal etc.

In vitro administration of a hydrogel particle as described herein can be performed with any suitable means for delivering a fluid, such as a container with a closeable orifice. For instance a printing nozzle or a printing device.

Further provided is a method for reducing the bioavailability of a soluble biological molecule in a biological system, the method comprising providing said system with hydrogel particles as described herein, wherein the biological molecule comprises a hydrodynamic radius that can access said polymer network and said binding molecule can bind said biological molecule. The biological system can be an in vitro cell culture system. Such systems are inherently closed and provide a local environment to the hydrogel particle. The particles are particularly suited to deplete the culture medium from one or more undesired soluble proteinaceous factors. When growth is not desired the factor can be soluble growth inducing factor depending on the type of cells that are cultured. Non-limiting examples are EGF and insulin like growth factor. When growth is desired the factor can be soluble growth inhibiting factor depending on the type of cells that are cultured. For instance when culturing and differentiating stem cells it can be advantageous to inhibit differentiation into other than desired lineages by depleting the culture for differentiation factor(s) that induce differentiation into this undesired lineage. The invention also provides a use of a hydrogel particle, a pharmaceutical solution or composition as described herein for reducing the bioavailability of a biological molecule in a biological system.

The biological system can also be human or a non-human animal. The biological system can also be an organ-on-a-chip, preferably composed of one or more organs, or an engineered physiological system aimed at replicating human biology in an ex-vivo manner.

Also provided is a method for reducing the bioavailability of a biological molecule in a biological system, the method comprising providing said system with a hydrogel particle as described herein, wherein said biological molecule has a molecular weight of 200 dalton to 150 kilodalton and wherein said binding molecule binds said biological molecule.

Also provided is the use of a hydrogel particle as described herein as a cytokine sink.

Hydrogel particles as described herein can have a porous surface and an first polymer network that comprises a binding molecule immobilized in the first internal polymer network. The pores in the porous surface may have an average cross sectional diameter of from about 0.1 nanometer (nm) to 1000 nm. The pores in the porous surface preferably have an average cross sectional diameter of 0.5-1000 nm; preferably 2-300 nm; preferably 2-100 nm, more preferably 5-50 nm.

An IgG antibody typically has a molecular weight of 150 kDa and a cross-sectional diameter in the range of 10 nm. Such molecules can easily diffuse into a hydrogel particle with pores of 100 nm. An IgG molecule has a hydrodynamic radius of about 5.5 nm.

A cross sectional diameter of a particle or a pore is the diameter of a surface formed by cutting perpendicular to its longest axis. If the surface is not roughly circular the diameter is half of the sum of the length of longest distance and the length of the shortest distance between two opposing points on the cross section. The cross-section is typically at the broadest point.

Cross-sectional diameters indicated herein refer to diameters of or in hydrated hydrogel particles. Preferably with a physiological saline aqueous solution at pH 7-8, such as phosphate-buffered saline pH7.4.

A peptide has fewer amino acids than a protein. The difference size between a peptide and a protein is often arbitrary. In the present invention peptides are defined as molecules that consist of between 2 and 50 amino acids. Protein are molecules with more than 50 amino acids.

A biological molecule is a molecule that is or can be produced by an organism. Peptides and proteins are considered biological molecules in the present invention, also when they are synthesized artificially.

In some embodiments, the hydrogel can further comprise a molecule that can diffuse out of the particle, for instance to provide a slow release of the molecule in addition to the "sink" functionality of the particle towards the target biological molecule. In one embodiment displacement of a desthiobiotinylated molecule by a biotin or biotinylated molecule can be used for the on-demand and/or controlled release of the desthiobiotinylated molecule to, e.g. switch off its local function or achieve its on-demand and/or controlled release.

For the purpose of clarity and a concise description features are described herein as part of the same or separate embodiments, however, it will be appreciated that the scope of the invention may include embodiments having combinations of all or some of the features described.

Examples

Three examples are provided that describe among others i) the in vivo application and biological stability of VHHs; ii) the fabrication of VHH-functionalized hydrogel particles and their application in vitro and in vivo; and iii) the fabrication of hollow/core-shell hydrogel particles and the measurement of the mesh size or molecular weight cut-off of these networks.

Example 1

The capacity of hydrogel conjugated VHHs to work as cytokine sinks over a period of various weeks requires that the conjugated VHHs remain biologically active for such a long period in the body. To test the stability of the VHHs in the body we injected mice with a bifunctional VHH (bihead) that simultaneously binds to hydroxyapatite in bone and to the growth factor BMP7.

Materials and Methods

Library Construction and Selection of VHH Targeting BMP7

All immunizations were approved by the Utrecht University ethical committee for animal experimentation. Two llamas were immunized with recombinant human BMP7 (R&D systems, #354-BP/CF). The antigens were mixed with the adjuvant Stimune (CEDI Diagnostics, Lelystad, the Netherlands) and injected intramuscularly at days 0, 14, 28 and 35. At day 44, peripheral blood lymphocytes were isolated for RNA extraction and library construction. The VHH phage display libraries were generated as previously described [1-3] and transferred to Escherichia coli (E. coli) strain TG1 [supE hsd_5 thi (lac-proAB) F (traD36 proAB_laclq lacZ_M15)] by electroporation.

Phages binding to BMP7 were selected via the panning method. Decreasing concentrations of BMP7 (5 µg, 2 µg and 0.2 µg) in phosphate buffered saline (PBS, Gibco) were coated in the wells of MaxiSorp plate (Nunc, Thermo Scientific) overnight at 4° C. Phages, approximately 1010 colony forming units (cfu), were incubated for 2 hours at room temperature (RT) with the coated BMP7, and blocked with 4% Marvel (dried skimmed milk, Premier International Foods) in PBS. After washing thoroughly, phages binding to BMP7 were eluted by incubating them in 100 mM triethylamine (TEA) for 15 minutes at RT. Eluted phages were immediately neutralized through the addition of 1M Tris-HCl, pH 7.5. DNA information of the selected phages was rescued by means of infection with the E. coli TG1 strain and subsequent selection for ampicillin resistance on agar plates. To obtain recombinant bacteriophages expressing the VHH as fusion proteins with the bacteriophage gene III, rescued TG1 E. coli were grown to logarithmic phase and then infected with helper phage VCSM13 (Stratagene, La Jolla, Calif., USA) [4]. The phage particles were precipitated with polyethylene glycol (PEG) and used in the second round of selection, on wells coated with BMP7 as described above. Selected phages from single colonies from the second round of selection were sequenced (Macrogen). Among several VHH candidate clones, the selected one was named VHH G7 (G7) after analyzing for further characterization.

Selection of VHH Targeting HA

VHH binding to HA were selected from a non-immunized llama VHH phage library (kindly provided by BAC BV). The construction of the non-immune library has been described before [5]. A two-round selection was performed on HA plates. Pure HA plates measuring approximately 1.5×1.5 mm and of a 0.1 mm thickness were supplied by Plasma Biotal Limited, UK. Phages were incubated with 3 HA plates in the wells of a 96-wells microtiter plate. The procedure that followed was the same as for VHH G7 selection. Finally, one VHH, named VHH-MA10 (MA 10), was chosen for further study.

Figure 5:
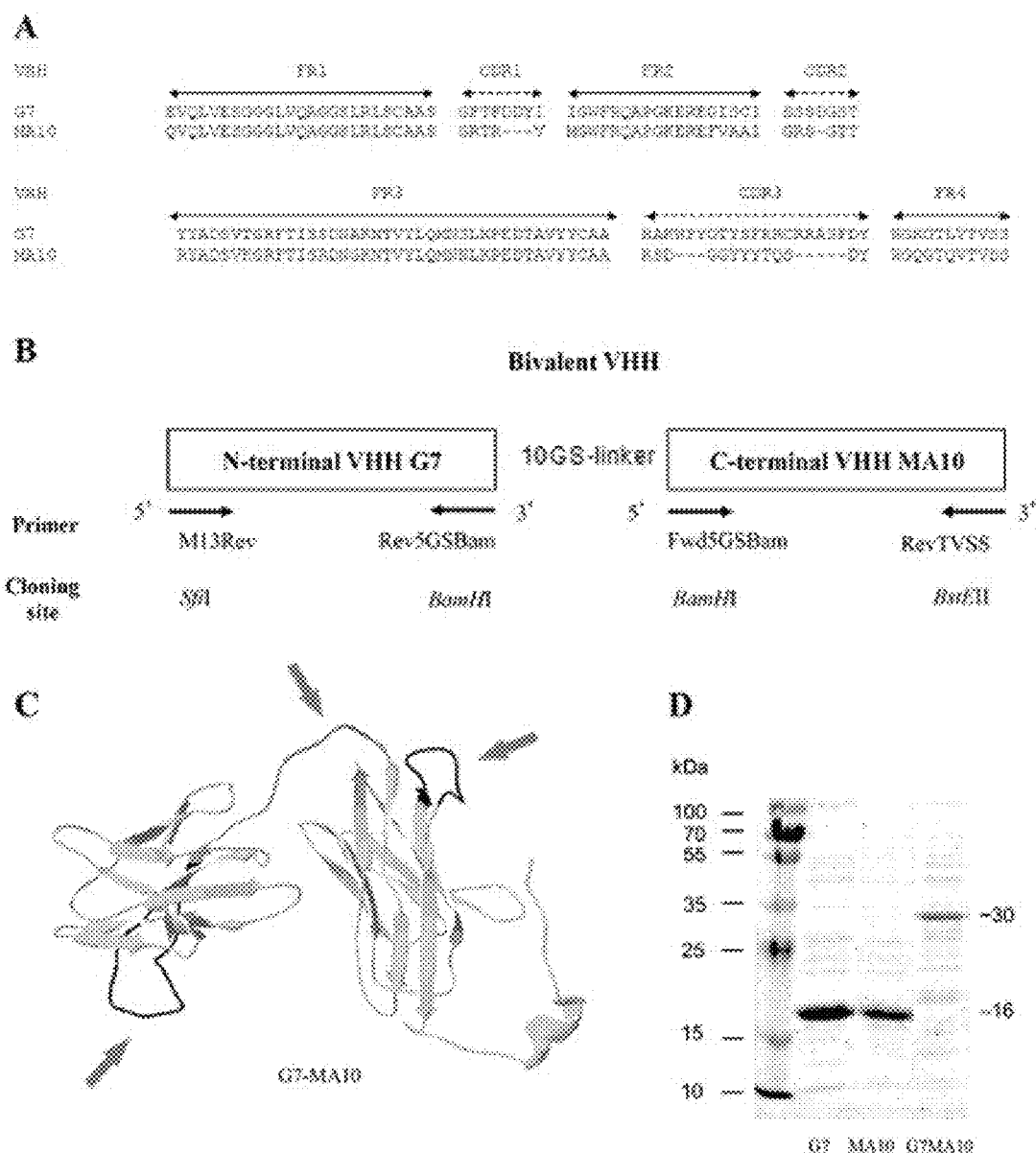
FIG. 5: Construction and production of bihead G7-MA10. (A) Amino acid sequence alignment of VHH G7 and MA10. Frame works (FR) and complementary determining regions (CDR) of the VHH are indicated according to Chothia [29]. (B) The engineered bivalent VHH is schematically represented. Position of G7 at the N-terminus and MA10 at the C-terminus as well as the GS linker are indicated. (C) Predicted 3D protein model of the generated bivalent G7-MA10, where the GS linker is highlighted in yellow and the CDR3 of G7 and MA10 are shown in black. (D) Recombinantly expressed VHH G7, MA10 and G7-MA10 were sized-separated by a 15% SDS-PAGE and stained with Coomassie Brilliant Blue. Molecular weight markers (in kDa) are indicated at the left. Calculated molecular weight of the monovalent and bispecific VHHs are indicated at the right. (E) Binding specificity of bihead VHHs to HA by ELISA. Data is expressed as the mean+/−standard deviation of at least 3 replicates.

The bihead G7-MA10 was constructed by genetic fusion of the cDNAs, encoding the VHH binding to BMP7, G7, and the VHH binding to HA, MA10 (FIG. 5). PCR was used to amplify the VHH sequences. Different primers sets were designed to amplify the VHH G7, located at the N-terminus, and the VHH MA10, placed at the C-terminus, to generate a bivalent VHH (M13Rev: GAGGTGCAATTGGTG-GAGTCTGGG; 5GSBamRev: AGTAGGATCCGC-CACCTCCTGAGGAGACCGTGACCTGGGTCCC; 5GSBamFwd: TCTTGGATCCGAGGTGCAGCTGGTG-GAGTCTGGG; TVSSRev: TGAGGA-GACGGTGACCTGGGTCCC). The primers at the 3' of the N-terminus VHH and at the 5' of the C-terminus VHH encoded a flexible sequence (GS linker) represented by the pentapeptide 'Gly-Gly-Gly-Gly-Ser'. The primers contained a unique restriction site (BamHI). After PCR amplification, the generated fragments were digested with a unique N-terminal restriction site (SfiI) and BamHI for the VHH located at the N-terminus, and with BamHI and a unique C-terminal restriction site (BstEII) for VHH located at the C-terminus. The fragments were ligated into the expression vector, pMEK222, which was digested with SfiI and BstEII, after which they were transformed into E. coli for expression.

E. coli strain TG1 was used for the maintenance of the plasmids, infection by the phages and expression of proteins. For detection purposes in following assays, two vectors with different tags were used in order to specifically detect the VHH. The DNA information of the individually selected and isolated VHH was therefore subcloned into plasmid pUR8100 (for MA 10) or pMEK219 (for G7) containing a C-terminus Myc and His tags, and pMEK222 containing C-terminus FLAG and His tags. E. coli TG1 was grown in Luria Broth (LB) or yeast extract and tryptone (YT) medium containing 2% (w/v) glucose and ampicillin at 100 µg/ml; VHHs were produced from E. Coli TG1 by Isopropyl β-D-1-thiogalactopyranoside (IPTG) induction of the lac promoter at 37° C. for 4 hours under non-static conditions. VHH proteins were purified from the periplasmic fraction via the C-terminus His-tag by cobalt affinity chromatography (TALON His-Tag Purification Resin, ClonTech). Purified VHHs were analyzed by means of sodium dodecyl sulfate polyacrylamide gel electrophoresis (SDS-PAGE). The final VHH concentration was determined on the basis of UV absorption at 280 nm (NanoDrop 1000 Spectrophotometer, Thermo Scientific) and the theoretical mass extinction coefficient.

VHH Binding Specificity

The binding specificity of the purified VHHs (G7, MA10, G7-MA10) was tested in an enzyme linked immunosorbent assay (ELISA) binding assay. The binding of MA10 to bone was further tested in mouse fetal metatarsals.

Binding Specificity of VHH-G7 or Bihead G7-MA10 to BMP7

MaxiSorp plate wells were coated with BMP7 (30 nM) in PBS overnight at 4° C., after which they were blocked with 2% BSA in PBS for two hours at RT in order to block non-specific binding sites. Subsequently, wells were incubated with a serial dilution of VHHs (ranging from 0 to 7 µM) in 1% BSA in PBS for two hours at RT. The wells were washed with PBS tween (PBST) and PBS. Bound VHHs were detected by incubation with a rabbit anti-VHH serum (K976) and a donkey anti-rabbit antibody coupled to a peroxidase. The amount of Horse Radish Peroxidase (HRP) was developed by the addition of Tetramethylbenzidine (TMB, 1-Step Ultra TMB-ELISA, Thermo Scientific). The reactions were stopped by the addition of $H_2SO_4$ and measured at 450 nm (Micro Plate Reader). The dissociation constants (Kd) were obtained from the subsequent association of experimental data with specific binding models. The data was normalized to the condition without VHHs.

Binding Specificity of VHH-MA10 or Bihead G7GS10MA10 to HA

Microtiter plate wells containing three pure HA plates were blocked with 2% BSA in PBS for two hours at RT in order to block non-specific binding sites. The following steps were performed as G7 to BMP7.

VHH-MA10 Bind to Mouse Fetal Metatarsals

Mouse fetal metatarsals were isolated from FVB mouse embryos (time-paired, Harlan) at day 17.5 of gestation. (Animal experiments were approved by a local animal ethical committee). After isolation, metatarsals were individually cultured in wells of 24-well plates in 200 µl α-MEM, supplemented with 10% FBS, 100 U/ml penicillin, 100 mg/ml streptomycin and 1% Glutamax (Invitrogen) for 48 hours at 37° C. in humidified atmosphere and 5% CO2. After this equilibration period, metatarsals were incubated in the presence of VHH (1 µg/ml) for 2 hours at 37° C. in humidified atmosphere and 5% CO2. To enable visualization, prior to incubation, VHH MA10 and control VHH 1B5 were randomly labeled with Alexa Fluor 647, following the manufacturer's protocol (Invitrogen). This resulted in VHH MA10-647 and 1B5-647. After intensive washing with PBS, the metatarsals were evaluated for fluorescence with BD Pathway (BD Biosciences) with an excitation filter of 628±40 nm and an emission filter of 692±40 nm.

Dual Binding Specificity of Bihead G7GS10MA10 to HA and BMP7

We further tested if the G7 moiety of the bivalent VHH was still able to bind to BMP7 after being immobilized on HA plates. For this purpose, pure HA plates were incubated with serial concentrations of VHHs (ranging from 0 to 7 µM) in 1% BSA in PBS for two hours at RT after blocking them with 2% BSA for two hours and with 4% Marvel (Marvel original dried skimmed milk) subsequently for one hour. Subsequently, the HA plates were incubated with hBMP7 (300 ng/ml) and mouse anti-hBMP7 (1 µg/ml) antibody for one hour at RT. In between these steps, the wells were washed with PBST and PBS. Bound anti-hBMP7 was detected by incubation with a donkey anti-mouse antibody coupled to HRP in 1% BSA in PBS (1 hour, RT). The amount of HRP was quantified by addition of OPD in the presence of $H_2O_2$ (30 min, RT). The reaction was stopped by addition of $H_2SO_4$. Subsequent measurements were performed at 490 nm.

Biological Activity of VHH G7 and Bihead G7-MA10

Alkaline Phosphatase (ALP) Assay

The C2C12 cell line was used for osteogenic differentiation. Cells were cultured in DMEM (Gibco) supplemented with 10% fetal bovine serum (FBS, Cambrex), 100 U/ml penicillin (Gibco) and 100 µg/ml streptomycin (Gibco), and were incubated at 37° C. in humidified atmosphere and 5% CO2. To perform differentiation assays, cells were seeded at a density of 10,000 cells/$cm^2$ (day 0). Upon reaching confluence (day 4) cells were cultured for 3 days with ascorbic acid (50 µg/ml; Sigma Aldrich) and stimulated with BMP7 (300 ng/ml; R&D Systems) in the presence or absence of VHH G7 (1 µg/ml) or G7GS10MA10. At day 7, cells were washed with PBS and lysed with CDPStar lysis buffer (Roche). To evaluate ALP activity, cell lysate was added to CDPStar reagent (Roche) and luminescence was measured using Vector Microplate Luminometer (Promega). The luminescence units were corrected for DNA content. DNA concentration was determined via proliferation assay according to the manufacturer's protocol (CyQuant Cell Proliferation Assay Kit, Invitrogen).

ALP Staining and Imaging

Pure HA plates were placed in a 96-well plate (flat bottom) and sterilized with 70% ethanol for 2 hours. C2C12 culture medium was added to the wells for 2 hours. Bihead VHH (1 µM) was added to the wells in 1% BSA in PBS and kept at RT for 2 hours. hBMP7 (300 ng/ml) was added to the wells in PBS and left for 2 hours. In between these steps, the wells were washed with PBS. C2C12 cells, at a seeding density of 10,000 cells/well, were added to the wells together with ascorbic acid. After three days, the ALP expression on HA plates was determined by the Sigma Alkaline phosphatase kit following the protocol. The image was taken by stereoscopic microscope after counter-staining the cell nuclei with nuclear fast red.

VHHs In Vivo Experiments

Labeling of MA10 and Bihead G7GS10MA10 with Near Infrared IRDye 800 CW (IR)

On the basis of the promising results of VHH MA10 and bihead G7GS10MA10 binding to mineralized bone matrix, near infrared IRDye 800 CW was chosen to label the VHHs for further detection in the vivo mouse model. VHH J3 was used as a non-HA binding control. A direct labeling strategy, consisting of site-directed labeling of the VHH's C-terminus, was used to avoid interference with antigen-antibody interaction. This was achieved through the genetic introduction of an unpaired cysteine at the VHH's C-terminus (MA10-CYS or G7GS10MA10-CYS), which could be conjugated to a maleimide containing IRDye 800 CW. VHH MA10-CYS and G7GS10MA10-CYS were modeled using the online program I-TASSER for protein modeling [6-8]. The obtained VHH MA10-IR and G7GS10MA10-CYS-IR were tested for binding to HA or to HA and BMP7 simultaneously to confirm that the genetic modification and labeling did not interfere with the function of the VHHs.

In Vivo Performance of MA10

To assess the possibility of MA10 targeting mineralized bone, MA10-IR was intravenously injected in two groups of balb C nu/nu mice (Charles River, France). One group was injected with VHH MA10-IR (70 µg/100 µl) and the other was injected with the negative control VHH J3-IR (70 µg/100 µl). The PEARL Impulse imaging camera (Li-Cor. Lincoln, Nebr.) was used to image the mice. The mice were anesthetized with 2% Isoflurane and imaged in ventral and dorsal positions at 0, 1, 3, 24, 48 and 72 hours and 7, 16 and 20 days post injection. The results were analyzed with Pearl Impulse software 3.01. The mice were sacrificed with $CO_2$ at 20 days post injection. The organs and skeletons were isolated and imaged.

In Vivo Performance of G7GS10MA10

This study includes four experimental groups. Six animals from each group were used to measure the dual activities of bihead bound to the bone and BMP7 simultaneously, thus BMP7 was directed to the bone area by bihead targeting hydroxyapatite. Mice from group 1 were injected with IR-labeled bihead (20 ug/100 ul), mice from group 2 were injected with BMP7 only (15 ug/100 ul), mice from group 3 were injected with a mixture of IR-labeled bihead and BMP7 (20 ug bihead and 15 ug BMP7/100 ul); the mixture was prepared 2 hours before injection. Group 4 was injected with PBS negative control. At day 20 (24 hrs before sacrifice), 3 mice of each group received another injection of BMP7 (15 ug/100 ul). IR imaging was performed at regular time intervals: at day 0, 2 hrs, 24 hrs, 72 hrs, 7 d, 14 d, 21 d in ventral and dorsal position. All groups were sacrificed 21 days after injection, and a number of organs and skeletons were collected and imaged.

Microscopic Images of the Bone of IR-Bihead Injected Mice

In order to detect the fluorescence signal location inside bone, microscopic imaging was performed after methyl methacrylate (MMA) embedding. To make sample slides, skeleton samples were fixed in 10% formalin 24 hours after sacrifice. Samples were rinsed with PBS and put into a Tissue Processor to dehydrate at 70% ethanol for 4 hours, 80% ethanol for 4 hours, 90% ethanol for 4 hours, 96% ethanol for 4 hours, 100% ethanol for 4 hours and 100% ethanol for 4 hours. The dehydrated skeletons were incubated with MMA solution (135 ml K-plast A, 15 mL K-plast B, 1.5 g initiator) for 1 week at 4° C.; the solution was changed every two days. Once the MMA had thoroughly infiltrated the skeleton, MMA embedding was performed by incubation with MMA solution overnight at 4° C., followed by a water bath at 37° C. until the MMA had hardened. A 300 µm section was sliced from the MMA embedded skeleton with a diamond blade (LEILA SP1600) and imaged using an Odyssey Near Infrared imaging system coupled to a microscope.

Immunochemistry for Skeletons of IR-Bihead Injected Mice

In order to detect whether the injected BMP7 had been directed to the bone tissue by the bihead and following triggered BMP7 signal transduction, rabbit source anti-VHH (QVQ), anti-BMP7 (Peprotech) and anti-SMAD 1 (Santa Cruz) antibodies were used for the purpose of immunochemistry. After decalcification for 3 weeks in EDTA solution (solution changed every week), the injected mice skeleton was embedded in paraffin and a 5 µm section was sliced. The slides were de-paraffinized in xylene and rehydrated with graded ethanol. The antigen was retrieved by a citrate buffer (10 mM pH6.0) 2 min in a microwave, then cooled down to RT. This was followed by blocking the endogenous-peroxidase by a 3% H2O2 solution for 15 min at RT. After blocking in 5% BSA in PBS for 1 hour, samples were incubated overnight with primary specific antibody diluted in blocking buffer (anti-VHH 10 µg/ml, anti-BMP7 10 ng/ml, anti-SMAD1 10 ug/ml) and IgG control antibody at 4° C. Followed by adding biotinylated goat anti-rabbit IgG (Abcam) for 30 min, and HRP-strep in PBS (2 ug/ml) for 30 min, Samples were incubated in DAB solution (Abcam) for 10 min, hematoxylin was used to counterstain the nuclei for 10 sec. The samples were washed 3 times by PBS between each step. Nanozoomer was used to take an image.

Statistical Analysis

Statistical analyses were performed using GraphPad Prism version 5.00 for Windows, GraphPad Software (San Diego, Calif.). The analyses were based on one-way ANOVA and a Tukey's Post-hoc test ($p<0.05$) among all samples or between samples and controls. Error bars indicated standard deviation.

Results

VHH Targeting BMP7 (VHH-G7) Production and Characterization

Figure 4:
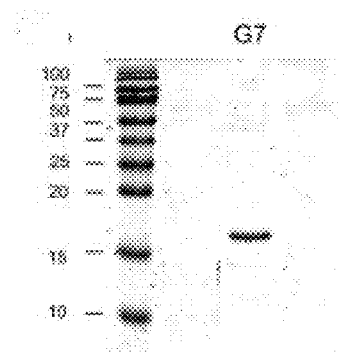
FIG. 4: Characterization of VHHs targeting hBMP7. (A) The amino acid sequence of VHH-G7 targeting hBMP7. Frame works (FR) and the complementary determining regions (CDR) are indicated according to Chothia [39]. (B) Purified G7 was sized-separated by a 15% SDS-PAGE and stained with Coomassie Brilliant Blue. Molecular weight markers (in kDa) are indicated at the left. (C) The specific binding of VHH-G7 to hBMP7 in ELISA. Data is expressed as the mean+/−standard deviation of at least 3 replicates.
Figure 4:
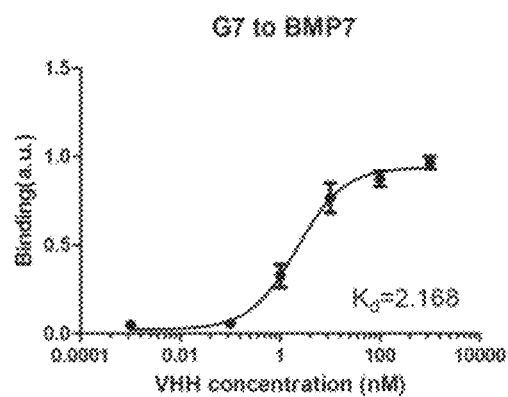

VHH was selected from phage display libraries constructed from RNA isolated from PBLs of llamas immunized with recombinant human BMP7. After two selection rounds, a clear enrichment was found on the antigen-coated wells in comparison with empty wells. Several clones were selected for further screening using binding to BMP7. From two master plates of 190 VHH clones, the selection of individual clones was sized down by grouping on the basis of restriction patterns and an ELISA binding assay. One clone named VHH G7 (G7) was selected for further characterization based on binding specificity. The gene sequence was subcloned into expression plasmids and produced and purified as indicated in materials and methods. The sequence of clone G7 is shown in FIG. 4. The purity of the recombinantly produced VHH was assessed by SDS-PAGE and Coomassie blue staining (FIG. 4). A clear band was observed with a size of 16 kDa. To confirm the specific binding of VHH G7 to hBMP7, an ELISA was performed (FIG. 4). The data indicated that VHH G7 binds to hBMP7 with a $K_d$ of 2.2 nM.

VHH Targeting HA (VHH MA10) Production and Characterization

VHH were selected from a non-immunized phage library. The selections were performed on HA plates placed in wells of a 96-wells microtiter plate. A total of two selection rounds were performed on HA plates to achieve an enrichment of phages binding to HA plates. Six single clones that showed binding to HA were selected during screening. After VHH expression and sequence determination, clone MA10 was selected for further characterization. VHH MA10 was purified from the periplasmic fraction of *E. coli* TG1 using TALON. The size and purity of the VHH were assessed by SDS-PAGE where a single band was detected of 16 kDa. The specific binding of VHH MA10 to HA was tested by ELISA. VHH MA10 showed binding to HA in a dose dependent manner with an apparent affinity of $K_d$=73.9 nM.

We next tested whether MA10 could be used for visualizing mineralized bone using explanted fetal mouse metatarsal. For this, VHH MA10 was labeled with Alexa fluor 647. An unrelated VHH was used as a negative control VHH 1B5 and was also labelled. The labeling efficiency obtained was 30% and 50% for VHH MA10-647 and 1B5-647, respectively. Next metatarsals were incubated with both VHHs. Fluorescent microscopy on the intact metatarsals revealed that VHH MA10-647 was specifically bound to the mineralized cartilaginous matrix of the primary center of ossification. In addition, binding to the developing bone collar in which mineralized bone matrix is deposited was observed. In contrast, VHH 1B5-647 binding to mineralized extracellular matrix was strongly reduced, with the exception of some nonspecific fluorescence at the boundary of the mineralized and hypertrophic cartilage, and with faint fluorescence in the bone collar. Interestingly, Alexa Fluor 647 did not display any significant auto fluorescence using an emission filter of 692±40 nm.

Bihead G7-MA10 Production and Characterization

In order to explore the potential of VHH with dual specificity in functionalizing biomaterial surfaces, a bispecific VHH consisting of an anti-BMP7 and an anti-HA was constructed. PCR was used to link the genes of the two VHHs (FIG. 5) and to introduce a linker sequence between them, as described in material and methods (FIG. 5). The resulting bihead VHH is schematically illustrated in FIG. 5. Its structure was predicted by ITASSER demonstrating that the genetic fusion did not impact the exposure of the complementary determining regions (CDR) involved in antigen binding [17-19]. The fusion gene of the G7GS10MA10 was subcloned into expression plasmids and produced and purified as indicated in materials and methods. As shown in FIG. 5, the size of the produced bihead VHH had the expected molecular weight of 30 kDa, about twice that of the monovalent VHHs which have a weight of 16 kDa, as shown by SDS-PAGE.

Figure 6:
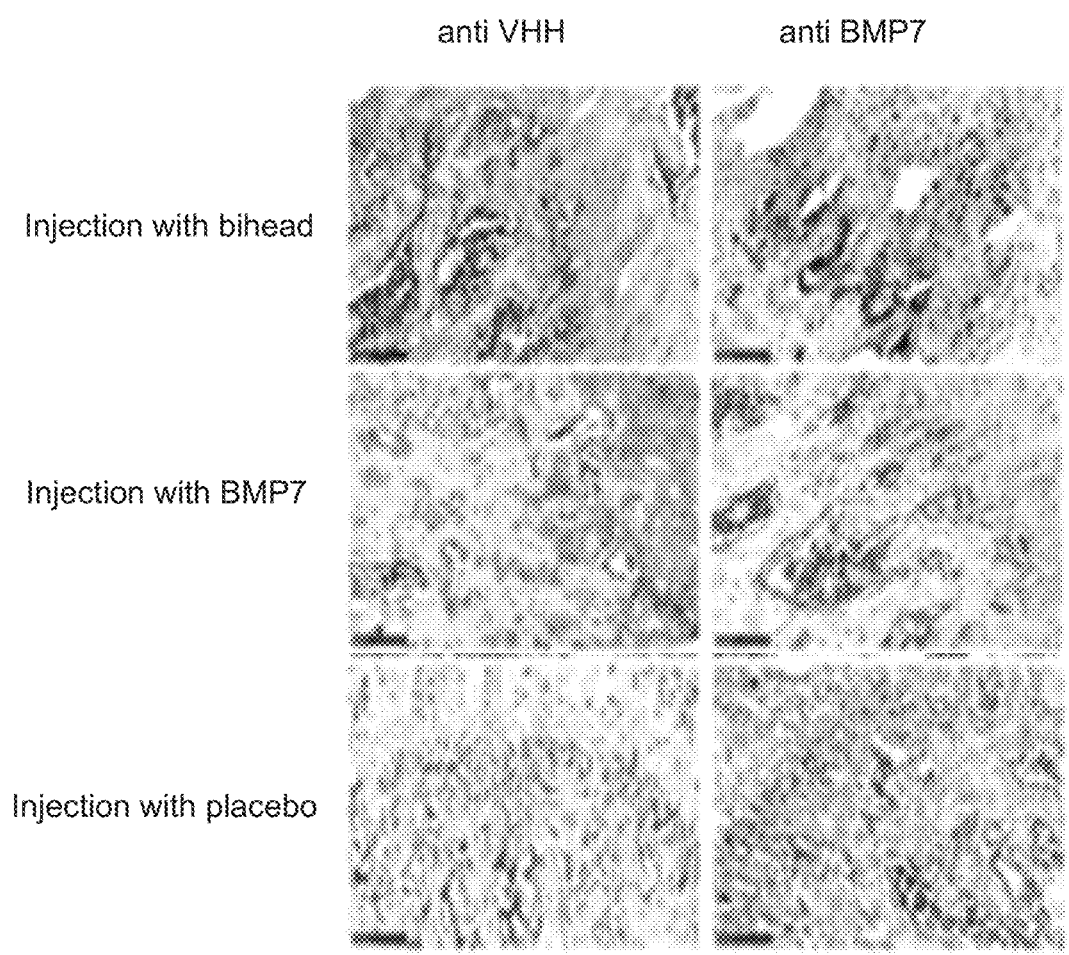
FIG. 6: Immunohistochemical staining for VHH and BMP7. Mice were injected with a bifunctional (bihead) VHH that binds simultaneously to hydroxyapatite in mineralized bone and cartilage and BMP7, the growth factor BMP7 or placebo. At day 20, one day before sacrifice, half of the animals were injected with the growth factor BMP7. At day 21, animals were sacrificed, bones were isolated and processed for immunohistochemistry using an anti-VHH antibody (left panels) or an anti-BMP7 antibody. Only mice injected with the bihead stained positive for VHH (top panel). Only in mice 20 days earlier injected with the bihead, BMP7 was specifically enriched in mineralized bone and cartilage (top, right). The BMP7 staining co-localized with the VHH staining demonstrating that the VHH was still able to bind to BMP7 even 3 weeks after the first injection in mice. Injection with BMP7 only (middle panel) or with placebo (lower panel) did not show VHH staining nor clear enrichment of BMP7 (middle panel) or complete absence of BMP7 in mineralized bone and cartilage.

In order to show whether the combination of MA10 and G7 in a bispecific VHH influences the binding of the MA10 part of the bihead VHH to HA and accordingly the G7 part to BMP7, the binding specificity was determined using ELISA. As shown in FIG. 6, bihead VHHs show specific binding to HA with an apparent affinity of $K_d$ of 62.59 nM, and to hBMP7 with an apparent affinity of $K_d$ of 0.4 nM, respectively, which is in agreement with the affinities of the individual components for HA and hBMP7. In order to show if the bihead VHHs are also able to bind to HA and hBMP7 simultaneously, a binding curve was obtained for hBMP7 to the bihead which was first immobilized on a HA disc. As shown, the bihead was able of binding both HA and hBMP7 albeit that the binding to HA reduced the affinity of G7 for hBMP7.

The biological activity of VHH-G7 or bihead G7-MA10 hBMP7 was tested in C2C12 cells. ALP is an early marker of osteogenic differentiation, and it is strongly induced by hBMP7. Here we determined the effect of VHH-G7 or bivalent G7-MA10 in the presence or absence of hBMP7 in culture medium on Alkaline Phosphatase activity (ALP) over a 7-day period. ALP activity was induced around 400-fold in the presence of hBMP7. Interestingly, when cells were co-treated with hBMP7 in the presence of VHH-G7 or bihead G7-MA10, a clearly superior induction of ALP activity was observed: Both VHHs increased ALP activity induced by BMP7 with 177%. There was no significant difference between G7 and G7-MA10.

We next tested whether the potentiating effect of the bihead G7-MA10 on hBMP7 activity was preserved when the bihead was bound to HA, For this, C2C12 cells were cultured on pure HA plates after pre-incubation with bihead and/or hBMP7. The HA plates were extensively washed with PBS between steps before cells were seeded on top. Compared to control, pretreatment of HA discs with hBMP7 marginally induced ALP acitivity. Much stronger induction of ALP activity was found in discs pretreated with both the bihead and BMP7. This indicated that the bihead was able to sequester hBMP7 out of the medium on the biomaterial surface and that this local enrichment is sufficient to induce ALP activity in the C2C12 cells.

Infra-Red Labeled VHH MA10 Binds to Mineralized Skeleton

In order to evaluate the potential of MA10 as a probe for optical imaging of bone tissue, MA10 was labeled using a near infrared label yielding MA10-IR. The label process did not affect the binding specificity of VHH to HA determined by ELISA. Next, nude mice were intravenously injected with MA10-IR in the tail vein and imaged at several time points post-injection. Littermates were treated in the same way with the non-binding VHH J3-IR as negative control, and images of the two groups were compared. Images taken at early time points showed IR fluorescence throughout the whole body of the mice in the case of MA10-IR (up to 7 days post-injection) and in the case of J3-IR (up to 3 days post-injection). At day 20 fluorescent label was still detectable in the skeleton of mice injected with MA10-IR, in contrast to J3-IR injected mice. After sacrificing, the skeleton and organs were isolated and imaged. The dorsal and ventral images showed a clearly defined skeleton with high fluorescence measured for MA10-IR. Specific accumulation of MA10-IR occurred in mineralized bones. In contrast, no fluorescence was measured for the VHH J3-IR in the skeleton. For both VHH, liver, spleen and kidneys show fluorescence after 20 days. Fluorescence was clearly visible at the kidneys for both groups. Obviously, J3-IR was cleared from the body much faster than MA10-IR, suggesting that targeting the skeleton through binding to hydroxyapatite extended the retention time of the VHH in the body considerably to at least 20 days.

Bihead VHHs Efficiently Direct hBMP7 to Bone by Targeting Hydroxyapatite

In order to evaluate whether hBMP7 can be directed to the bone area by the dual binding activity of bihead G7-MA10 to BMP7 and HA simultaneously, bihead G7-MA10 was labeled by IR to G7-MA10-IR. ELISA result showed the labeling did not affect the binding specificity of the bihead to HA. Next, the mix of hBMP7 and IR labeled bihead was injected into mice. hBMP7 only or labeled bihead only was injected as control. At day 20 (24 hrs before sacrifice), another injection of BMP7 was performed. At early time points IR fluorescence was present in the whole body; two weeks later fluorescent signal was difficult to measure in the living mice. However, after sacrifice 3 weeks later, fluorescence was still detectable in the skeleton or organs like liver, spleen and kidneys of group 1 and group 3 mice, which contained labeled bihead. This means the specific accumulation of bihead-IR had occurred at mineralized bones. It is reasonable that the signal of labeled bihead injection mice is weaker compared to labeled MA10 injection mice, since the dose was 4 times lower than that of VHH-MA10-IR. In order to further detect the fluorescent signal location inside bones, microscopic imaging was performed. Most fluorescent signals come from the trabecula, which strongly indicated that the bihead was targeting sites of active bone remodeling.

Immunohistochemistry confirmed the presence of VHH in bone. Half of the mice were injected 1 day before sacrifice with the growth factor BMP7. We performed immunohistochemistry to detect the VHH using an anti-VHH antibody and BMP7 using an anti-BMP7 antibody. As shown in FIG. 6, 20 days after injection of the bifunctional VHH, immunohistochemistry using a rabbit anti-VHH antibody demonstrates the presence of the VHH in mineralized, hydroxy apatite containing bone and cartilage (left panel, brown stain) while no staining was observed in mice that were injected with either BMP7 or with placebo 20 days earlier as expected. When mice were injected with BMP7 in the tail vein 1 day before sacrifice at day 20, immunohistochemistry demonstrated the presence of BMP7 in mineralized bone and cartilage. The BMP7 staining co-localized with the anti-VHH staining. Moreover no BMP7 was found in the mice that were injected with BMP7 or with placebo 20 days earlier. This experiment demonstrates that VHH can be retained in the body when properly targeted to a matrix and that the VHH remain biologically active. This provides evidence that when VHH are conjugated to the backbone of a hydrogel matrix and upon transplantation, they remain biologically active and can still neutralize pro-inflammatory cytokines, growth factors, or growth factor antagonists by binding over a prolonged period of time.

Example 2

Materials

Dextran (Dex; MW 15 to 25 kg/mol-Mn 16 kg/mol; lyophilized before use), 4-nitrophenyl chloroformate (PNC; sublimated before use), LiCl (dried at 110° C. before use), tyramine (TA) anhydrous pyridine, anhydrous N,N-dimethylformamide (DMF), trifluoroacetic acid (TFA), sodium hydroxide (NaOH), N-Boc-1,4-butanediamine (NH2-Boc), sodium bicarbonate (NaHCO3), biotin-atto565, biotin-4-fluorescein (biotin-FITC), 6-aminofluorescein, horseradish peroxidase (HRP, type VI), hydrogen peroxide (H2O2; with inhibitor), fetal bovine serum (FBS), calcein AM, ethidium homodimer-1 (EthD-1), buffered formalin, Triton X-100, and all other solvents were purchased from Sigma-Aldrich. Succinimidyl 6-(biotinamido)hexanoate (biotin-LC-NHS) was purchase from ApexBio. N-hydroxysuccinimide-desthiobiotin (EZ-Link NHS-desthiobiotin) and 4',6-diamidino-2-phenylindole (DAPI) were purchased from Thermo Scientific. Phosphate-buffered saline (PBS) was purchased from Lonza. Minimal Essential Medium a with nucleosides (αMEM), Penicillin and Streptomycin, GlutaMAX, and trypsin-EDTA were purchased from Gibco. Basic fibroblast growth factor (ISOKine bFGF) was purchased from Neuromics. Phalloidin-AF647 was purchased from Molecular Probes. Polydimethylsiloxane (PDMS, Sylgard 184) was purchased from Dow Corning. Aquapel was purchased from Vulcavite. Pico-Surf 1 in Novec 7500 Engineered Fluid and Pico-Break 1 were purchased from Dolomite. Gastight syringes (Hamilton), fluorinated ethylene propylene tubing (FEP, inner diameter 250 μm, DuPont) and connectors were purchased from IDEX Health and Science. Low pressure syringe pumps (neMESYS) were purchased from Cetoni.

Dex-TA-Biotin Synthesis and Characterization

First, dextran was functionalized with tyramine and 1,4-butanediamine, as previously described.[9, 10] In short, dextran was activated with PNC, which was subsequently substituted with tyramine and Boc-protected 1,4-butanediamine and, after using TFA and dialysis using a membrane with 3 kDa molecular weight cut-off, further functionalized with biotin by reacting the Dex-TA-NH2 with a 20-fold excess of biotin-LC-NHS for at least 1 hour in 0.1 M bicarbonate buffer (pH~8.5). Dex-TA-biotin was then purified and concentrated using a spin filter column with 3 kDa molecular weight cut-off. The successful syntheses of Dex-PNC, Dex-TA-NH2, and Dex-TA-biotin were confirmed using 1H NMR (AVANCE III HD NanoBay 400 MHz, Bruker) in DMSO-d6 or D2O. The numbers of conjugated tyramine and butylamine moieties per 100 dextran anhydroglucose rings were determined by calculating the ratios of integrated signals from the dextran ($\delta$ 4.0-5.8 ppm) and the tyramine groups ($\delta$ 6.66 ppm and $\delta$ 6.98 ppm), and those of dextran and the the butylamine groups ($\delta$ 1.4-1.5 ppm), respectively. The number of conjugated biotin moieties per 100 dextran anhydroglucose rings was determined by calculating the ratio of integrated signals from the tyramine groups ($\delta$ 6.66 ppm and $\delta$ 6.98 ppm) and the coupled 6-aminocaproic spacer ($\delta$ 2.13).

Hydrogel Particle Production and Characterization Using Droplet Microfluidics

All microfluidic chips were manufactured from PDMS and glass using standard soft lithography techniques. The microfluidic mixer, droplet generator, and $H_2O_2$ diffusion-based crosslinking chips were fabricated with ~100, ~25 μm, and ~100 μm high channels, respectively. Aquapel was introduced in the chips before usage to ensure channel wall hydrophobicity. Using FEP tubing, chips were connected to each other and to gastight syringes, which were controlled by low-pressure syringe pumps. All emulsions were produced using 2% (w/w) Pico-Surf 1 containing Novec 7500 Engineered Fluid. To generate hydrogel precursor microdroplets, PBS that contained 5% (w/v) Dex-TA-Biotin (~1 mM biotin) and 22 U/ml HRP in PBS, and PBS that contained 5% (w/v) Dex-TA (without biotin) and 22 U/ml HRP in PBS were combined in the microfluidic mixer and subsequently emulsified in the connected droplet generator using surfactant containing oil at a 1:6 flow ratio. The hydrogel precursor microemulsion was flown at a total rate of 14 μl/min through the connected diffusion platform, which was also fed with $H_2O_2$ flowing in opposite direction at a rate of 30 μl/min. The $H_2O_2$ diffused from the feed channel through the PDMS walls into the gel precursor microemulsion, thereby triggering enzymatic crosslinking of tyramine-conjugated polymer, as previously described. [11] The microemulsion was broken by washing three times with surfactant-free fluorocarbon oil and subsequent supplementation of Pico-Break 1 in the presence of PBS that contained 0.05% (w/v) $NaN_3$ for preservation and 1% (w/v) BSA to prevent aggregation and sticking. On-chip droplets were visualized using a stereomicroscope set-up (Nikon SMZ800 equipped with Leica DFC300 FX camera). Retrieved hydrogel particles were imaged using phase contrast microscopy and the size distribution was measured using Matlab software.

Hydrogel Particle Functionalization and Characterization

After washing Dex-TA-biotin Hydrogel particles three times with excessive washing buffer that consisted of 1% (w/v) BSA in PBS to remove $NaN_3$, they were consecutively incubated with 1 μM neutravidin in washing buffer, washed with washing buffer, incubated with 1 μM biotinylated or desthiobiotinylated molecule of interest in washing buffer, and washed again with washing buffer. If necessary, the functionalization protocol was repeated, for example, to create core-shell functionalized hydrogel particles, as further specified in FIG. 7. For fluorescence microscopy (EVOS FL), fluorescence confocal microscopy (Zeiss LSM 510 and Nikon A1+), and fluorescence recovery after photobleaching (FRAP; Zeiss LSM 510), the hydrogel particles were functionalized with biotin-atto565, biotin-FITC, and/or desthiobiotin-FITC that was produced in house by coupling desthiobiotin-NHS to 6-aminofluorescein in 1 M bicarbonate buffer (pH~8). The FRAP curve was obtained by plotting, as a function of time, the fluorescent intensity of the bleach spot minus the background normalized for the bleach-rate corrected average intensity before bleaching, where the bleach rate was determined by normalizing the sample's fluorescent intensity besides the bleach spot normalized for its average intensity before bleaching. To characterize the desthiobiotin-biotin displacement, Dex-TA-biotin hydrogel particles were consecutively functionalized with neutravidin, washed, functionalized with desthiobiotin-FITC, washed, and functionalized with biotin-atto565, while imaged using fluorescence confocal microscopy, as described above. Intensities of all fluorescent images were measured using ImageJ software.

Cell isolation and expansion. Human mesenchymal stem cells (MSCs) were isolated from fresh bone marrow samples and cultured as previously described.[12] The use of patient material was approved by the local ethical committee of the Medisch Spectrum Twente and informed written consent was obtained for all samples. In short, nucleated cells in the bone marrow aspirates were counted, seeded in tissue culture flasks at a density of 500,000 cells/cm$^2$ and cultured in MSC proliferation medium, consisting of 10% (v/v) FBS, 100 U/ml Penicillin and 100 µg/ml Streptomycin, 1% (v/v) GlutaMAX, 0.2 mM ascorbic acid, and 1 ng/ml bFGF (added fresh) in αMEM. When cells reached near confluence, the cells were detached using 0.25% (w/v) Trypsin-EDTA at 37° C. and subsequently subcultured or used for experimentation.

Figure 7:
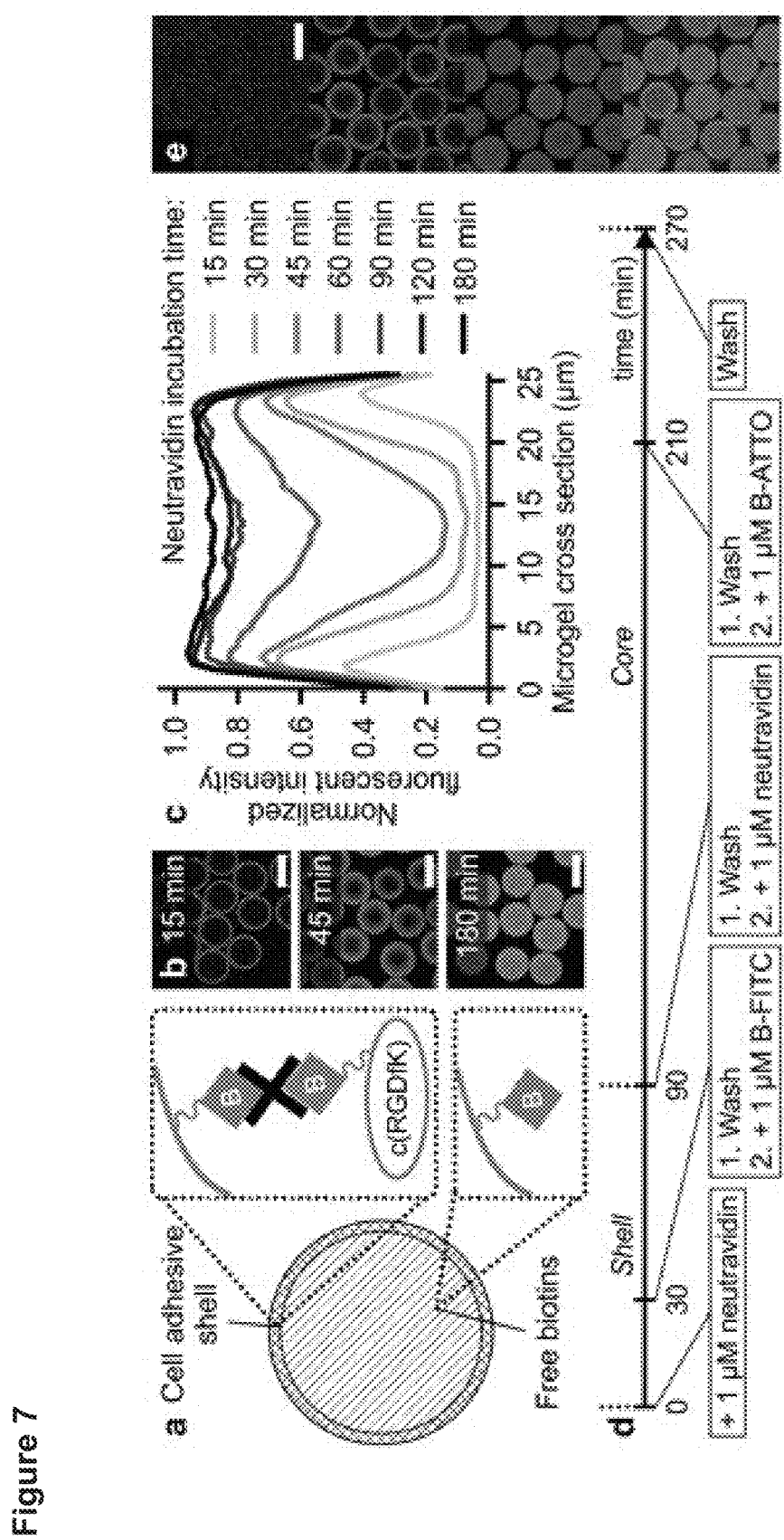
FIG. 7: (a) Dex-TA-biotin microgels functionalized with a shell (e.g. RGD-type peptides), while the biotin moieties in the cores remained free, which allowed for further in situ functionalization of the modular microtissues. (b,c) The thickness of the functionalized shells could be controlled by the diffusion of neutravidin, which acted as a reactive substrate for biotinylated moieties. (d) Using this facile multistep functionalization protocol, the shells and cores of Dex-TA-biotin microgels could be endowed with distinct functional moieties, (e) as demonstrated using FITC-(i.e. green) and atto565-labeled (i.e. red) shells and cores, respectively. Such core-shell type functionalization can be leveraged, amongst others, to physically separate functional moieties in the core from the microgel exterior, by engineering a non-functionalized or alternatively functionalized shell. Black scale bars: 100 μm. White scale bars: 20 μm.

Modular tissue engineering. To produce modular tissue constructs, the shells of Dex-TA-biotin microgels that contained ~1 mM biotin were first permanently functionalized with c(RGDfK) peptide. To this end, the microgels were incubated for 30 minutes with 1 µM neutravidin in washing buffer (see previous section 'microgel functionalization and characterization'), washed, and subsequently incubated for 60 minutes with 1 µM biotinylated cyclic RGD peptide biotin-(PEG)$_2$-c(RGDfK) in washing buffer, as also depicted in FIG. 7. Dex-TA (i.e. without biotin) microgels that had been treated with the same functionalization protocol and Dex-TA-biotin microgels that had been functionalized with biotin-(PEG)$_2$-c(RADfK) were used as controls. The cell adhesive microgels were then co-seeded with cells into non-adherent microwell chips that were produced by casting 3% (w/v) sterile agarose in demineralized water on an in-house fabricated mold, as previously described.[13] In short, MSCs and microgels were homogenously seeded into agarose constructs (1.9 cm$^2$) containing 3000 microwells (200×200×200 µm) at a seeding density of 50 units (i.e. cells+gels) per microwell. The modular microtissues were cultured in proliferation medium and visualized using fluorescence (confocal) microscopy. C2C12BRA experiment. Viability and metabolic activity of cells was analyzed by staining with 2 µM calcein AM (live) and 4 µM EthD-1 (dead) in PBS and visualization using fluorescence microscopy. For additional fluorescent (confocal) analyses, constructs were first washed with PBS, fixated using 10% neutral buffered formalin, permeabilized using 0.1% Triton X-100 and subsequently incubated for 30 minutes with 2.5 U/ml phalloidin-AF647 and 1 µg/ml DAPI to stain F-actin and nuclei, respectively.

Statistics: The microgel size distribution was obtained by measuring the diameters of ≥275 microgels. The fluorescent confocal intensity measurements (except for FRAP measurements) were performed on ≥5 microgels per condition and reported as the average (cross sections of neutravidin diffusion experiment) or the average±standard deviation (all other experiments) normalized for the highest average intensity. Cell seeding distributions were obtained by artisan counting of cells and microgels in ≥20 microwells per condition and reported as the average±standard deviation normalized for the total average number of units (cells+microgels) per microwell. The diameter, area, circularity, and solidity of modular microaggregates were obtained from ≥10 constructs using the 'area' and 'shape descriptor' measurement functions of ImageJ and reported as the average±standard deviation. Linear regression analyses and AVOVA with Bonferroni's post hoc tests to analyze statistical significance were performed using OriginPro software.

Results

We set out to engineer micrometer-sized hydrogel particles (microgels) that could be biochemically tuned in a cytocompatible fashion. To this end, dextran was selected as a bio-inert, biocompatible, and easily modifiable polymer backbone, thereby acting as a perfect template material for further functionalization.[14, 15] Tyramine and biotin were selected as reactive side groups that could be enzymatically crosslinked and further functionalized via biotin/avidin interaction, respectively,[10, 16, 17] in a fully orthogonal and cytocompatible manner. The dextran polymer was endowed with tyramine and 1,4-butanediamine (i.e. Dex-TA-NH$_2$), as previously described,[9, 10] which was then further functionalized using amine-reactive biotin, which contained a long-chain spacer (biotin-LC-NHS). Successful Dex-TA-biotin synthesis was confirmed using $^1$H NMR. The numbers of conjugated tyramine and biotin moieties per 100 dextran anhydroglucose rings were 13 and 6, respectively, as determined by calculating the ratios of integrated signals from the dextran (δ 4.0-5.8 ppm) and the tyramine (δ 6.66 ppm and δ 6.98 ppm) and those of tyramine and the coupled 6-aminocaproic spacer (δ 2.13). Tyramine-functionalized dextran could be crosslinked in situ via the formation of tyramine-tyramine bonds using horseradish peroxidase (HRP) as a catalyst and H$_2$O$_2$ as an oxidizer. A microfluidic droplet generator was used to generate microdroplets composed of 5% (w/v) Dex-TA-biotin (i.e. ~1 mM biotin) and 22 U/ml HRP. These microgel precursor droplets were cured by controlled supplementation of H$_2$O$_2$ using a diffusion-based microfluidic crosslinking platform that we have recently reported.[11] This resulted in the formation of monodisperse Dex-TA-biotin microgels with a diameter of 20.7±0.6 µm.

After enzymatic crosslinking, the biotin moieties remained available for subsequent orthogonal functionalization (i.e. without affecting the enzymatically crosslinked hydrogel network) via supramolecular biotin/avidin complexation. Specifically, the biotinylated microgels were further functionalized using a two-step approach by incubating them with tetravalent neutravidin (i.e. an avidin analog) and fluorescein-labeled biotin (biotin-FITC), respectively. Fluorescence confocal microscopy and fluorescence recovery after photobleaching (FRAP) confirmed that biotin-FITC was coupled to Dex-TA-biotin microgels, but not to non-functionalized (i.e. Dex-TA) microgels, which validated the successful generation and functionality of Dex-TA-biotin microgels. The final degree of functionalization could be tuned by changing either the concentration of biotin in the microgels or the type and amount of biotinylated functional groups that were coupled via tetravalent neutravidin. To control the biotin concentration in the microgels, we varied the ratio of Dex-TA-biotin and Dex-TA hydrogel precursor solution using a microfluidic mix chip that was connected to the inlet of the droplet generator. The biotin concentration in the resulting microgels linearly correlated ($R^2$=0.99) to the final degree of functionalization, as measured by coupling either biotin-FITC (i.e. green) or biotin-atto565 (i.e. red) to the microgels. Alternatively, the biochemical composition could be altered by varying the ratio of biotinylated FITC and atto565, while maintaining the same concentration of biotin in the microgels. In principle, both methods could be applied to tune the microgels' biochemical properties without altering their biomechanical properties.

We then aimed to create smart microgels that could reversibly and sequentially present molecules of interest. To this end, we leveraged the reversible nature of the supramolecular desthiobiotin/avidin complex by displacing desthiobiotin with biotin in a rapid and highly specific manner. Microgels were first endowed with an abundant amount of neutravidin, which specifically bound to the free biotins in the microgels ($K_d\sim10^{-15}$). The microgels were then washed (t=0 min) and continually imaged using fluorescence confocal imaging to visualize and quantify the desthiobiotin binding and displacement in time. The neutravidin-labeled microgels were incubated with 1 µM desthiobiotin-FITC (i.e. green), which could bind to the remaining free binding pockets of the tetravalent neutravidin in the microgels ($K_d\sim10^{-13}$). After the fluorescent intensity had reached a plateau (t~40 min), biotin-atto565 (i.e. red) was introduced to a final concentration of 1 µM. Biotin interacted more strongly with neutravidin ($K_d\sim10^{-15}$), which resulted in a rapid displacement of desthiobiotin by biotin. Over 80% of the desthiobiotin-FITC was replaced by the biotin-atto565 within the first 10 min after biotin addition and approximately 95% was replaced within 60 min.

Figure 8:
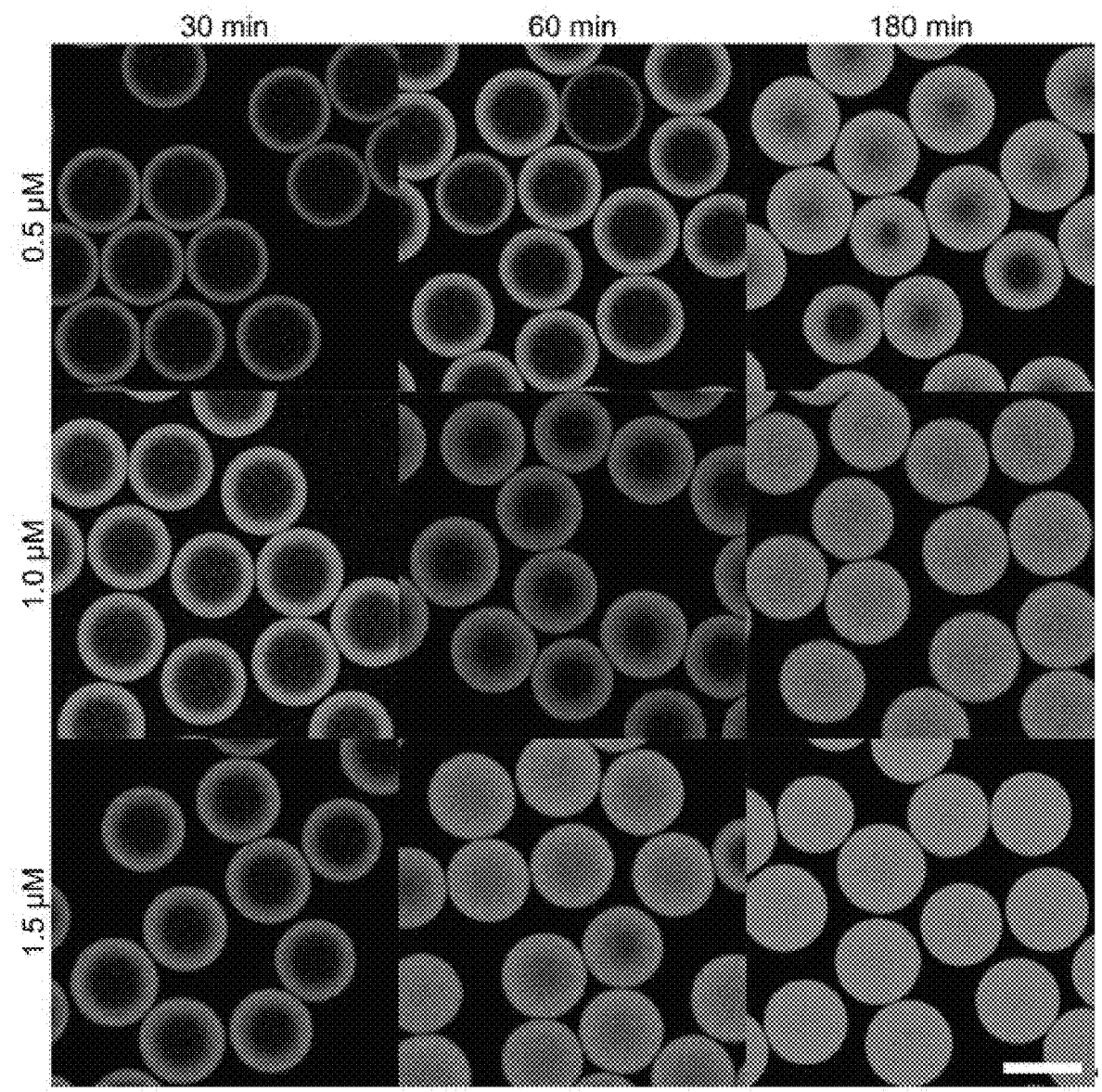
FIG. 8: Controlling functionalized shell (i.e. second polymer network) thickness. Scale bar: 20 μm.

We aimed to endow the microgels with a permanent and spatially controlled shell (i.e., the second polymer network). Specifically, we anticipated that functionalizing the microgel's shell with biotinylated cyclic RGD peptide biotin-(PEG)$_2$-c(RGDfK) would enable the microgels to self-assemble with cells, while leaving the biotins in the microgel's core available for further in situ functionalization (FIG. 7), thereby sequestering the molecules in the core from the particle's environment, while providing a secondary function to the shell. By tuning the concentration and incubation time of neutravidin, we could reproducibly control its penetration depth into the microgels. This strategy granted 2.5D control over the microgel's biochemical composition by determining the thickness of the neutravidin shell, which acted as the reactive substrate for subsequent coupling of biotinylated molecules. This diffusion-based spatial templating was visualized and quantified using biotin-FITC (i.e. green) labeling and subsequent fluorescence confocal imaging (FIG. 7 and FIG. 8). After shell functionalization, the microgels' cores still contained free biotins that could be endowed with another moiety by repeating the functionalization protocol with a prolonged neutravidin incubation step. For example, core-shell multifunctional microgels could be readily prepared by applying a shell functionalization using the multistep functionalization protocol as described in FIG. 7. After confirming the effectiveness of the core-shell functionalization protocol using fluorescent labels (FIG. 7), the same core-shell functionalization strategy was used to permanently endow the microgels' shells with c(RGDfK) peptides to enable integrin-mediated cell adhesion and promote bottom-up self-assembly. The concentration of biotin and consequently c(RGDfK) in the microgels was set to ~1 mM, as this has been proven to be effective to render hydrogels with cell adhesive properties.[18, 19]

Dex-TA-biotin hydrogel particles could be endowed with a functional shell of tunable thickness by controlling the concentration and incubation time of neutravidin. In fact, the neutravidin acted as a template for subsequent tethering of biotinylated molecules of interest, as demonstrated using biotin-FITC (i.e. green: FIG. 8).

Alternatively, the shell can be functionalized/protected post hydrogel particle production via polymerization of tyramine moieties that are available on the hydrogel particles' surface.

Figure 9:
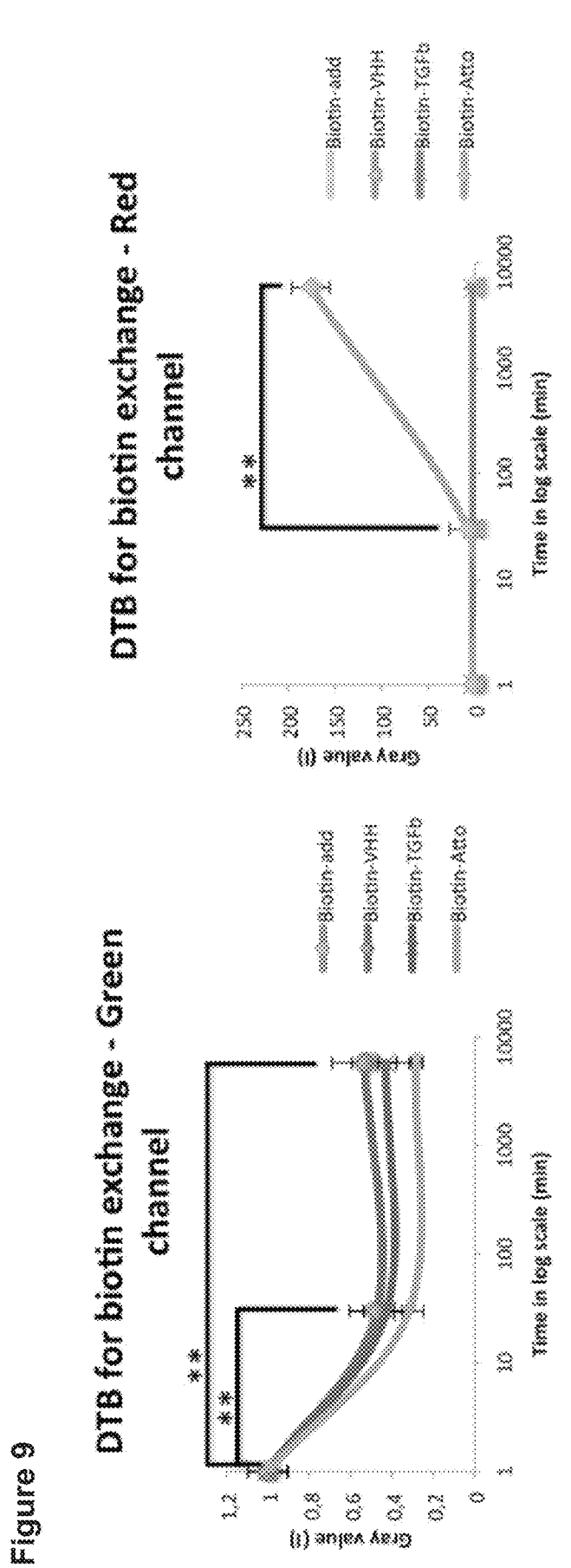
FIG. 9: Fluorescently-labeled desthiobiotin (DTB-FITC) that is coupled to dextran-tyramine microgels using tetravalent neutravidin is replaced by various biotinylated molecules of interest, including biotin-VHH@BMP7, which demonstrates the successful functionalization of chemically crosslinked microgels using host-guest (i.e. physical) interactions.

Using a desthiobiotin(DTB)/biotin displacement strategy, we have demonstrated that biotinylated single-domain antibodies (VHH) can be bound to dextran-tyramine-biotin hydrogel particles (FIG. 9). We have coupled a genetically modified VHH via a biotin linker to a previously crosslinked and functionalized dextran-based hydrogel. Besides conjugates introduced for crosslinking individual dextran polymers, these molecules also contain a biotin conjugate (FIG. 9). Using streptavidin (or an alike molecule) as a multivalent (typically tetravalent)intermediate the biotinylated VHHs are attached to the polymer backbone in a supramolecular interaction.

To enable directed coupling, a free Cys has been introduced in the C-terminal tail of the VHH to which the biotin molecule is conjugated using maleimide chemistry. Using this free Cys the VHHs can also be directly coupled to a susceptible reactive group introduced at the dextran backbone.

Figure 10:
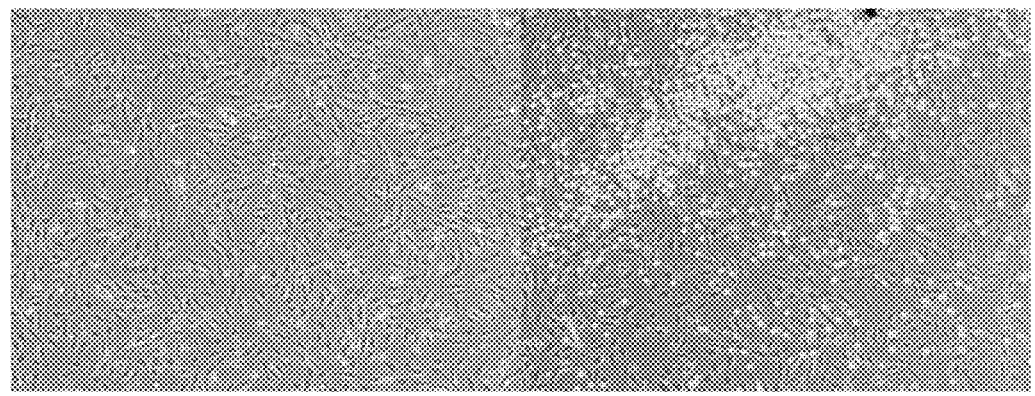
FIG. 10: Human mesenchymal stem (stromal) cells cultured without (left hand panel) and with dextran-tyramine microgels (right hand panel). The microgels are visible as white dots. The microgels (i.e. 'cytokine sinks') do not affect in vitro cell culture as indicated by unaffected cell morphology.
Figure 11:
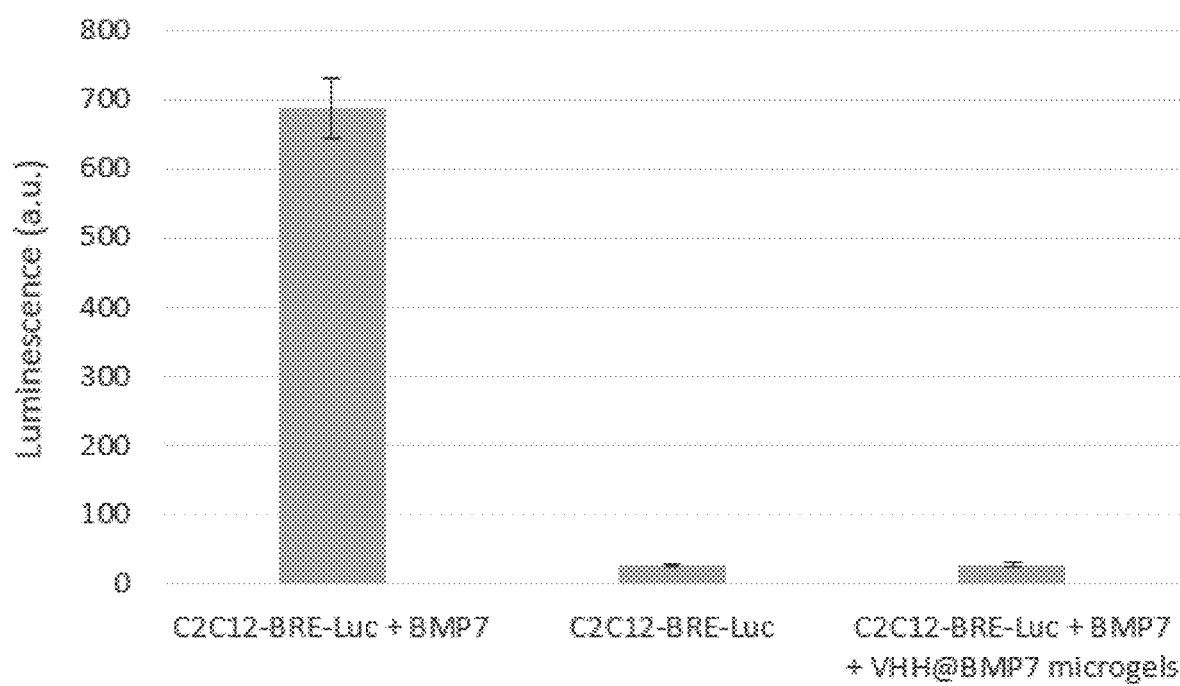
FIG. 11: In vitro luciferase production of the BMP reporter cell line (C2C12-BRE-Luc) in response to BMP7, with and without dextran-biotin microgels functionalized with VHH@BMP7 'cytokine sinks'). The VHH-functionalized microgels can prevent cell response by depleting growth factors (i.e. cytokines) from the local environment.

VHH-functionalized hydrogel particles can prevent cell response by depleting growth factors (i.e. cytokines) from the local environment (see FIG. 10 and FIG. 11). Materials and Methods: C2C12 BRE Luciferase cells were seeded at 10.000 cells/cm2 in growth medium (DMEM, 20% FBS, 1% Penicillin and Streptomycin). After 24 hours, the cells were starved for 12 hours in growth medium containing 0.5% FBS. Starvation was followed by 10-15 hours stimulation in starvation medium with BMP7 (R&D systems, 300 ng/ml). Prior to addition of hydrogel particles to the cell culture, the hydrogel particles were incubated for 1 h in 10% FBS, to block nonspecific binding. Simultaneously with the BMP7, hydrogel particles were added in a 10-fold excess. After stimulation cells were lysed and the luciferase expression was determined using manufacturers protocol (Promega, Luciferase Assay System).

Figure 12:
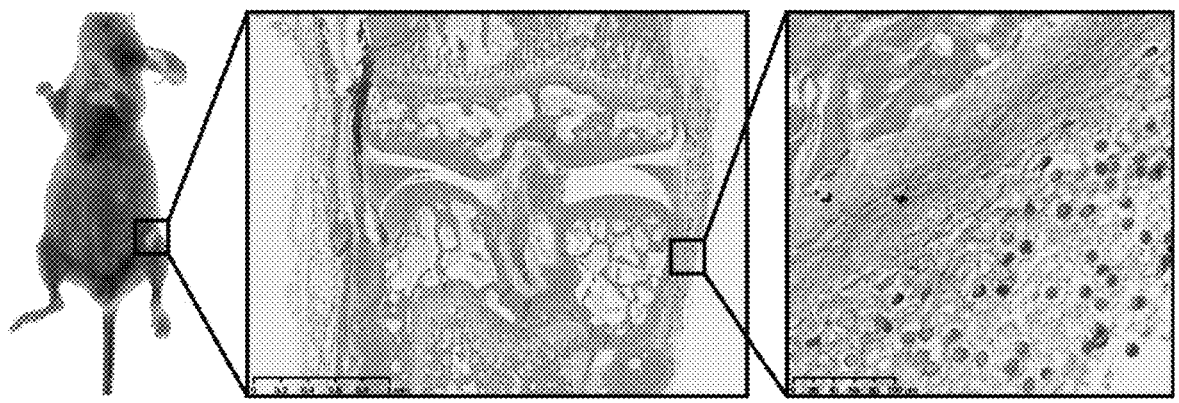
FIG. 12: From left to right panel a, b and c. Microgels of 30 μm in diameter were prepared using near-infrared-labelled Dextran conjugates and injected in the synovial cavity of a mouse knee. (a) After three weeks, the microgels could still be traced in live animals using fluorescent imaging showing that the microgels were still present in the injected knee, and (b, c) post mortem using histological staining. Microgels end up in the synovial membrane visible as the dark purple dots at the left side of panel c.

Long-term retention of hydrogel microparticles after intra-articular injection was also demonstrated. Microgels of 30 µm in diameter were prepared using near-infrared-labelled dextran conjugates and were injected in the synovial cavity of a mouse knee. After three weeks, the microgels could still be traced in live animals using fluorescent imaging showing that the microgels were still present in the injected knee, and post mortem using histological staining (FIG. 12). Microgels end up in the synovial membrane visible as the dark purple dots at the left side of panel c (FIG. 12).

In certain applications, the displacement of a desthiobiotinylated molecule by a biotin or biotinylated molecule can be used for the on-demand and/or controlled release of the desthiobiotinylated molecule to, e.g. switch off its local function or achieve its on-demand and/or controlled release.

Example 3

Permeability

The permeability of the hydrogel networks was tested using FITC-conjugated dextran with molecular weights of 20, 40, 70, 150, 500 and 2000 kDa (Sigma-Aldrich) and immunoglobulin G (IgG, 150 kDa, Sigma-Aldrich). Confocal cross-sections were made and the fluorescence intensity in the center of the gel was compared with the fluorescence intensity of the background using a custom made Matlab script. A minimum of 50 gels per condition were analyzed.

Figure 13:
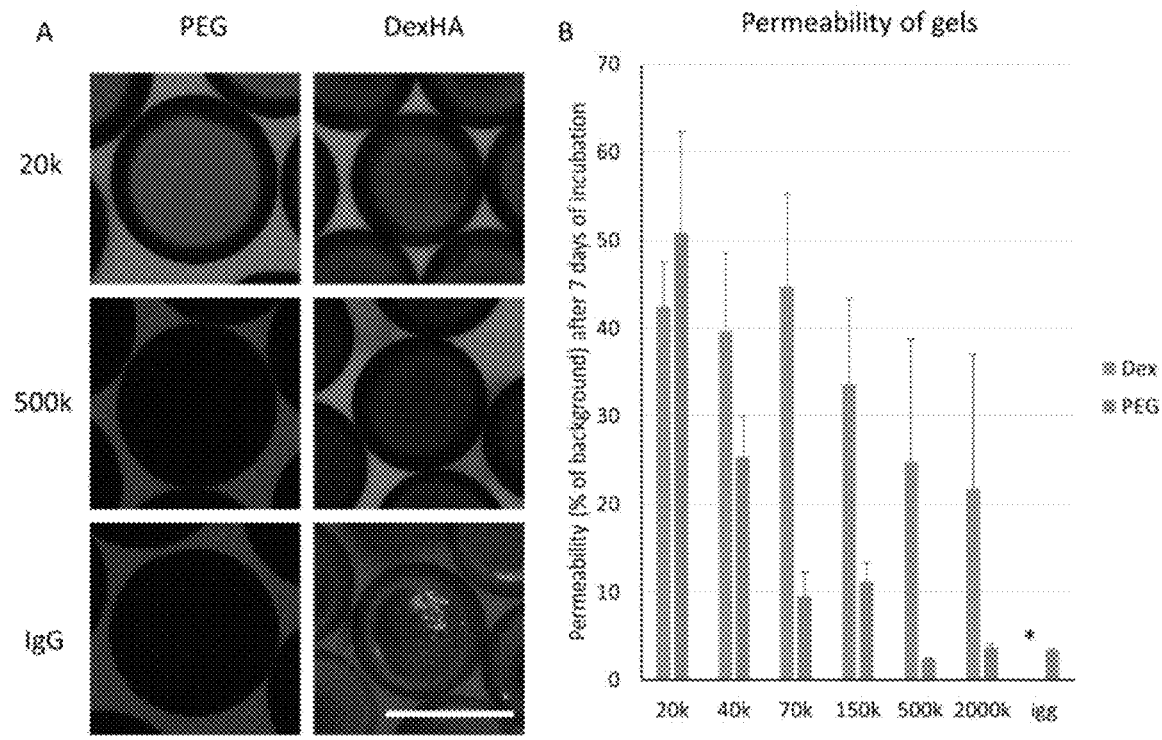
FIG. 13: A) Confocal slices of hollow PEG-TA (indicated with PEG) and DexHA-TA (indicated with DexHA or Dex) microgels incubated with FITC conjugated dextrans with different molecular weights (20 kDa, 40 kDa, 70 kDa, 150 kDa, 500 kDa, 2000 kDa) and IgG. Scale bar represents 250 μm. B) Quantification of the microgels' permeability by digital image analysis of the confocal images from panel A. The molecular weights and hydrodynamic radii of the assessed molecules are [20 kDa dextran-FITC, 40 kDa dextran-FITC, 70 kDa dextran-FITC, 150 kDa dextran-FITC, 500 kDa dextran-FITC, 2000 kDa dextran-FITC, 150 kDa IgG] and [~3.3 nm, ~4.5 nm, ~5.8 nm, ~8.5 nm, ~147 nm, ~27.0 nm, 5.3 nm], respectively. *DexHA(-tyramine) gels are permeable to IgG, but quantification was impossible due to IgG precipitation in the core of the gel. k indicates kilodalton (kDa).

Analysis showed that DexHA-TA capsules were permeable for all FITC conjugates up to 2000 kDa and IgG (FIG. 13) although diffusion is approximately 50% delayed for larger molecules. This suggests that DexHA-TA based micro hydrogels are permeable, and most likely permeable to almost all relevant molecules in vivo, including large proteins but diffusion might be hampered. Quantification of IgG penetration in DexHA-TA was impossible due to IgG precipitation in the core of the gel. The PEG-TA capsules, however, were only permeable up to FITC conjugates of 150 kDa, Based on the fluorescence intensity of the core in PEG-TA capsules incubated with dextran>500 k and with IgG which were around back ground levels, diffusion of large molecules appeared severely jeopardized in these capsules (FIG. 13).

Example 4

In addition to the indirect coupling of an antibody fragment or peptide via the biotin-streptavidin-biotin interaction, additional methods were explored for the direct and targeted coupling of biological molecules to the backbone of tyramine functionalized polymers like Dex-TA and HA-TA.

Figure 14:
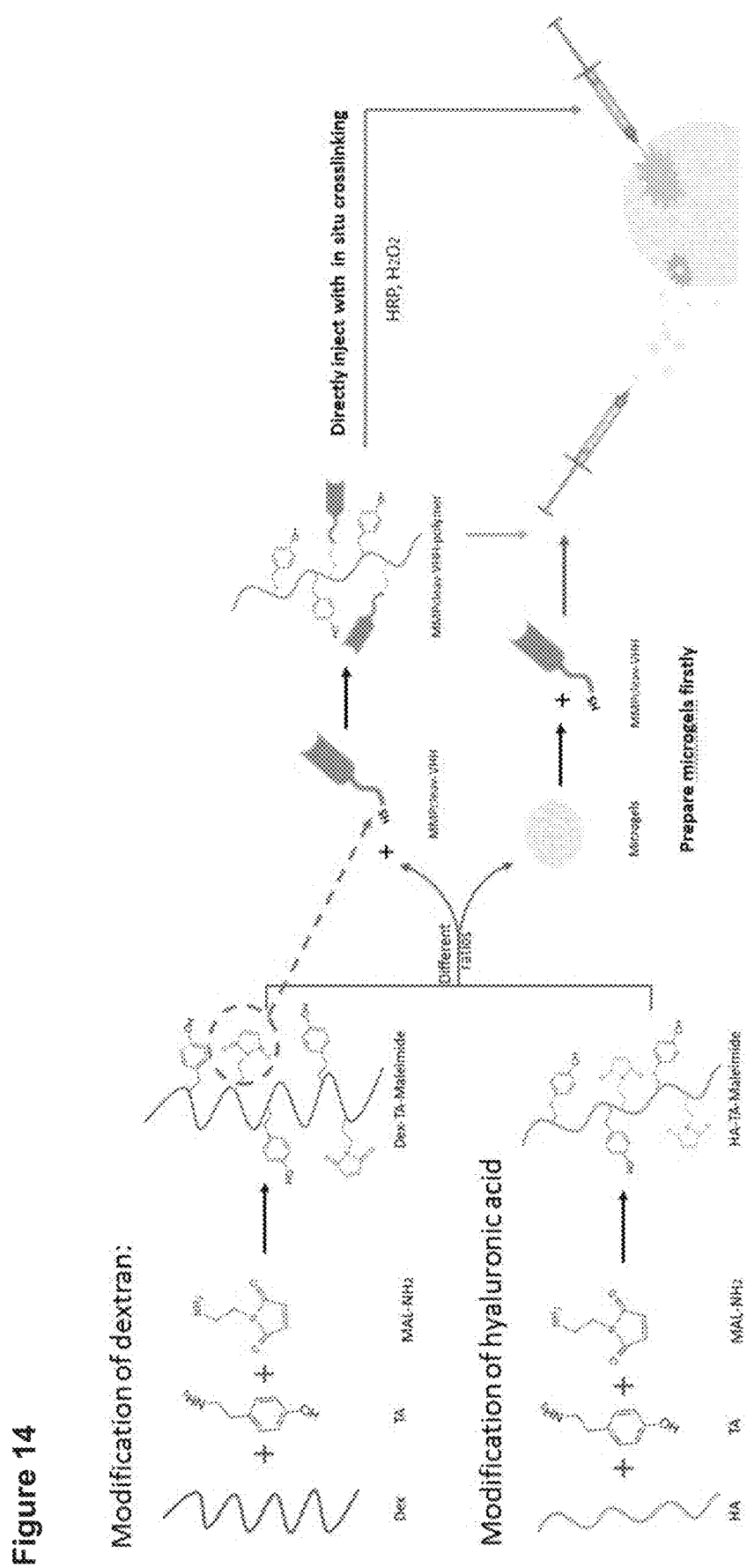
FIG. 14: Modification of DEX and HA. Schematic representation showing the modification of Dex and HA. We synthesize dextran conjugated to tyramine and mal-amine, and then use this polymer to react with free thiol group. Polymer VHH conjugates could be directly injected with in situ crosslinking or first be processed in microgels, and then loading VHH. The thus prepared microgels can be injected into the joint space. Polymer VHH conjugates could be directly injected with in situ crosslinking or be first processed in microgels that could be injected.

A general method to obtain cytokine sinks that can be injected intra-articularly in the joint is given in FIG. 14. In short, reactive maleimide groups are conjugated to the backbone of polymer-tyramine conjugate. In this way Dex-TA-maleimide and HA-TA-maleimide polymer conjugates are obtained. Subsequently two methods can be followed. In the first method, antibody or peptide fragments with a free unpaired cysteine residue are reacted with the maleimide groups at the polymer-TA backbone. This creates polymer-TA-protein conjugates. These conjugates can be used for direct injection at the injection site, such as the joint space, in combination with horse radish peroxidase and minute amounts of hydrogen peroxide. This enables in situ micro- and macro-gel formation at the injection site such as the joint space. Alternatively, the polymer-TA-protein conjugates can be used to first generate microgels as described for the dex-TA-biotin polymers. Thus generated microgels can be directly injected in the joint space. In a further method, the polymer-TA-maleimide conjugates are first used for microgel formation after which specific binding molecules with a free unpaired cysteine residue are allowed to diffuse in the microgel network and react with the maleimide residues at the polymer backbone.

Figure 15:
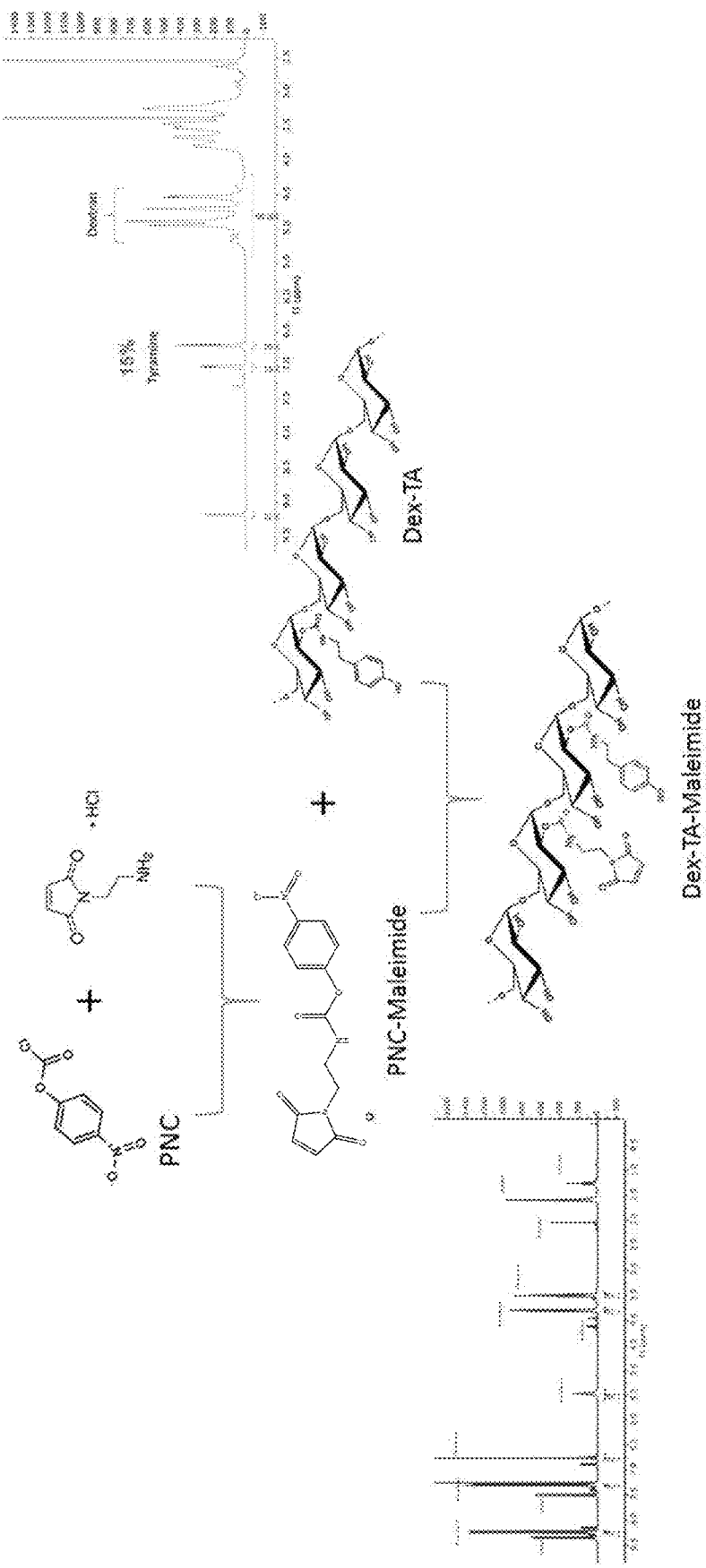
FIG. 15: Schematic representation of the activation of N-(2-Aminoethyl)maleimide Hydrochloride with PNC (confirmed by 1H-NMR). Subsequent reaction with Dex-TA yielded Dex-TA-Maleimide.
Figure 16:
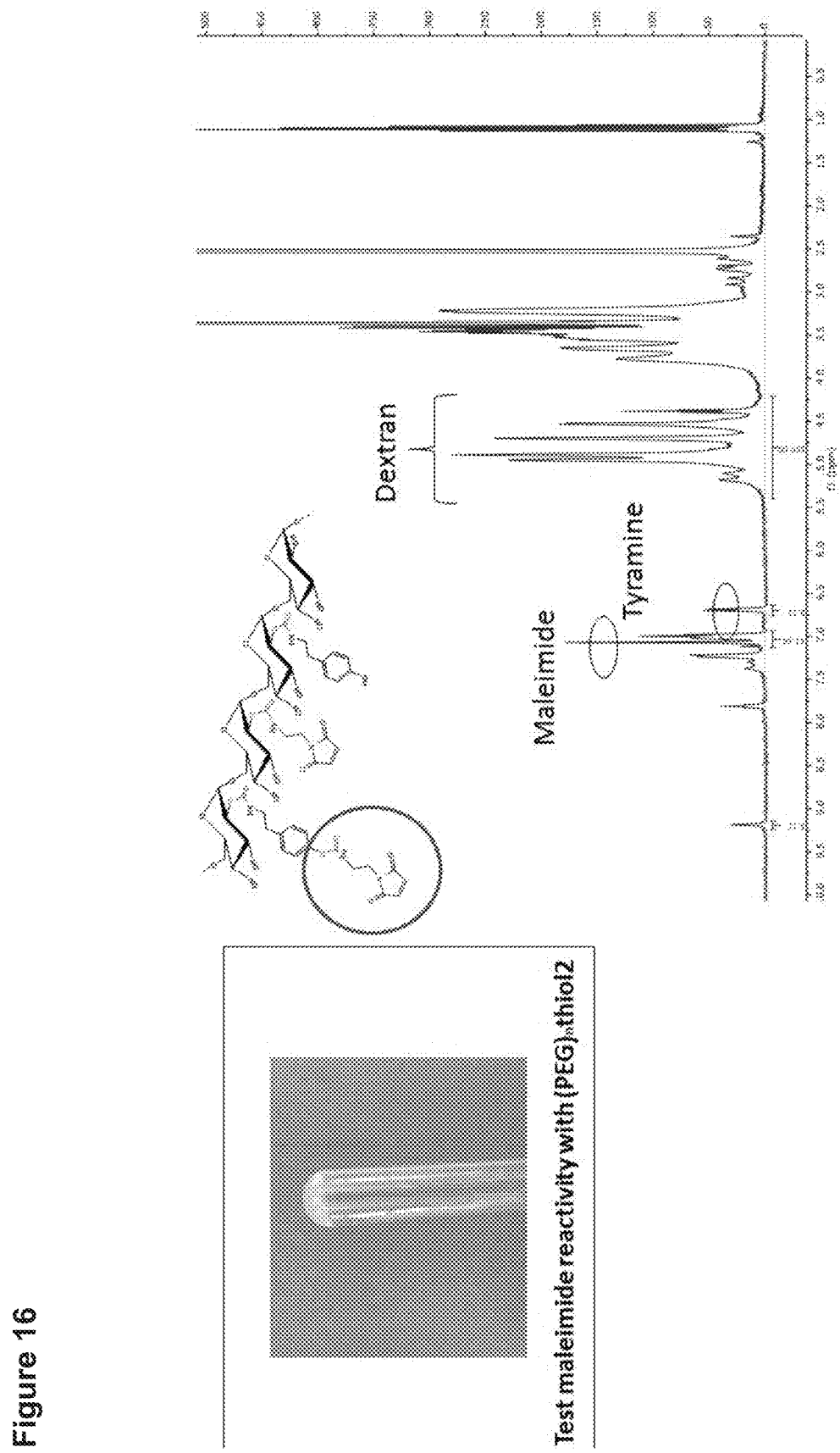
FIG. 16: $^1$H-NMR analysis of the product confirmed the structure of Dex-TA-Maleimide. The majority of the Mal-PNC reacted with the phenolic residues present op de Dex-TA. The peaks used for quantification are indicated in the spectrum. The left inset shows the crosslinked product of Dex-TA-Maleimide with PEG-dithiol, confirming the reactivity of the maleimide residues in the product.

Two methods were used to introduce maleimide and tyramine residues in the backbone of Dextran. First, a maleimide-PNC intermediate was formed. This intermediate was subsequently reacted with Dextran-tyramine conjugates (FIG. 15). As shown in FIG. 16, Dex-TA-maleimide conjugates were obtained. Besides that, the maleimide-PNC intermediate also reacted with phenolic residues (left hand circle). The maleimide groups were still functional as demonstrated by rapid gel formation once the polymer conjugates were mixed with poly(ethylene glycol) dithiol groups as expected. Thus prepared Dex-TA-Maleimide conjugates can be used for reacting with peptides and proteins with a free-Cysteine.

Figure 17:
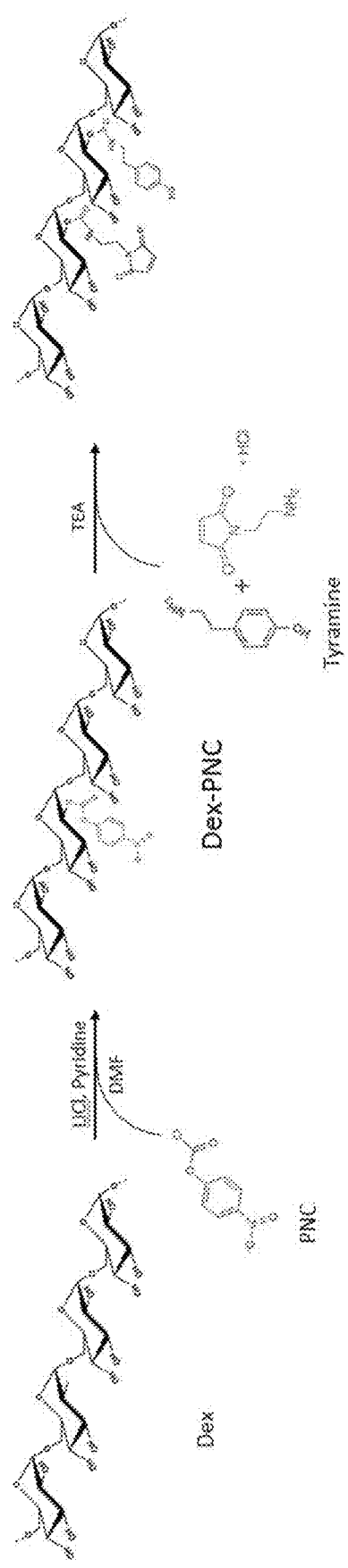
FIG. 17: Reaction scheme of alternative synthesis of Dex-TA-Maleimide by activation of Dextran with PNC, Dex-PNC was subsequently reacted with a mixture of tyramine and a maleimide-amine yielding Dex-TA-Maleimide.
Figure 18:
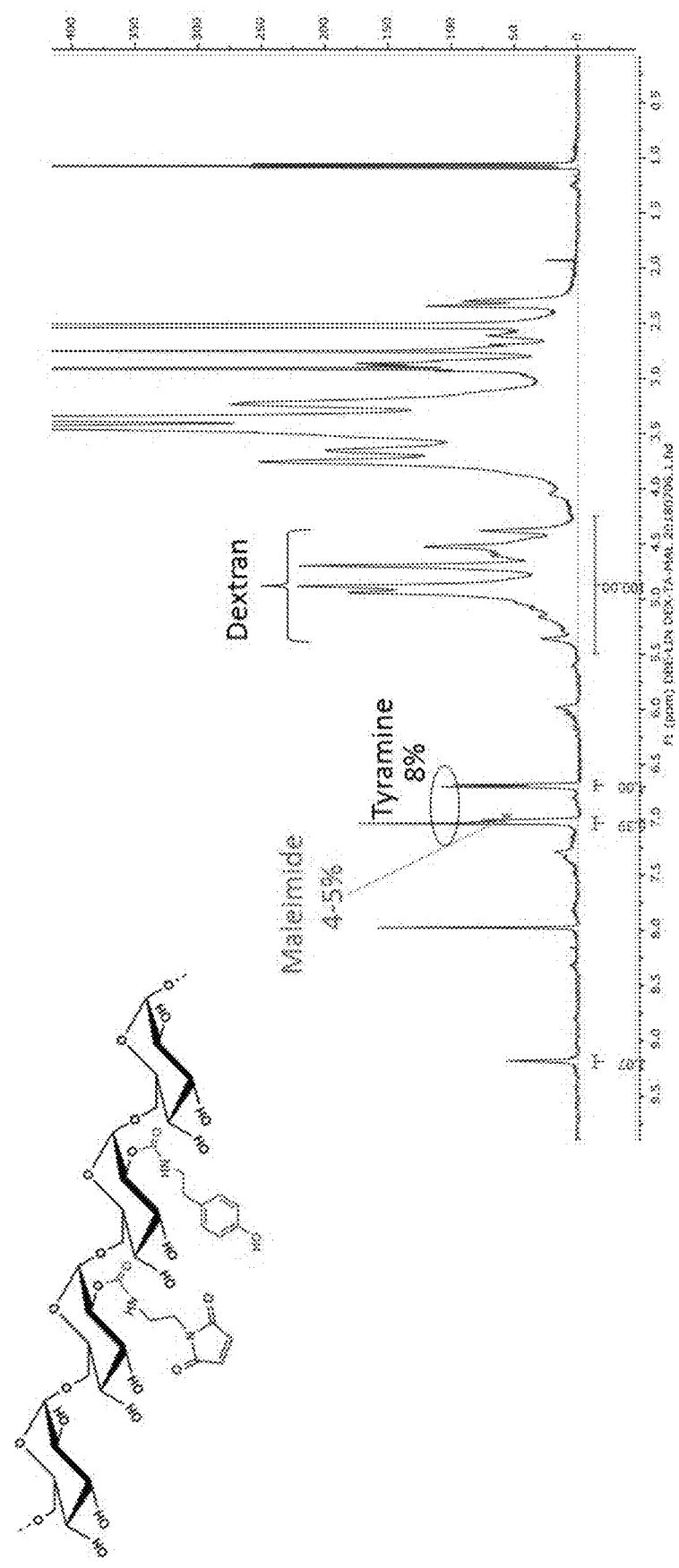
FIG. 18: $^1$H-NMR analysis of the product confirmed the structure of Dex-TA-Maleimide. The peaks used for quantification are indicated in the spectrum.

In a second method, Dextran was first reacted with PNC to obtain a Dex-PNC intermediate conjugate. Dex-PNC was subsequently reacted with a mixture of tyramine and a maleimide-amine (FIG. 17). In FIG. 18, it is shown that this method resulted in Dex-TA-maleimide conjugates with a degree of substitution of 8% for tyramine and 4-5% for maleimide (FIG. 18).

Figure 19:
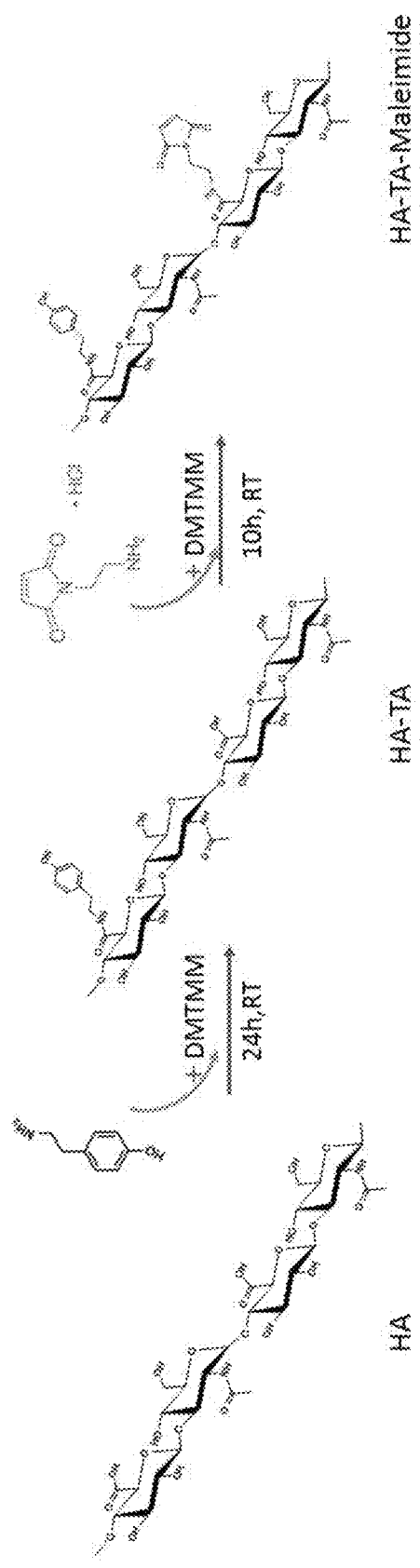
FIG. 19: Reaction scheme of the functionalization of Hyaluronic acid with tyramine and maleimide in the presence of DMTMM.
Figure 20:
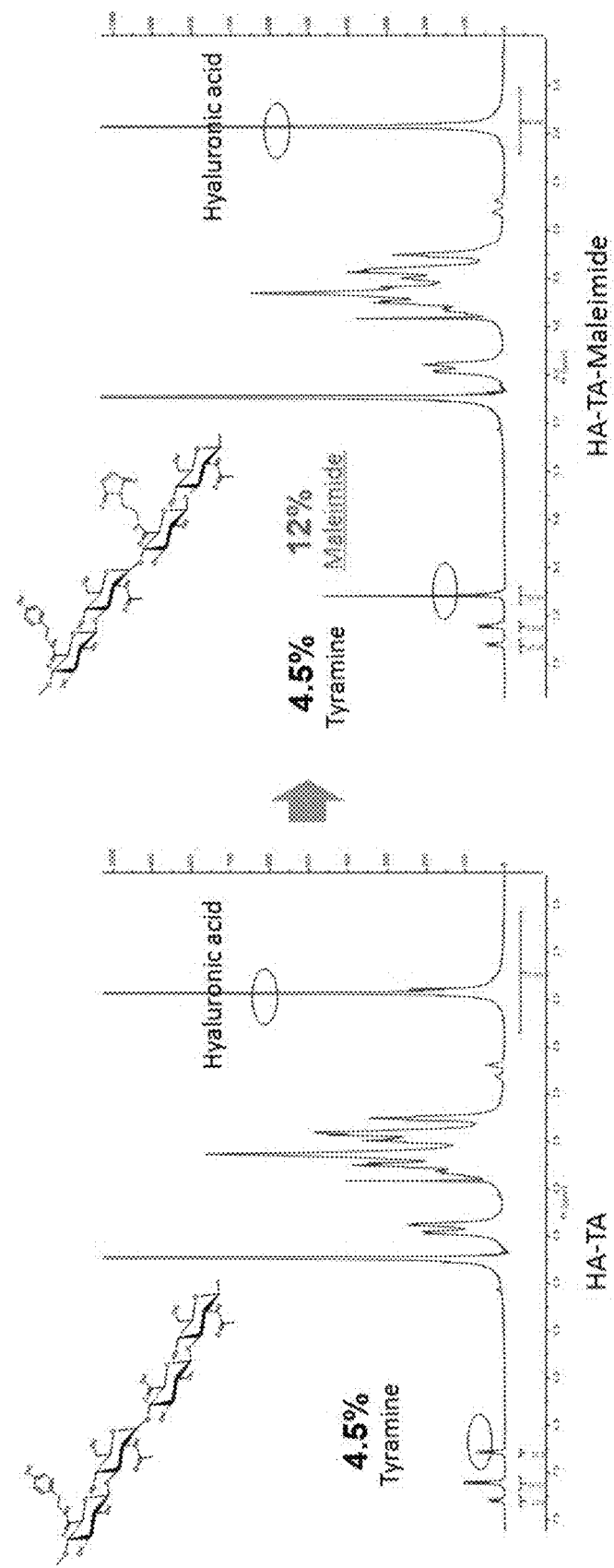
FIG. 20: $^1$H-NMR analysis of the product confirmed the structure of HA-TA-Maleimide. The circled areas indicate the signals used for the quantification of the tyramine and maleimide residues.

To obtain hyaluronic acid (HA) tyramine-maleimide conjugates a two-step reaction was used. Hyaluronic acid was first reacted with tyramine in the presence of DMTMM resulting in the formation of HA-TA. Subsequently, HA-TA was reacted with maleimide-amine again in the presence of DMTMM (FIG. 19). This resulted in HA-TA conjugates with a degree of substitution of TA of 4.5% which was subsequently modified with maleimide functional groups at a degree of substitution of 12% (FIG. 20).

Figure 21:
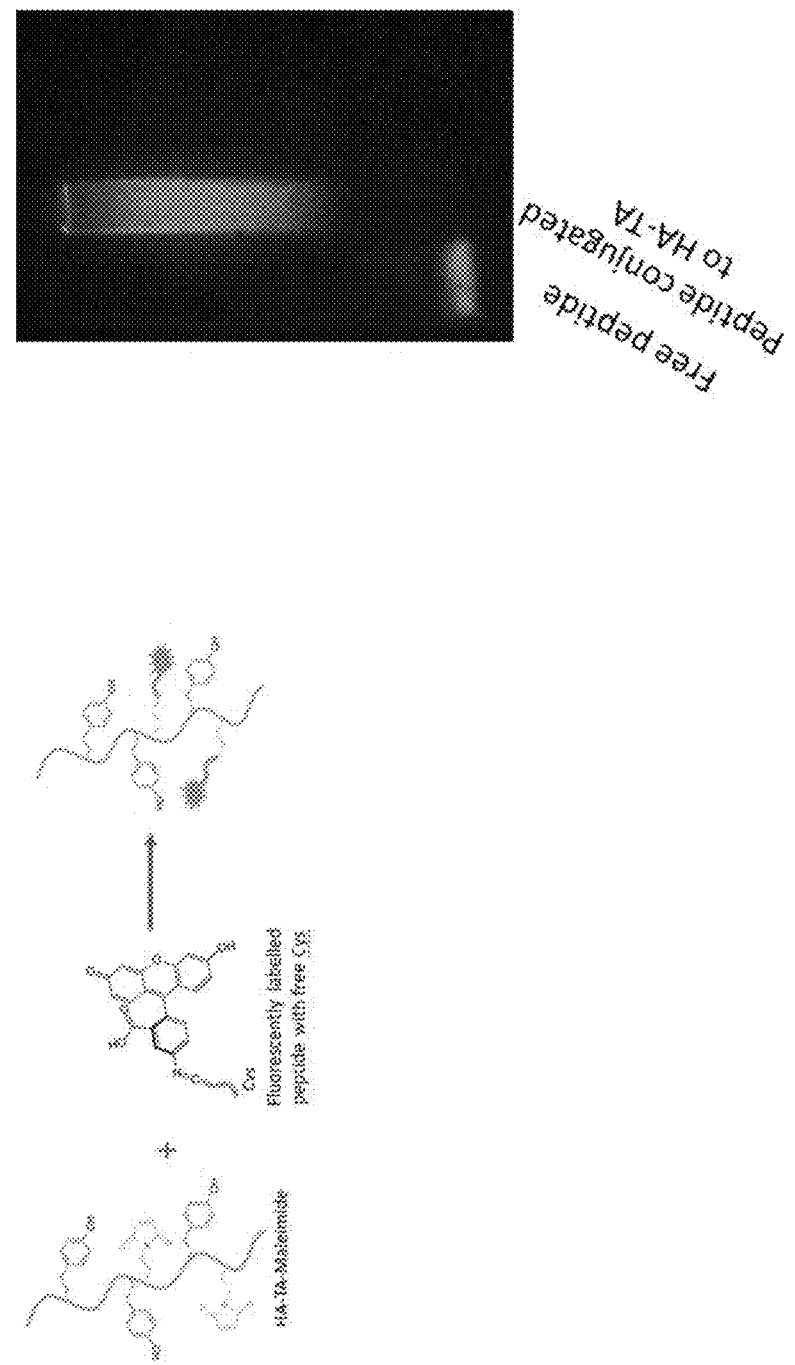
FIG. 21: Schematic representation of the directed coupling of a fluorescently labeled peptide with free Cys to HA-TA-Maleimide. The successful coupling was confirmed on SOS-PAGE.
Figure 22:
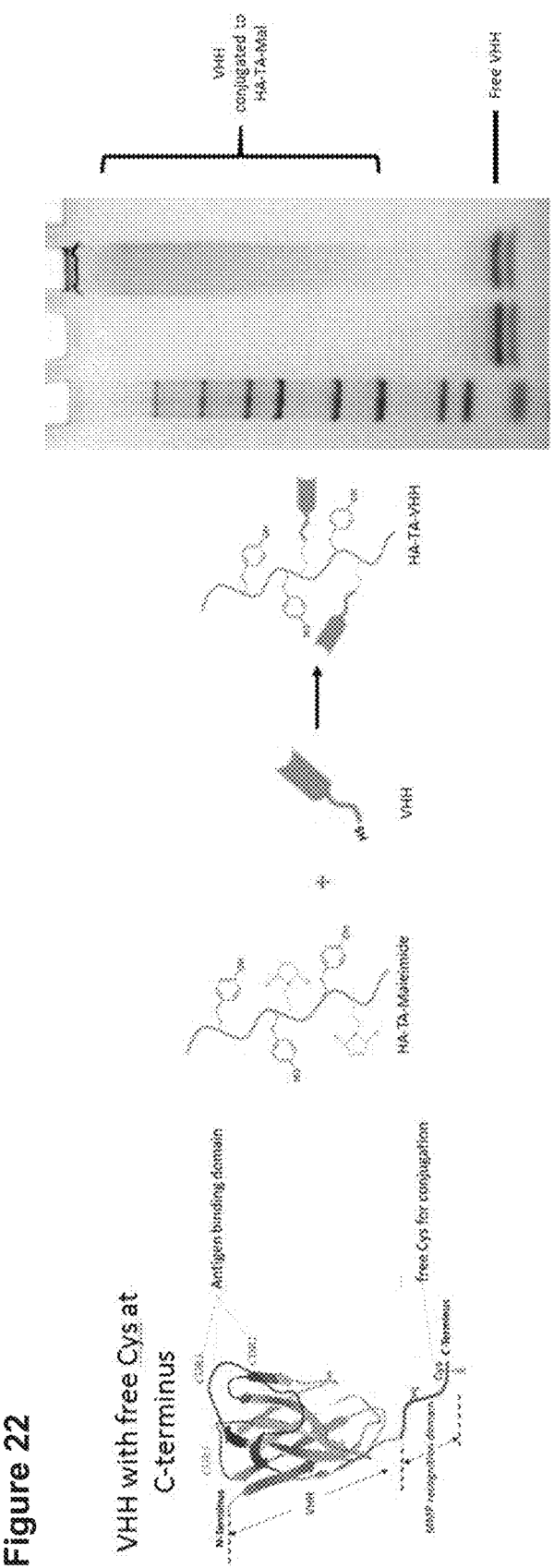
FIG. 22: Schematic representation of the directed coupling of a VHH with free Cys to HA-TA-Maleimide. The successful coupling was confirmed on SDS-PAGE.

Thus generated maleimide functionalized polymer conjugates can be used for the conjugation of peptides with a free-unpaired cysteine residue (FIG. 21) or antibody fragments (VHH) with an engineered free-unpaired cysteine introduced in the C-terminus of the protein using recombinant DNA technology (FIG. 22). To demonstrate this, a peptide with a free unpaired Cysteine residue was synthesized and labelled with a fluorescent dye. This peptide was reacted to the HA-TA-Maleimide polymer conjugate. Thus formed HA-TA-Peptide conjugate was subjected to SDS-PAGE gel electrophoresis side by side with the unconjugated Peptide. Fluorescence was subsequently used for visualization. As shown in FIG. 21, the molecular weight of the HA-TA-Peptide conjugates was increased compared to the unconjugated peptide demonstrating successful conjugation. Similarly, in FIG. 22 it is shown that the HA-TA-Maleimide polymer conjugate also reacted with an antibody fragment (VHH) in which an unpaired Cysteine residue was engineered at its C-terminus. Conjugation of the polymer-TA conjugates to the VHH using maleimide chemistry clearly induced an increase in the molecular weight of the VHH compared to free, unreacted VHH based on SDS-PAGE gel electrophoresis although not all VHH has reacted.

The examples demonstrate that it is possible to employ different strategies for obtaining polymer conjugates that can be used for generation of cytokine sinks, such as those based on hyaluronic acid and dextran polymers.

Cited Art

1. Grainger, D. W., Controlled-release and local delivery of therapeutic antibodies. Expert Opin Biol Ther, 2004. 4(7): p. 1029-44.

2. Chevalier, X., et al., Intraarticular injection of anakinra in osteoarthritis of the knee: a multicenter, randomized, double-blind, placebo-controlled study. Arthritis Rheum, 2009. 61(3): p. 344-52.

3. Joosten, L. A., et al., Anticytokine treatment of established type II collagen-induced arthritis in DBA/1 mice. A comparative study using anti-TNF alpha, anti-IL-1 alpha/beta, and IL-1Ra. Arthritis Rheum, 1996. 39(5): p. 797-809.

4. Giteau, A., et al., How to achieve sustained and complete protein release from PLGA-based microparticles? International Journal of Pharmaceutics, 2008. 350(1): p. 14-26.

5, Samad, A., Y. Sultana, and M. Aqil, Liposomal drug delivery systems: an update review. Curr Drug Deliv, 2007. 4(4): p. 297-305.

6. Bezemer, J. M., et al., Microspheres for protein delivery prepared from amphiphilic multiblock copolymers. 1. Influence of preparation techniques on particle characteristics and protein delivery. J Control Release, 2000. 67(2-3): p. 233-48.

7. Brown, K. E., et al., Gelatin/chondroitin 6-sulfate microspheres for the delivery of therapeutic proteins to the joint. Arthritis Rheum, 1998. 41(12): p. 2185-95.

8. Agarwal, R., et al., Synthesis of self-assembled IL-1Ra-presenting nanoparticles for the treatment of osteoarthritis. J Biomed Mater Res A, 2016. 104(3): p. 595-599.

9. Singh, A., et al., Nanoengineered particles for enhanced intra-articular retention and delivery of proteins. Adv Healthc Mater, 2014. 3(10): p. 1562-7, 1525.

10. Whitmire, R. E., et al., Self-assembling nanoparticles for intra-articular delivery of anti-inflammatory proteins. Biomaterials, 2012. 33(30): p. 7665-75.

11. Kohane, D. S., Microparticles and nanoparticles for drug delivery. Biotechnol Bioeng, 2007. 96(2): p. 203-9.

12. Pradal, J., et al., Effect of particle size on the biodistribution of nano- and microparticles following intra-articular injection in mice. Int J Pharm, 2016. 498(1-2): p. 119-29.

13. Sousa, F., et al., Nanoparticles for the delivery of therapeutic antibodies: Dogma or promising strategy? Expert Opin Drug Deliv, 2017. 14(10): p. 1163-1176.

14. Helmick, C. G., et al., Estimates of the prevalence of arthritis and other rheumatic conditions in the United States: Part I. Arthritis & Rheumatism, 2008. 58(1): p. 15-25.

15. CDC, Cost statistics osteoarthritis. 2015, Center for disease control and prevention.

16, Wang, R., Macromolecular engineering of in-situ forming hydrogels, Department of Developmental BioEngineering, University of Twente, Enschede, 2016, p. 180.

17. Jin, R. et al. (2007) Enzyme-mediated fast in situ formation of hydrogels from dextran-tyramine conjugates. Biomaterials 28 (18), 2791-800.

18. Kamperman, T. et al. (2017) Centering Single Cells in Microgels via Delayed Crosslinking Supports Long-Term 3D Culture by Preventing Cell Escape. Small 13 (22), 1603711-n/a.

19. Chicheportiche, D. and Reach, G. (1988) In vitro kinetics of insulin release by microencapsulated rat islets: effect of the size of the microcapsules. Diabetologia 31 (1), 54-7.

20. Headen, D. M. et al. (2014) Microfluidic-based generation of size-controlled, biofunctionalized synthetic polymer microgels for cell encapsulation. Advanced Materials 26 (19), 3003-8.

21. Pradal, J. et al. (2016) Effect of particle size on the biodistribution of nano- and microparticles following intra-articular injection in mice. Int J Pharm 498 (1-2), 119-29.

22. Formiga, F. R. et al. (2013) Biodegradation and heart retention of polymeric microparticles in a rat model of myocardial ischemia. Eur J Pharm Biopharm 85 (3 Pt A), 665-72.

23. Tran, V.-T. et al. (2011) Why and how to prepare biodegradable, monodispersed, polymeric microparticles in the field of pharmacy? International journal of pharmaceutics 407 (1-2), 1-11.

24. Lima, A. C. et al. (2012) Production methodologies of polymeric and hydrogel particles for drug delivery applications. Expert Opin Drug Deliv 9 (2), 231-48.

25. Buwalda, S. J. et al. (2014) Hydrogels in a historical perspective: from simple networks to smart materials, J Control Release 190, 254-73.

Refs in Examples

1. Strokappe, N. et al. (2012) Llama antibody fragments recognizing various epitopes of the CD4bs neutralize a broad range of HIV-1 subtypes A, B and C. PLoS One 7 (3), e33298.

2. Frenken, L. G. et al. (2000) Isolation of antigen specific llama VHH antibody fragments and their high level secretion by Saccharomyces cerevisiae. J Biotechnol 78 (1), 11-21.

3. Roovers, R. C. et al, (2007) Efficient inhibition of EGFR signaling and of tumour growth by antagonistic anti-EFGR Nanobodies. Cancer Immunol Immunother 56 (3), 303-317.

4. El Khattabi, M. et al. (2006) Llama single-chain antibody that blocks lipopolysaccharide binding and signaling: prospects for therapeutic applications. Clin Vaccine Immunol 13 (10), 1079-86.

5. Oliveira, S. et al. (2013) Targeting tumors with nanobodies for cancer imaging and therapy, J Control Release 172 (3), 607-17.

6. Zhang, Y. (2008) I-TASSER server for protein 3D structure prediction. BMC Bioinformatics 9, 40.

7. Roy, A. et al. (2010) I-TASSER: a unified platform for automated protein structure and function prediction. Nat Protoc 5 (4), 725-38.

8. Roy, A. et al. (2012) COFACTOR: an accurate comparative algorithm for structure-based protein function annotation. Nucleic Acids Res 40 (Web Server issue), W471-7.

9. Wang, R., Macromolecular engineering of in-situ forming hydrogels, Department of Developmental BioEngineering, University of Twente, Enschede, 2016, p. 180.

10. Jin, R. et al. (2007) Enzyme-mediated fast in situ formation of hydrogels from dextran-tyramine conjugates. Biomaterials 28 (18), 2791-800.

11. Kamperman, T. et al. (2017) Centering Single Cells in Microgels via Delayed Crosslinking Supports Long-Term 3D Culture by Preventing Cell Escape. Small 13 (22), 1603711-n/a.

12. Both, S. K. et al. (2007) A rapid and efficient method for expansion of human mesenchymal stem cells. Tissue Eng 13 (1), 3-9.

13. Moreira Teixeira, L. S. et al. (2012) High throughput generated micro-aggregates of chondrocytes stimulate cartilage formation in vitro and in vivo. Eur Cell Mater 23, 387-99.

14. Cadee, J. A. et al, (2000) In vivo biocompatibility of dextran-based hydrogels. Journal of Biomedical Materials Research 50 (3), 397-404.

15. De Groot, C. J. et al. (2001) In vitro biocompatibility of biodegradable dextran-based hydrogels tested with human fibroblasts. Biomaterials 22 (11), 1197-203.

16. Segura, T. et al. (2005) Crosslinked hyaluronic acid hydrogels: a strategy to functionalize and pattern. Biomaterials 26 (4), 359-71.

17. Seidlits, S. K, et al. (2009) High-Resolution Patterning of Hydrogels in Three Dimensions using Direct-Write Photofabrication for Cell Guidance. Advanced Functional Materials 19 (22), 3543-3551.

18. Chaudhuri, O. et al. (2016) Hydrogels with tunable stress relaxation regulate stem cell fate and activity. Nat Mater 15 (3), 326-34.

19. Burdick, J. A. and Anseth, K. S. (2002) Photoencapsulation of osteoblasts in injectable RGD-modified PEG hydrogels for bone tissue engineering. Biomaterials 23 (22), 4315-23.

What is claimed is:

1. A hydrogel particle, comprising:
an average cross-sectional diameter in the range from 1 micrometer (μm) to 1000 μm,
wherein the particle comprises a first polymer network with an average mesh size that allows diffusion of a molecule with an hydrodynamic radius of 1000 nanometer (nm) or less into the first polymer network,
wherein the particle comprises a binding molecule that is immobilized by the first polymer network, and the binding molecule specifically binds the molecule with hydrodynamic radius of 1000 nanometer (nm) or less, wherein the binding molecule is a binding peptide; an antibody or antigen binding part thereof; a ligand binding receptor; or an aptamer, and
wherein the hydrogel comprises a dextran-tyramine hydrogel; a hyaluronic acid-tyramine hydrogel; a PEG-tyramine hydrogel or a combination thereof.

2. The hydrogel particle of claim 1, wherein the first polymer network has an average mesh size that prevents diffusion of a molecule with an average hydrodynamic radius of more than 1000 nm to diffuse into the first polymer network.

3. The hydrogel particle of claim 1, wherein the mesh size of the first polymer network is determined by measuring the diffusion of molecules with a known average hydrodynamic radius.

4. The hydrogel particle of claim 1, wherein the antibody or antigen binding part thereof is a single-domain antibody.

5. The hydrogel particle of claim 4, wherein the single-domain antibody is a variable domain of a single chain heavy chain only antibody of a camelid or cartilaginous fish (also referred to as VHH and VNAR respectively).

6. The hydrogel particle of claim 1, wherein the particle comprises a second polymer network that surrounds said first polymer network, wherein the second polymer network is devoid of said binding molecule.

7. The hydrogel particle of claim 6, wherein the second polymer network has an average mesh size that is the same or smaller than the mesh size of the first polymer network.

8. The hydrogel particle of claim 6, wherein the second polymer network average mesh size that is not penetrable for a molecule with an average hydrodynamic radius of more than 100 nm.

9. The hydrogel particle of claim 5, wherein the second polymer network has a thickness of 1 nanometer-450 μm.

10. The hydrogel particle of claim 6, wherein the second polymer network comprises a targeting moiety or a biological compartment retention molecule.

11. The hydrogel particle of claim 1, wherein the binding molecule binds a cytokine, a soluble antigen or an auto-antibody.

12. An aqueous composition comprising hydrogel particles of claim 1.

13. An aqueous composition suitable for injection comprising the hydrogel particle of claim 1.

14. The hydrogel particle of claim 1, for use in the treatment of a patient with an over-active immune system, a cancer, an over-active hormone and/or cytokine producing cells, inflammation, or joint-inflammation.

15. The hydrogel particle of claim 1, wherein the hydrogel comprises a dextran-tyramine hydrogel having maleimide groups r a hyaluronic acid-tyramine hydrogel having maleimide groups.

16. The hydrogel particle according to claim 2, wherein the first polymeric network has an average mesh size that prevents diffusion of a molecule with an average hydrodynamic radius of more than 100 nm.

17. The hydrogel particle according to claim 2, wherein the first polymeric network has an average mesh size that prevents diffusion of a molecule with an average hydrodynamic radius of more than 5 nm.

18. The hydrogel particle according to claim 8, wherein the second polymer network average mesh size that is not penetrable for a molecule with an average hydrodynamic radius of more than 5 nm.

19. The hydrogel particle according to claim 8, wherein the second polymer network average mesh size that is not penetrable for a molecule with an average hydrodynamic radius of more than 4 nm.

* * * * *